(12) United States Patent
Kandimalla et al.

(10) Patent No.: US 7,790,168 B2
(45) Date of Patent: Sep. 7, 2010

(54) MODULATION OF IMMUNOSTIMULATORY ACTIVITY OF IMMUNOSTIMULATORY OLIGONUCLEOTIDE ANALOGS BY POSITIONAL CHEMICAL CHANGES

(75) Inventors: Ekambar R. Kandimalla, Southboro, MA (US); Qiuyan Zhao, Southboro, MA (US); Dong Yu, Westboro, MA (US); Sudhir Agrawal, Shrewsbury, MA (US)

(73) Assignee: Idera Pharmaceuticals, Inc, Cambridge, MA (US)

( * ) Notice: Subject to any disclaimer, the term of this patent is extended or adjusted under 35 U.S.C. 154(b) by 1096 days.

(21) Appl. No.: 10/694,207

(22) Filed: Oct. 27, 2003

(65) Prior Publication Data

US 2006/0135454 A1 Jun. 22, 2006

Related U.S. Application Data

(60) Division of application No. 09/965,116, filed on Sep. 26, 2001, now Pat. No. 7,262,286, which is a continuation-in-part of application No. 09/712,898, filed on Nov. 15, 2000, now abandoned.

(60) Provisional application No. 60/235,452, filed on Sep. 26, 2000, provisional application No. 60/235,453, filed on Sep. 26, 2000.

(51) Int. Cl.
*A61K 39/00* (2006.01)
*A61K 39/385* (2006.01)
*A01N 43/04* (2006.01)
*C07H 21/02* (2006.01)

(52) U.S. Cl. .............. 424/184.1; 424/193.1; 424/278.1; 514/44; 536/23.1

(58) Field of Classification Search ........................ None
See application file for complete search history.

(56) References Cited

U.S. PATENT DOCUMENTS 5,149,798 A   9/1992 Agrawal et al. ............... 536/27
6,207,646 B1 * 3/2001 Krieg et al.
6,562,798 B1 * 5/2003 Schwartz

FOREIGN PATENT DOCUMENTS

WO       WO99/62923       12/1999

OTHER PUBLICATIONS

Verthelyi et al. The Journal of Immunology, 168:1659-1663, 2002.*
Dittmer et al. Current Opinion in Microbiology, 6:472-477, 2003.*
Vollmer et al. Antisense and Nucleic Acid Drug Development, 12:165-175, 2002.*
Donnelly et al. Nature Medicine, 2003, vol. 9, pp. 1354-1356.*
DeGruijl et al. Nature Medicine, 1999, vol. 5, pp. 1124-1125.*
Bitton R. J. Current Opinion in Molecular Therapeutics, 2004, vol. 6, pp. 17-26.*
Weiner G. J. Leukocyte Biology, 2000. vol. 68, pp. 455-463.*
Krieg et al. Nature, 1995. vol. 374, pp. 546-549.*
Ballas et al. Journal of Immunology, 2001. vol. 167, pp. 4878-4886.*
Agrawal et al. TRENDS in Molecular Medicine, 2002. vol. 8, pp. 114-120.*
Khorana et al. (1972) "Studies on Polynucleotides," *J. Molec. Biol.* 72:209.
Reese (1978) "The Chemical Synthesis of Oligo- and Poly-Nucleotides By The Phosporotriester Approach," *Tetrahedron* 34:3143-3179.
Beaucage et al. (1981) "Deoxynucleoside Phosphoramidites—A New Class of Key Intermediates for Deoxypolynucleotide Synthesis," *Tetrahedron Lett.* 22:1859-1862.
Connolly et al. (1984) "Synthesis and Characterization of an Octanucleotide Containing the *Eco*RI Recognition Sequence With A Phosphorothioate Group At The Cleavage Site," Biochemistry 23:3443.
Agrawal et al. (1987) "Oligodeoxynucleotise Methylphosphonates: Synthesis and Enzymic Degradation," *Tetrahedron Lett.* 28(31):3539-3542.
Jager et al. (1988) Oligonucleotide N-Alkylphosphoroamidates: Synthesis and Binding to Polynucleotides, *Biochemistry* 27:7237.
Agrawal et al. (1988) Oligodeoxynucleoside Phosphoroamidates and Phosporothioates As Inhibitors of Human Immunodeficiency Virus, *Proc. Natl. Acad. Sci. USA* 85:7079-7083.
Zon et al. (1991) "Phosphorothioate Oligonucleotides" *Oligonucleotides and Analogues: A Practical Approach* pp. 87-108.
Kuramoto et al. (1992) "Oligonucleotide Sequences Required For Natural Killer Cell Activation," *Jpn. J. Cancer Res.* 83:1128-1131.
Crooke (1993) "An Overview of Progress in Antisense Therapeutics," 8 *Antisense & Nucl. Acid Drug Dev.* 115-122 CRC Press, Boca Raton, Florida.
Zon (1993) "Protocols for Oligonucleotides and Analogs," *Methods in Molecular Biology* vol. 20, pp. 165-189.
Pisetsky et al. (1994)"Stimulation of Murine Lymphocyte Proliferation By A Phosphorothioate Oligonucleotide With Antisense Activity For Herpes Simplex Virus," 54 *Life Sci.* 101.
Yamamoto et al. (1994) "Lipofection of Synthetic Oligodeoxyribonucleotide Having a Palindromic Sequence of AACGTT to Murine Spenocytes Enhances Interferon Production and Natural Killer Activity," 38 *Microbiol. Immunol.* 831.
Agrawal et al. (1995) "Modified Oligonucleotides as Therapeutic and Diagnostic Agents," *Curr.Opin.Biotechnol.* 6:12-19.

(Continued)

*Primary Examiner*—David J. Blanchard
(74) *Attorney, Agent, or Firm*—Wayne A. Keown; Preti Flaherty

(57) ABSTRACT

The invention relates to the therapeutic use of oligonucleotides or oligonucleotide analogs as immunostimulatory agents in immunotherapy applications. The invention provides methods for enhancing the immune response caused by immunostimulatory oligonucleotide compounds.

7 Claims, 53 Drawing Sheets

OTHER PUBLICATIONS

Krieg et al. (1995) "CpG Motifs In Bacterial DNA Trigger Direct B-Cell Activation," *Nature* 371:546-549.

Klinman et al. (1996) "CpG Motifs Present in Bacterial DNA Rapidly Induce Lymphocytes to Secrete Interleukin 6, Interleukin 12, and Interferon γ," 93 *Proc. Natl. Acad. Sci. USA* 2879.

Liang et al. (1996) "Activation of Human B Cells By phosphorothioate Oligodeoxynucleotides," *J. Clin. Invest.* 98:1119-1129.

Zhao et al. (1996) "Effect of Different Chemically Modified Oligodeoxynucleotides on Immune Stimulation," *Biochem. Pharm.* 51-173-182.

Chu et al. (1997) "CpG Oligodeoxynucleotides Act As Adjuvants That Switch On T Helper 1 (Th1) Immunity," 186 *J. Exp. Med.* 1623.

Dunford et al. (1997) "Antisense 97: Targeting the Molecular Basis of Disease" (*Nature Biotechnology*) Conference Abstract, pp. 40.

Sparwasser et al. (1997) "Macrophages Sense Pathogens Via DNA Motifs: Induction of Tumor Necrosis Factor-α-Mediated Shock,"27 *Eur. J. Immunol.* 1671.

Zhao et al. (1997) "Pattern and Kinetics of Cytokine Production Following Administration of Phosphorothioate Oligonucleotides In Mice," 7 *Antisense Nucleic Acid Drug. Dev.* 495.

McCluside et al. (1998) "Cutting Edge: CpG DNA Is A Potent Enhancer of Systemic and Mucosal Immune Responses Against Hepatitis B Surface Antigen with Intranasal Administration to Mice," *J. Immunol.* 161:4463-4466.

Moldoveanu et al. (1998) "CpG DNA, A Novel Immune Enhancer for Systemic and Mucosal Immunization With Influenza Virus," *Vaccine* 16:1216-1224.

Sparwasser et al. (1998) "Bacterial DNA and Immunostimulatory CpG Oligonucleotides Trigger Maturation and ACtivation of Murine Dendritic Cells," 28 *Eur. J. Immunol.* 2045.

Tokunaga et al. (1999) "How BCG Led to the Discovery of Immunostimulatory DNA," 52 *Jap. J. Infect. Dis.* 1.

Zhao et al. (1999) "Site of Chemical Modifications in CpG Containing Phosphorothioate Oligodeoxynucleotide Modulates its Immunostimulatory Activity," *Bioorg. & Med. Chem. Lett.* 9:3453-3458.

Agrawal et al. (2000) "Antisense Therapeutics: Is It As Simple As Complementary Base Recognition," 6 *Mol. Med. Today* 72.

Zhao et al. (2000) "Immunostimulatory Activity of CpG Containing Phosphorothioate Oligodeoxynucleotide is Modulated by Modification of a Single Deoxynucleoside," *Bioorg. & Med. Chem. Lett.* 10:1051-1054.

Agrawal et al., "Antisense therapeutics", Curr. Opin.Chem. Biol., 2:519-528, 1998.

Chaix et al., "3'-3' Linked Oligonucleotides:Synthesis and Stability Studies", Biorg. & Med.Chem., 6:827-832, 1996.

Klinman, "Therapeutic Applications of CpG-Containing Oligodeoxynucleotides", Antisense & Nucl. Acid Drug Dev., 8:181-184, 1998.

Yu et al., "Accessible 5'-End of CpG-Containing . . . ", Bioorganic & Medicinal Chemistry Lett., 10:2585-2588, 2000.

Kandimalla et al., "Effect of Chemical Modifications . . . ", Bioorganic & Medicinal Chemistry, 9:807-813, 2001.

International Search Report (PCT App. No. PCT/US01/30137).

\* cited by examiner

OLIGODEOXYNUCLEOTIDE PHOSPHOROTHIOATES AND SITE OF MODIFICATION

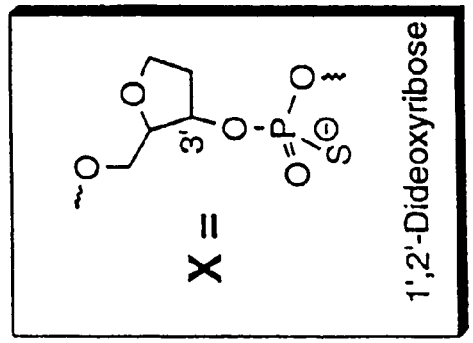

X = [structure] 1',2'-Dideoxyribose

| | Oligo No. | Sequence & Modification |
|---|---|---|
| SEQ ID NO.: 8 | 8 | 5'-CCTACTAGCGTTCTCATC-3' (133-1) |
| SEQ ID NO.: 9 | 9 | 5'-CCTACTAGCXTTCTCATC-3' (139-2) |
| SEQ ID NO.: 10 | 10 | 5'-CCTACTAXCGTTCTCATC-3' (133-2) |
| SEQ ID NO.: 11 | 11 | 5'-CCTACTXGCGTTCTCATC-3' (139-3) |
| SEQ ID NO.: 12 | 12 | 5'-CCTACXAGCGTTCTCATC-3' (133-3) |
| SEQ ID NO.: 13 | 13 | 5'-CCTAXTAGCGTTCTCATC-3' (139-4) |
| SEQ ID NO.: 14 | 14 | 5'-CCTXCTAGCGTTCTCATC-3' (133-4) |
| SEQ ID NO.: 15 | 15 | 5'-CCTXCTAGCCTTCTCATC-3' (145-10a) |
| SEQ ID NO.: 16 | 16 | 5'-CCTACTAGCGXTCTCATC-3' (133-5) |
| SEQ ID NO.: 17 | 17 | 5'-CCTACTAGCGTXCTCATC-3' (139-7) |
| SEQ ID NO.: 18 | 18 | 5'-CCTACTAGCGTTXTCATC-3' (133-6) |
| SEQ ID NO.: 19 | 19 | 5'-CCTACTAGCGTTCXCATC-3' (139-8) |
| SEQ ID NO.: 20 | 20 | 5'-CCTXXTAGCGTTCTCATC-3' (133-12) |
| SEQ ID NO.: 21 | 21 | 5'-XXTACTAGCGTTCTCATC-3' (139-6) |
| SEQ ID NO.: 22 | 22 | 5'-CCTACTAGCGTTCXXATC-3' (139-9) |
| SEQ ID NO.: 23 | 23 | 5'-CCTXCTXGCGTTCTCATC-3' (145-10b) |

FIG. 1A

OLIGODEOXYNUCLEOTIDE PHOSPHOROTHIOATES AND SITE OF MODIFICATION

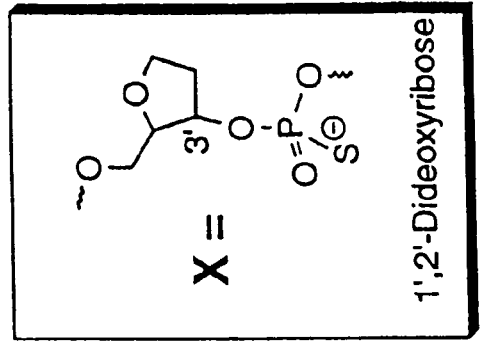

X = 1',2'-Dideoxyribose

| Oligo No. | | Sequence & Modification |
|---|---|---|
| SEQ ID NO.: 8 | 8 | 5'-CCTACTAGCGTTCTCATC-3' (133-1) |
| SEQ ID NO.: 9 | 9 | 5'-CCTACTAGCXTTCTCATC-3' (139-2) |
| SEQ ID NO.: 10 | 10 | 5'-CCTACTAXCGTTCTCATC-3' (133-2) |
| SEQ ID NO.: 11 | 11 | 5'-CCTACTXGCGTTCTCATC-3' (139-3) |
| SEQ ID NO.: 12 | 12 | 5'-CCTACXAGCGTTCTCATC-3' (133-3) |
| SEQ ID NO.: 13 | 13 | 5'-CCTAXTAGCGTTCTCATC-3' (139-4) |
| SEQ ID NO.: 14 | 14 | 5'-CCTXCTAGCGTTCTCATC-3' (133-4) |
| SEQ ID NO.: 15 | 15 | 5'-CCTXCTAGCCGTTCTCATC-3' (145-10a) |
| SEQ ID NO.: 16 | 16 | 5'-CCTACTAGCGXTCTCATC-3' (133-5) |
| SEQ ID NO.: 17 | 17 | 5'-CCTACTAGCGTXCTCATC-3' (139-7) |
| SEQ ID NO.: 18 | 18 | 5'-CCTACTAGCGTTXTCATC-3' (133-6) |
| SEQ ID NO.: 19 | 19 | 5'-CCTACTAGCGTTCXCATC-3' (139-8) |
| SEQ ID NO.: 20 | 20 | 5'-CCTXXTAGCGTTCTCATC-3' (133-12) |
| SEQ ID NO.: 21 | 21 | 5'-XXTACTAGCGTTCTCATC-3' (139-6) |
| SEQ ID NO.: 22 | 22 | 5'-CCTACTAGCGTTCXXATC-3' (139-9) |
| SEQ ID NO.: 23 | 23 | 5'-CCTXCTXGCGTTCTCATC-3' (145-10b) |

FIG. 2A

OLIGODEOXYNUCLEOTIDE PHOSPHOROTHIOATES AND SITE OF MODIFICATION

X = 1',2'-Dideoxyribose

| | Oligo No. | Sequence & Modification |
|---|---|---|
| SEQ ID NO.: 1 | 1 | 5'-CTATCTGAC GTTCTCTGT-3' (131-1) |
| SEQ ID NO.: 105 | 2 | 5'-CTATCTGAXGTTCTCTGT-3' (131-13) |
| SEQ ID NO.: 106 | 3 | 5'-CTATCTGXCGTTCTCTGT-3' (131-2) |
| SEQ ID NO.: 107 | 4 | 5'-CTATCXGACGTTCTCTGT-3' (131-3) |
| SEQ ID NO.: 108 | 5 | 5'-CTAXCTGACGTTCTCTGT-3' (131-4) |
| SEQ ID NO.: 109 | 6 | 5'-CTATCTGACGXTCTCTGT-3' (131-5) |
| SEQ ID NO.: 110 | 7 | 5'-CTATCTGACGTTXTCTGT-3' (131-6) |

OLIGODEOXYNUCLEOTIDE PHOSPHOROTHIOATES AND SITE OF MODIFICATION

X = 1',2'-Dideoxyribose

| | Oligo No. | Sequence & Modification |
|---|---|---|
| SEQ ID NO.: 1 | 1 | 5'-CTATCTGACGTTCTCTGT-3' (131-1) |
| SEQ ID NO.: 105 | 2 | 5'-CTATCTGAXGTTCTCTGT-3' (131-13) |
| SEQ ID NO.: 106 | 3 | 5'-CTATCTGXCGTTCTCTGT-3' (131-2) |
| SEQ ID NO.: 107 | 4 | 5'-CTATCXGACGTTCTCTGT-3' (131-3) |
| SEQ ID NO.: 108 | 5 | 5'-CTAXCTGACGTTCTCTGT-3' (131-4) |
| SEQ ID NO.: 109 | 6 | 5'-CTATCTGACGXTCTCTGT-3' (131-5) |
| SEQ ID NO.: 110 | 7 | 5'-CTATCTGACGTTXTCTGT-3' (131-6) |

OLIGODEOXYNUCLEOTIDE PHOSPHOROTHIOATES AND MODIFICATION OF LINKAGES

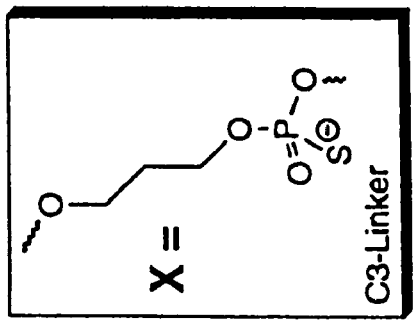

X = [C3-Linker structure]

| | Oligo No. | Sequence & Modification |
|---|---|---|
| SEQ ID NO.: 8 | 133-1 | 5'-CCTACTAGCGTTCTCATC-3' |
| SEQ ID NO.: 24 | 141-2 | 5'-CCTACTAGCXTTCTCATC-3' |
| SEQ ID NO.: 25 | 141-3 | 5'-CCTACTXGCGTTCTCATC-3' |
| SEQ ID NO.: 26 | 141-4 | 5'-CCTAXTAGCGTTCTCATC-3' |
| SEQ ID NO.: 27 | 141-5 | 5'-CCTXXTAGCGTTCTCATC-3' |
| SEQ ID NO.: 28 | 141-6 | 5'-XXTACTAGCGTTCTCATC-3' |
| SEQ ID NO.: 29 | 141-7 | 5'-CCTACTAGCGTXCTCATC-3' |
| SEQ ID NO.: 30 | 141-8 | 5'-CCTACTAGCGTTCXCATC-3' |
| SEQ ID NO.: 31 | 141-9 | 5'-CCTACTAGCGTTCXXATC-3' |
| SEQ ID NO.: 1 | 131-1 | 5'-CTATCTGACGTTCTCTGT-3' |
| SEQ ID NO.: 32 | 137-2 | 5'-CTATCTGXCGTTCTCTGT-3' |
| SEQ ID NO.: 33 | 137-3 | 5'-CTATCXGACGTTCTCTGT-3' |
| SEQ ID NO.: 34 | 137-4 | 5'-CTAXCTGACGTTCTCTGT-3' |

FIG. 5A

OLIGODEOXYNUCLEOTIDE PHOSPHOROTHIOATES AND MODIFICATION OF LINKAGES

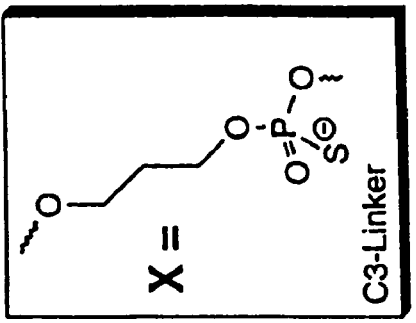

| | Oligo No. | Sequence & Modification |
|---|---|---|
| SEQ ID NO.: 8 | 133-1 | 5'-CCTACTAGCGTTCTCATC-3' |
| SEQ ID NO.: 24 | 141-2 | 5'-CCTACTAGCXTTCTCATC-3' |
| SEQ ID NO.: 25 | 141-3 | 5'-CCTACTXGCGTTCTCATC-3' |
| SEQ ID NO.: 26 | 141-4 | 5'-CCTAXTAGCGTTCTCATC-3' |
| SEQ ID NO.: 27 | 141-5 | 5'-CCTXXTAGCGTTCTCATC-3' |
| SEQ ID NO.: 28 | 141-6 | 5'-XXTACTAGCGTTCTCATC-3' |
| SEQ ID NO.: 29 | 141-7 | 5'-CCTACTAGCGTXCTCATC-3' |
| SEQ ID NO.: 30 | 141-8 | 5'-CCTACTAGCGTTCXCATC-3' |
| SEQ ID NO.: 31 | 141-9 | 5'-CCTACTAGCGTTCXXATC-3' |
| SEQ ID NO.: 1 | 131-1 | 5'-CTATCTGACGTTCTCTGT-3' |
| SEQ ID NO.: 32 | 137-2 | 5'-CTATCTGXCGTTCTCTGT-3' |
| SEQ ID NO.: 33 | 137-3 | 5'-CTATCXGACGTTCTCTGT-3' |
| SEQ ID NO.: 34 | 137-4 | 5'-CTAXCTGACGTTCTCTGT-3' |

FIG. 6A

OLIGODEOXYNUCLEOTIDE PHOSPHOROTHIOATES AND SITE OF MODIFICATION

| | Oligo No. | Sequence & Modification |
|---|---|---|
| SEQ ID NO.: 1 | 1 | 5'-CTATCTGAC<u>G</u>TTCTCTGT-3' (131-1) |
| SEQ ID NO.: 35 | 2 | 5'-CTAXCTGACGTTCTCTGT-3' (153-1) |
| SEQ ID NO.: 36 | 3 | 5'-CTATCTGACGTTCXCTGT-3' (153-2) |
| SEQ ID NO.: 37 | 4 | 5'-CTAYCTGACGTTCTCTGT-3' (153-3) |
| SEQ ID NO.: 38 | 5 | 5'-CTATCTGACGTTCYCTGT-3' (153-4) |
| SEQ ID NO.: 8 | 6 | 5'-CCTACTAGCGTTCTCATC-3' (133-1) |
| SEQ ID NO.: 39 | 7 | 5'-CCTXCTAGCGTTCTCATC-3' (155-1) |
| SEQ ID NO.: 40 | 8 | 5'-CCTACTAGCGTTCXCATC-3' (155-2) |
| SEQ ID NO.: 41 | 9 | 5'-CCTYCTAGCGTTCTCATC-3' (155-3) |
| SEQ ID NO.: 42 | 10 | 5'-CCTACTAGCGTTCYCATC-3' (155-4) |

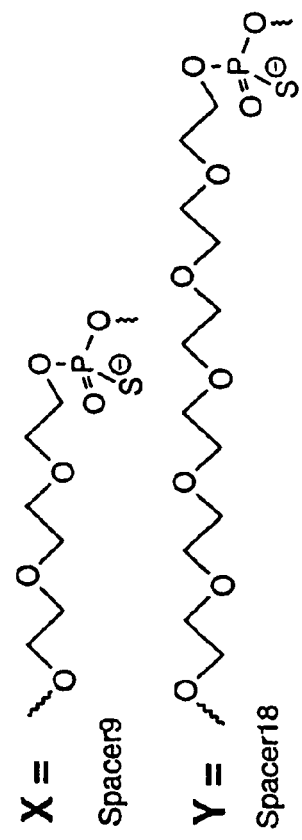

X = Spacer9

Y = Spacer18

FIG. 7A

OLIGODEOXYNUCLEOTIDE PHOSPHOROTHIOATES AND SITE OF MODIFICATION

| | Oligo No. | Sequence & Modification |
|---|---|---|
| SEQ ID NO.: 1 | 1 | 5'-CTATCTGA<u>CG</u>TTCTCTGT-3' (131-1) |
| SEQ ID NO.: 35 | 2 | 5'-CTAXCTGACGTTCTCTGT-3' (153-1) |
| SEQ ID NO.: 36 | 3 | 5'-CTATCTGACGTTCXCTGT-3' (153-2) |
| SEQ ID NO.: 37 | 4 | 5'-CTAYCTGACGTTCTCTGT-3' (153-3) |
| SEQ ID NO.: 38 | 5 | 5'-CTATCTGACGTTCYCTGT-3' (153-4) |
| SEQ ID NO.: 8 | 6 | 5'-CCTACTAGCGTTCTCATC-3' (133-1) |
| SEQ ID NO.: 39 | 7 | 5'-CCTXCTAGCGTTCTCATC-3' (155-1) |
| SEQ ID NO.: 40 | 8 | 5'-CCTACTAGCGTTCXCATC-3' (155-2) |
| SEQ ID NO.: 41 | 9 | 5'-CCTYCTAGCGTTCTCATC-3' (155-3) |
| SEQ ID NO.: 42 | 10 | 5'-CCTACTAGCGTTCYCATC-3' (155-4) |

X = Spacer9

Y = Spacer18

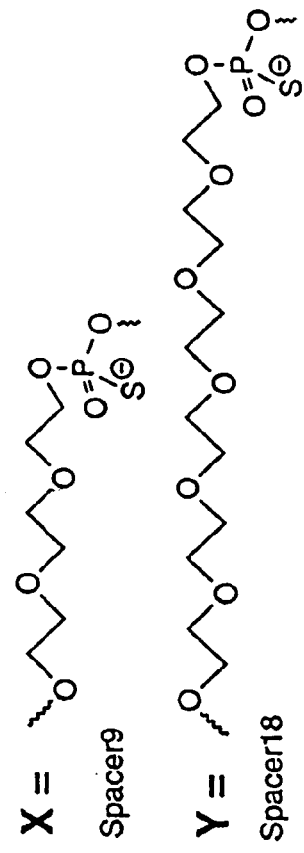

FIG. 8A

OLIGODEOXYNUCLEOTIDE PHOSPHOROTHIOATES AND SITE OF MODIFICATION

| Oligo No. | | Sequence & Modification |
|---|---|---|
| SEQ ID NO.: 1 | 1 | 5'-CTATCTGACGTTCTCTGT-3' (131-1) |
| SEQ ID NO.: 43 | 2 | 5'-CTATCTGXCGTTCTCTGT-3' (157-1) |
| SEQ ID NO.: 44 | 3 | 5'-CTATCTXACGTTCTCTGT-3' (157-2) |
| SEQ ID NO.: 45 | 4 | 5'-CTAXCTGACGTTCTCTGT-3' (157-3) |
| SEQ ID NO.: 46 | 5 | 5'-CTATCTGACGTXCTCTGT-3' (157-4) |
| SEQ ID NO.: 47 | 6 | 5'-CTATCTGACGTTCXCTGT-3' (157-5) |

OLIGODEOXYNUCLEOTIDE PHOSPHOROTHIOATES AND SITE OF MODIFICATION

| | Oligo No. | Sequence & Modification |
|---|---|---|
| SEQ ID NO.: 1 | 1 | 5'-CTATCTGACGTTCTCTGT-3' (131-1) |
| SEQ ID NO.: 43 | 2 | 5'-CTATCTGXCGTTCTCTGT-3' (157-1) |
| SEQ ID NO.: 44 | 3 | 5'-CTATCTXACGTTCTCTGT-3' (157-2) |
| SEQ ID NO.: 45 | 4 | 5'-CTAXCTGACGTTCTCTGT-3' (157-3) |
| SEQ ID NO.: 46 | 5 | 5'-CTATCTGACGTXCTCTGT-3' (157-4) |
| SEQ ID NO.: 47 | 6 | 5'-CTATCTGACGTTCXCTGT-3' (157-5) |

OLIGODEOXYNUCLEOTIDE PHOSPHOROTHIOATES AND MODIFICATION OF LINKAGES

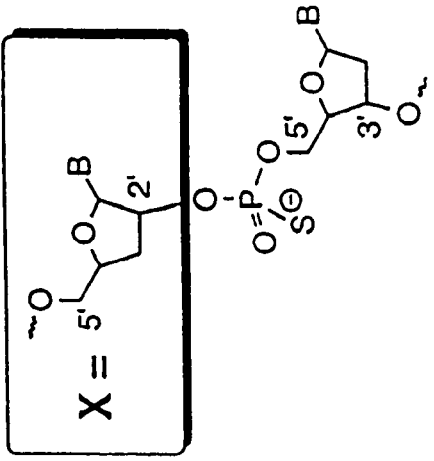

3'-Deoxynucleoside

| Oligo No. | Sequence & Modification |
|---|---|
| SEQ ID NO.: 1   131-1 | 5'-CTATCTGACGTTCTCTGT-3' |
| SEQ ID NO.: 48  159-1 | 5'-CTATCTGACXTTCTCTGT-3' |
| SEQ ID NO.: 49  159-2 | 5'-CTATCTGAXGTTCTCTGT-3' |
| SEQ ID NO.: 50  159-3 | 5'-CTATXTGACGTTCTCTGT-3' |
| SEQ ID NO.: 51  159-4 | 5'-CTATCTGACGTTCTXTGT-3' |
| SEQ ID NO.: 8   133-1 | 5'-CCTACTAGCGTTCTCATC-3' |
| SEQ ID NO.: 52  161-1 | 5'-CCTACTAGCXTTCTCATC-3' |
| SEQ ID NO.: 53  161-2 | 5'-CCTACTAGXGTTCTCATC-3' |
| SEQ ID NO.: 54  161-3 | 5'-CCTACTAXCGTTCTCATC-3' |
| SEQ ID NO.: 55  161-4 | 5'-CCTAXTAGCGTTCTCATC-3' |
| SEQ ID NO.: 56  161-5 | 5'-CCTACTAGCGTTCTXATC-3' |

FIG. 11A

OLIGODEOXYNUCLEOTIDE PHOSPHOROTHIOATES AND MODIFICATION OF LINKAGES

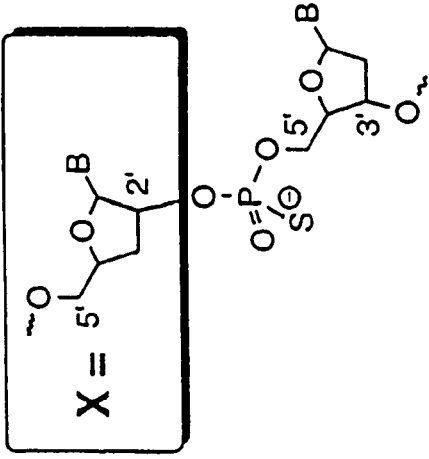

3'-Deoxynucleoside

| Oligo No. | | Sequence & Modification |
|---|---|---|
| SEQ ID NO.: 1 | 131-1 | 5'-CTATCTGACGTTCTCTGT-3' |
| SEQ ID NO.: 48 | 159-1 | 5'-CTATCTGACXTTCTCTGT-3' |
| SEQ ID NO.: 49 | 159-2 | 5'-CTATCTGAXGTTCTCTGT-3' |
| SEQ ID NO.: 50 | 159-3 | 5'-CTATXTGACGTTCTCTGT-3' |
| SEQ ID NO.: 51 | 159-4 | 5'-CTATCTGACGTTCTXTGT-3' |
| SEQ ID NO.: 8 | 133-1 | 5'-CCTACTAGCGTTCTCATC-3' |
| SEQ ID NO.: 52 | 161-1 | 5'-CCTACTAGCXTTCTCATC-3' |
| SEQ ID NO.: 53 | 161-2 | 5'-CCTACTAGXGTTCTCATC-3' |
| SEQ ID NO.: 54 | 161-3 | 5'-CCTACTAXCGTTCTCATC-3' |
| SEQ ID NO.: 55 | 161-4 | 5'-CCTAXTAGCGTTCTCATC-3' |
| SEQ ID NO.: 56 | 161-5 | 5'-CCTACTAGCGTTCTXATC-3' |

FIG. 12A

OLIGODEOXYNUCLEOTIDE PHOSPHOROTHIOATES AND MODIFICATION OF LINKAGES

| | Oligo No. | Sequence & Modification |
|---|---|---|
| SEQ ID NO.: 1 | 131-1 | 5'-CTATCTGACGTTCTCTGT-3' |
| SEQ ID NO.: 57 | 167-1 | 5'-CTATCTGXCGTTCTCTGT-3' |
| SEQ ID NO.: 58 | 167-2 | 5'-CTATCTXACGTTCTCTGT-3' |
| SEQ ID NO.: 59 | 167-3 | 5'-CTATCXGACGTTCTCTGT-3' |
| SEQ ID NO.: 60 | 167-4 | 5'-CTATXTGACGTTCTCTGT-3' |
| SEQ ID NO.: 61 | 167-5 | 5'-CTAXCTGACGTTCTCTGT-3' |
| SEQ ID NO.: 62 | 167-6 | 5'-CTXXCTGACGTTCTCTGT-3' |
| SEQ ID NO.: 63 | 167-7 | 5'-CTATCTGACGXTCTCTGT-3' |
| SEQ ID NO.: 64 | 167-8 | 5'-CTATCTGACGTXCTCTGT-3' |
| SEQ ID NO.: 65 | 167-9 | 5'-CTATCTGACGTTXTCTGT-3' |
| SEQ ID NO.: 66 | 167-10 | 5'-CTATCTGACGTTCXCTGT-3' |
| SEQ ID NO.: 67 | 16711 | 5'-CTATCTGACGTTCTXTGT-3' |
| SEQ ID NO.: 68 | 167-12 | 5'-CTATCTGACGTTCTXXGT-3' |

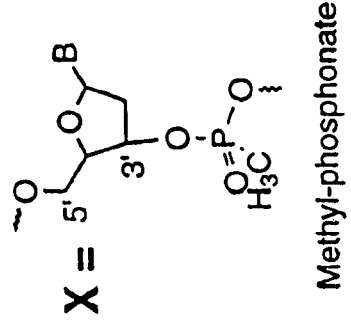

X = Methyl-phosphonate

FIG. 13A

OLIGODEOXYNUCLEOTIDE PHOSPHOROTHIOATES AND MODIFICATION OF LINKAGES

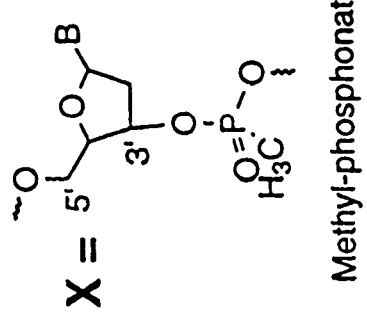

Methyl-phosphonate

| Oligo No. | Sequence & Modification |
|---|---|
| SEQ ID NO.: 1   131-1 | 5'-CTATCTGACGTTCTCTGT-3' |
| SEQ ID NO.: 57  167-1 | 5'-CTATCTGXCGTTCTCTGT-3' |
| SEQ ID NO.: 58  167-2 | 5'-CTATCTXACGTTCTCTGT-3' |
| SEQ ID NO.: 59  167-3 | 5'-CTATCXGACGTTCTCTGT-3' |
| SEQ ID NO.: 60  167-4 | 5'-CTATXTGACGTTCTCTGT-3' |
| SEQ ID NO.: 61  167-5 | 5'-CTAXCTGACGTTCTCTGT-3' |
| SEQ ID NO.: 62  167-6 | 5'-CTXXCTGACGTTCTCTGT-3' |
| SEQ ID NO.: 63  167-7 | 5'-CTATCTGACGXTCTCTGT-3' |
| SEQ ID NO.: 64  167-8 | 5'-CTATCTGACGTXCTCTGT-3' |
| SEQ ID NO.: 65  167-9 | 5'-CTATCTGACGTTXTCTGT-3' |
| SEQ ID NO.: 66  167-10 | 5'-CTATCTGACGTTCTCXGT-3' |
| SEQ ID NO.: 67  16711 | 5'-CTATCTGACGTTCTXTGT-3' |
| SEQ ID NO.: 68  167-12 | 5'-CTATCTGACGTTCTXXGT-3' |

FIG. 14A

OLIGODEOXYNUCLEOTIDE PHOSPHOROTHIOATES AND MODIFICATION OF LINKAGES

| Oligo No. | Sequence & Modification |
|---|---|
| SEQ ID NO.: 69  113-1 | 5'-TCCATGACGTTCCTGATGC-3' |
| SEQ ID NO.: 70  23-1 | 5'-TCCATGXCGTTCCTGATGC-3' |
| SEQ ID NO.: 71  23-3 | 5'-TCCAXGACGTTCCTGATGC-3' |
| SEQ ID NO.: 72  29-2 | 5'-TYYATGACGGTCCTGATGC-3' |

Rx = 2'-O-Methylribonucleoside
Ry = 2'-O-Methoxyethoxyribonucleoside

OLIGODEOXYNUCLEOTIDE PHOSPHOROTHIOATES AND MODIFICATION OF LINKAGES

| Oligo No. | Sequence & Modification |
|---|---|
| SEQ ID NO.: 69  113-1 | 5'-TCCATGACGTTCCTGATGC-3' |
| SEQ ID NO.: 70  23-1 | 5'-TCCATGXCGTTCCTGATGC-3' |
| SEQ ID NO.: 71  23-3 | 5'-TCCAXGACGTTCCTGATGC-3' |
| SEQ ID NO.: 72  29-2 | 5'-TYYATGACGGTCCTGATGC-3' |

$R_X$ = 2'-O-Methylribonucleoside
$R_Y$ = 2'-O-Methoxyethoxyribonucleoside

OLIGODEOXYNUCLEOTIDE PHOSPHOROTHIOATES AND MODIFICATION OF LINKAGES

| | Oligo No. | Sequence & Modification |
|---|---|---|
| SEQ ID NO.: 73 | 1 | 5'-GAGAACGCTCGACCTT-3' |
| SEQ ID NO.: 74 | 2 | 5'-GAGAACGCTCGACCTT-3' ———— 5'-GAGAACGCTCGACCTT-3' |
| SEQ ID NO.: 75 | 3 | 3'-TTCCAGCTCGCAAGAG-5' ———— 5'-GAGAACGCTCGACCTT-3' |
| SEQ ID NO.: 76 | 4 | 5'-GAGAACGCTCGACCTT-3' ———— 3'-TTCCAGCTCGCAAGAG-5' |
| SEQ ID NO.: 77 | 5 | 5'-TCTCCCAGCGTGCGCCAT-3' |
| SEQ ID NO.: 78 | 6 | 5'-TCCCAGCGTGCGCCAT-3' ———— 5'-TCCCAGCGTGCGCCAT-3' |
| SEQ ID NO.: 79 | 7 | 3'-TACCGCGTGCGACCCT-5' ———— 5'-TCCCAGCGTGCGCCAT-3' |
| SEQ ID NO.: 80 | 8 | 5'-TCCCAGCGTGCGCCAT-3' ———— 3'-TACCGCGTGCGACCCT-5' |

FIG. 17A

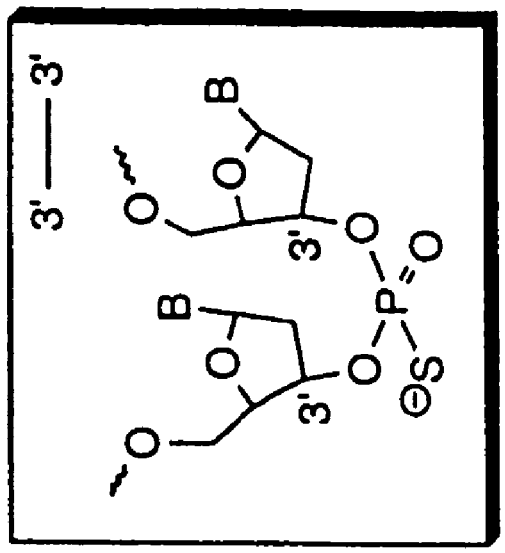
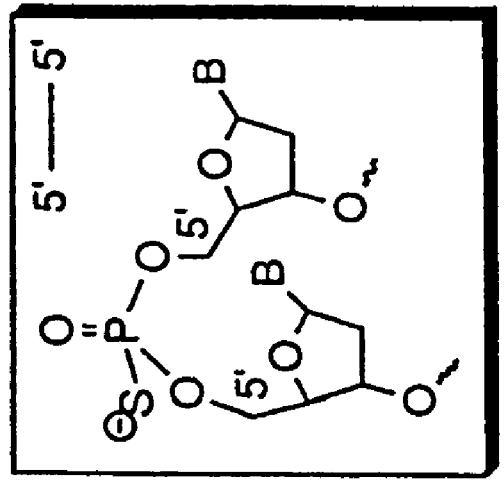
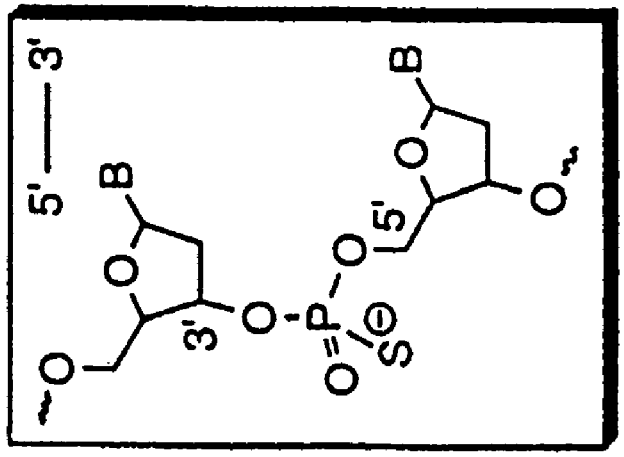
FIG. 17B

OLIGODEOXYNUCLEOTIDE PHOSPHOROTHIOATES AND MODIFICATION OF LINKAGES

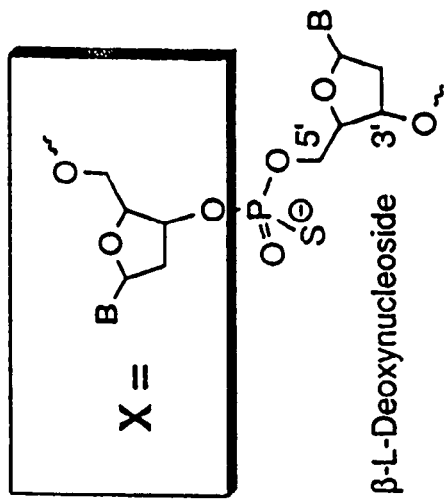

β-L-Deoxynucleoside

| Oligo No. | | Sequence & Modification |
|---|---|---|
| SEQ ID NO.: 1 | 131-1 | 5'-CTATCTGACGTTCTCTGT-3' |
| SEQ ID NO.: 81 | 175-1 | 5'-CTATXTGACGTTCTCTGT-3' |
| SEQ ID NO.: 82 | 175-2 | 5'-CTATCTGACGTTCXCTGT-3' |
| SEQ ID NO.: 83 | 175-3 | 5'-CTAXXTGACGTTCTCTGT-3' |
| SEQ ID NO.: 84 | 175-4 | 5'-CTATCTGACGTTCXXTGT-3' |
| SEQ ID NO.: 85 | 175-5 | 5'-CTATCTGACGTGAXXTTCTCTGT-3' |
| SEQ ID NO.: 86 | 175-6 | 5'-CTATCTXACGTTCTCTGT-3' |
| SEQ ID NO.: 87 | 175-7 | 5'-CTATCTGACGTXCTCTGT-3' |
| SEQ ID NO.: 88 | 175-9 | 5'-CTATCTGACGTTCTCTGT-3' (all-β-L-DNA/PS) |

FIG. 18A

OLIGODEOXYNUCLEOTIDE PHOSPHOROTHIOATES AND MODIFICATION OF LINKAGES

| Oligo No. | Sequence & Modification |
|---|---|
| SEQ ID NO.: 1  131-1 | 5'-CTATCTGACGTTCTCTGT-3' |
| SEQ ID NO.: 89  173-1 | 5'-CTATXTGACGTTCTCTGT-3' |
| SEQ ID NO.: 90  173-2 | 5'-CTATCTGACGTTCTXTGT-3' |

X = [structure of 2'-O-Propargyl-ribonucleoside]

2'-O-Propargyl-ribonucleoside

FIG. 19A

OLIGODEOXYNUCLEOTIDE PHOSPHOROTHIOATES AND MODIFICATION OF LINKAGES

| | Oligo No. | Sequence & Modification |
|---|---|---|
| SEQ ID NO.: 8 | 133-1 | 5'-CCTACTAGCGTTCTCATC-3' |
| SEQ ID NO.: 91 | 143-1 | 5'-CCTXXTAGCGTTCTCATC-3' |
| SEQ ID NO.: 92 | 143-2 | 5'-CCTYYTAGCGTTCTCATC-3' |
| SEQ ID NO.: 93 | 143-3 | 5'-CCTZZTAGCGTTCTCATC-3' |
| SEQ ID NO.: 94 | 143-4 | 5'-CCTXXTAGCGTVCTCATC-3' |
| SEQ ID NO.: 95 | 143-5 | 5'-CCTACTAGGCTTCTCATC-3' |

X = 1',2'-Dideoxyribose
Y = C3-Linker
Z = 3'-OMe
V = 2'-OMe

FIG. 20A

OLIGODEOXYNUCLEOTIDE PHOSPHOROTHIOATES AND
MODIFICATION OF LINKAGES

| | Oligo No. | Sequence & Modification |
|---|---|---|
| SEQ ID NO.: 1 | 1 | 5'-CTATCTGA<u>CG</u>TTCTCTGT-3' (131-1) |
| SEQ ID NO.: 96 | 2 | 5'-CTATCTGA<u>CG</u>*TTCTCTGT-3' (E 633L) |
| SEQ ID NO.: 97 | 3 | 5'-CTATCTGA<u>G</u>*<u>C</u>TTCTCTGT-3' (E 636) |
| SEQ ID NO.: 98 | 4 | 5'-TCTCCCAG<u>CG</u>TG<u>CG</u>CCAT-3' |
| SEQ ID NO.: 99 | 5 | 5'-TCTCCCAG<u>CG</u>*TG<u>CG</u>*CCAT-3' (E 603) |
| SEQ ID NO.: 100 | 6 | 5'-CTATXTGA<u>CG</u>*TTCTCTGT-3' (E 639L) |

FIG. 21A

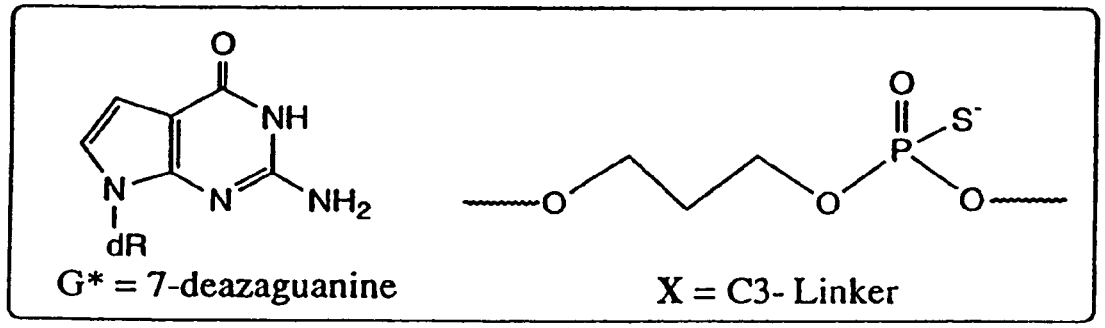

FIG. 21B

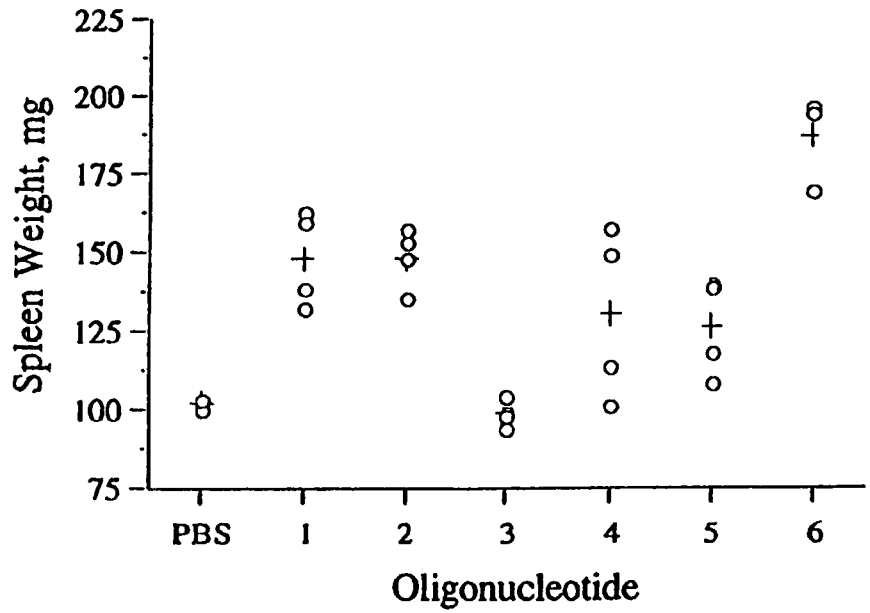

FIG. 21C

OLIGODEOXYNUCLEOTIDE PHOSPHOROTHIOATES AND SITE OF MODIFICATION

| Oligo No. | | Sequence & Modification |
|---|---|---|
| SEQ ID NO.: 1 | 1 | 5'-CTATCTGAC<u>GTT</u>CTCTGT-3' (131-1) |
| SEQ ID NO.: 101 | 2 | 5'-CTATCTGACG*<u>TTCTCTGT</u>-3' (E 682) |
| SEQ ID NO.: 102 | 3 | 5'-CTATCTGAG*<u>CTTCTCTGT</u>-3' (E 683) |

G* = 6-thioguanine

FIG. 22A

OLIGODEOXYNUCLEOTIDE PHOSPHOROTHIOATES AND SITE OF MODIFICATION

| Oligo No. | Sequence & Modification |
|---|---|
| SEQ ID NO.: 1 | 1 | 5'-CTATCTGA<u>CG</u>TTCTCTGT-3' |
| SEQ ID NO.: 2 | 2 | 5'-CTATCTGAC*<u>G</u>TTCTCTGT-3' |
| SEQ ID NO.: 3 | 3 | 5'-CTATCTGA<u>CC</u>*TTCTCTGT-3' |
| SEQ ID NO.: 4 | 4 | 5'-CTATCTGAC**<u>G</u>TTCTCTGT-3' |
| SEQ ID NO.: 5 | 5 | 5'-CTATCTGA<u>CC</u>**TTCTCTGT-3' |

OLIGODEOXYNUCLEOTIDE PHOSPHOROTHIOATES AND SITE OF MODIFICATION

*Oligo No. Sequence & Modification*

SEQ ID NO.: 1  1  5'-CTATCTGA<u>CG</u>TTCTCTGT-3'

SEQ ID NO.: 2  2  5'-CTATCTGA<u>C*G</u>TTCTCTGT-3'

SEQ ID NO.: 3  3  5'-CTATCTGA<u>C*C*</u>TTCTCTGT-3'

SEQ ID NO.: 4  4  5'-CTATCTGA<u>C**G</u>TTCTCTGT-3'

SEQ ID NO.: 5  5  5'-CTATCTGA<u>CC</u>TTCTCTGT-3'

OLIGODEOXYNUCLEOTIDE PHOSPHOROTHIOATES AND SITE OF MODIFICATION

| | Oligo No. | Sequence & Modification |
|---|---|---|
| SEQ ID NO.: 1 | 1 | 5'-CTATCTGA<u>CG</u>TTCTCTGT-3' |
| SEQ ID NO.: 111 | 2 | 5'-CTATCTGAC*<u>G</u>TTCTCTGT-3' |
| SEQ ID NO.: 112 | 3 | 5'-CTATCTGAC<u>C*T</u>TCTCTGT-3' |

OLIGODEOXYNUCLEOTIDE PHOSPHOROTHIOATES AND SITE OF MODIFICATION

| Oligo No. | Sequence & Modification |
|---|---|
| SEQ ID NO.: 1 | 1 5'-CTATCTGACGTTCTCTGT-3' (131-1) |
| SEQ ID NO.: 103 | 2 5'-CTATCTGAC*GTTCTCTGT-3' (E 647) |
| SEQ ID NO.: 104 | 3 5'-CTATXTGAC*GTTCTCTGT-3' (E 653) |

C* = 4-Thiouracil    X = 1,2-Dideoxyribose

MODULATION OF IMMUNOSTIMULATORY ACTIVITY OF IMMUNOSTIMULATORY OLIGONUCLEOTIDE ANALOGS BY POSITIONAL CHEMICAL CHANGES

CROSS REFERENCE TO RELATED APPLICATIONS

This application is a divisional of U.S. patent application Ser. No. 09/965,116, filed on Sep. 26, 2001 (now U.S. Pat. No. 7,262,286), which is a continuation-in-part of U.S. patent application Ser. No. 09/712,898 (now abandoned), filed on Nov. 15, 2000, and which also claims the benefit of U.S. provisional patent application Ser. Nos. 60/235,452 and 60/235,453, both filed on Sep. 26, 2000. Each of the patent applications listed above is hereby incorporated by reference in its entirety.

BACKGROUND OF THE INVENTION

1. Field of the Invention

The invention relates to the therapeutic use of oligonucleotides or oligonucleotide analogs as immunostimulatory agents in immunotherapy applications.

2. Summary of the Related Art

Oligonucleotides have become indispensable tools in modern molecular biology, being used in a wide variety of techniques, ranging from diagnostic probing methods to PCR to antisense inhibition of gene expression and immunotherapy applications. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology, Vol 20: Protocols for Oligonucleotides and Analogs* pp. 165-189 (S. Agrawal, Ed., Humana Press, 1993); *Oligonucleotides and Analogues: A Practical Approach*, pp. 87-108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143-3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22: 1859-1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28: 3539-3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager et al., *Biochemistry* 27: 7237 (1988), discloses synthesis of oligonucleotide phosphoramidates using phosphoramidite chemistry. Agrawal et al., *Proc. Natl. Acad. Sci. USA* 85: 7079-7083 (1988), discloses synthesis of oligonucleotide phosphoramidates and phosphorothioates using H-phosphonate chemistry.

More recently, several researchers have demonstrated the validity of the use of oligonucleotides as immunostimulatory agents in immunotherapy applications. The observation that phosphodiester and phosphorothioate oligonucleotides can induce immune stimulation has created interest in developing this side effect as a therapeutic tool. These efforts have focused on phosphorothioate oligonucleotides containing the dinucleotide CpG.

Kuramoto et al., *Jpn. J. Cancer Res.* 83: 1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371: 546-549 (1995) discloses that phosphorothioate CpG-containing oligonucleotides are immunostimulatory. Liang et al., *J. Clin. Invest.* 98: 1119-1129 (1996) discloses that such oligonucleotides activate human B cells.

Pisetsky, D. S.; Rich C. F., *Life Sci.* 54: 101 (1994), teaches that the immunostimulatory activity of CpG-oligos is further enhanced by the presence of phosphorothioate (PS) backbone on these oligos. Tokunaga, T.; Yamamoto, T.; Yamamoto, S. *Jap. J. Infect. Dis.* 52:1 (1999), teaches that immunostimulatory activity of CpG-oligos is dependent on the position of CpG-motif and the sequences flanking CpG-motif. The mechanism of activation of immune stimulation by CpG-oligos has not been well understood. Yamamoto, T.; Yamamoto, S.; Kataoka, T.; Tokunaga, T., *Microbiol. Immunol.* 38: 831 (1994), however, suggests that CpG-oligos trigger immune cascade by binding to an intracellular receptor/protein, which is not characterized yet.

Several researchers have found that this ultimately triggers stress kinase pathways, activation of NF-κB and induction of various cytokines such as IL-6, IL-12, γ-IFN, and TNF-α. (See e.g., Klinman, D. M.; Yi, A. K.; Beaucage, S. L.; Conover, J.; Krieg, A. M., *Proc. Natl. Acad. Sci. U.S.A.* 93: 2879 (1996); Sparwasser, T.; Miethke, T.; Lipford, G. B.; Erdmann, A.; Haecker, H.; Heeg, K.; Wagner, H., *Eur. J. Immunol.* 27: 1671 (1997); Lipford, G. B.; Sparwasser, T.; Bauer, M.; Zimmermann, S.; Koch, E. S.; Heeg, K.; Wagner, H. *Eur. J., Immunol.* 27:3420 (1997); Sparwasser, T.; Koch, E. S.; Vabulas, R. M.; Lipford, G. B.; Heeg, K.; Ellart, J. W.; Wagner, H., *Eur. J. Immunol.* 28: 2045 (1998); and Zhao, Q.; Temsamani, J.; Zhou, R. Z.; Agrawal, S. *Antisense Nucleic Acid Drug Dev.* 7:495 (1997).)

The use of CpG-PS-oligos as antitumor, antiviral, antibacterial and antiinflammatory agents and as adjuvants in immunotherapy has been reported. (See e.g., Dunford, P. J.; Mulqueen, M. J.; Agrawal, S. *Antisense 97: Targeting the Molecular Basis of Disease*, (Nature Biotechnology) Conference abstract, 1997, pp 40; Agrawal, S.; Kandimalla E. R. *Mol. Med. Today* 6: 72 (2000); Chu. R. S.; Targoni, O. S.; Krieg, A. M.; Lehmann, P. V.; Harding, C. V. *J. Exp. Med.* 186: 1623 (1997); Zimmermann, S.; Egeter, O.; Hausmann, S.; Lipford, G. B.; Rocken, M.; Wagner, H.; Heeg, K. *J. Immunol.* 160: 3627 (1998).) Moldoveanu et al., *Vaccine* 16: 1216-124 (1998) teaches that CpG-containing phosphorothioate oligonucleotides enhance immune response against influenza virus. McCluskie and Davis, *J. Immunol.* 161: 4463-4466 (1998) teaches that CpG-containing oligonucleotides act as potent adjuvants, enhancing immune response against hepatitis B surface antigen.

Zhao, Q.; Temsamani, J.; Idarola, P.; Jiang, Z.; Agrawal, S. *Biochem. Pharmacol.* 51: 173 (1996), teaches that replacement of deoxynucleosides in a CpG-motif with 2'-O-methylribonucleosides suppresses immunostimulatory activity, suggesting that a rigid C3'-endo conformation induced by 2'-O-methyl modification does not allow proper recognition and/or interaction of CpG-motif with the proteins involved in the immunostimulatory pathway. This reference further teaches that substitution of a methyl group for an unbridged oxygen on the phosphate group between C and G of a CpG-motif suppresses immune stimulatory activity, suggesting that negative charge on phosphate group is essential for protein recognition and interaction.

Zhao, Q.; Yu,. D.; Agrawal, S. *Bioorg. Med. Chem. Lett.* 9: 3453 (1999), teaches that substitution of one or two 2'-deoxynucleosides adjacent to CpG-motif with 2'- or 3'-O-methylribonucleosides on the 5'-side causes a decrease in immunostimulatory activity, while the same substitutions have insignificant effect when they were placed on the 3'-side of the CpG-motif. However, Zhao, Q.; Yu, D.; Agrawal, S. *Bioorg. Med. Chem. Lett.* 10: 1051 (2000), teaches that the substitution of a deoxynucleoside two or three nucleosides away from the CpG-motif on the 5'-side with one or two 2'-O-methoxyethyl- or 2'- or 3'-O-methylribonucleosides results in a significant increase in immunostimulatory activity.

The precise structural requirements and specific functional groups of CpG-motif necessary for the recognition of protein/receptor factor that is responsible for immune stimulation have not yet been studied in detail. There is, therefore, a need for new immunostimulatory motifs which may provide improved immunostimulatory activity.

BRIEF SUMMARY OF THE INVENTION

The invention provides methods for enhancing the immune response caused by immunostimulatory oligonucleotide compounds. The methods according to the invention enable increasing the immunostimulatory effect for immunotherapy applications. Thus, the invention further provides methods for making and using such oligonucleotide compounds.

The present inventors have surprisingly discovered that positional modification of immunostimulatory oligonucleotides dramatically affects their immunostimulatory capabilities. In particular, modifications in the immunostimulatory domain and/or the potentiation domain enhance the immunostimulatory effect in a reproducible and predictable manner.

In a first aspect, the invention provides immunostimulatory oligonucleotide compounds comprising an immunostimulatory domain and, optionally, one or more potentiation domains. In some embodiments, the immunostimulatory domain comprises a dinucleotide analog that includes a non-naturally occurring pyrimidine base. In some embodiments, the immunostimulatory domain and/or the potentiation domain include an immunostimulatory moiety at a specified position, as described hereinbelow. In some embodiments, the immunostimulatory oligonucleotide comprises a 3'-3' linkage. In one embodiment, such 3'-3' linked oligonucleotides have two accessible 5'-ends.

In a second aspect, the invention provides methods for modulating the immunostimulatory effect of an immunostimulatory oligonucleotide compound. In some embodiments, the method comprises introducing into the immunostimulatory domain a dinucleotide analog that includes a non-naturally occurring pyrimidine base. In some embodiments, the method comprises introducing into the immunostimulatory domain and/or potentiation domain an immunostimulatory moiety at a specified position, as described hereinbelow. In some embodiments, the method comprises introducing into the oligonucleotide a 3'-3' linkage.

In a third aspect, the invention provides methods for generating an immune response in a patient, such methods comprising administering to the patient an immunostimulatory oligonucleotide compound according to the invention.

In a fourth aspect, the invention provides methods for therapeutically treating a patient having disease caused by a pathogen, such methods comprising administering to the patient an immunostimulatory oligonucleotide compound according to the invention.

In a fifth aspect, the invention provides methods for treating a cancer patient, such methods comprising administering to the patient an immunostimulatory oligonucleotide compound according to the invention.

In a sixth aspect, the invention provides methods for treating autoimmune disorders, such as autoimmune asthma, such methods comprising administering to the patient an oligonucleotide analog immunostimulatory compound according to the invention. Administration is carried out as described for the third aspect of the invention.

In a seventh aspect, the invention provides methods for treating airway inflammation or allergies, such methods comprising administering to the patient an oligonucleotide analog immunostimulatory compound according to the invention. Administration is carried out as described for the third aspect of the invention.

BRIEF DESCRIPTION OF THE FIGURES

FIGS. 1A-1B shows results of proliferation assays using oligonucleotides (SEQ ID NOs:8-23) having 1',2'-dideoxyribose substitutions at various positions.

FIGS. 2A-2B shows results of spleen weight assays using oligonucleotides (SEQ ID NOs:8-23) having 1',2'-dideoxyribose substitutions at various positions.

FIGS. 5A-5B shows results of proliferation assays using oligonucleotides (SEQ ID NOs:1, 8, 24-34) having C3-linker substitutions at various positions.

FIGS. 6A-6B shows results of spleen weight assays using oligonucleotides (SEQ ID NOs:1, 8, 24-34) having C3-linker substitutions at various positions.

FIGS. 7A-7B shows results of proliferation assays using oligonucleotides (SEQ ID NOs:1, 8, 35-42) having Spacer 9 or Spacer 18 substitutions at various positions.

FIGS. 8A-8B shows results of spleen weight assays using oligonucleotides (SEQ ID NOs: 1, 8, 35-42) having Spacer 9 or Spacer 18 substitutions at various positions.

FIGS. 11A-11B shows results of proliferation assays using oligonucleotides (SEQ ID Nos:1, 8, 48-56) having 3'-deoxynucleoside substitutions at various positions.

FIGS. 12A-12B shows results of spleen weight assays using oligonucleotides (SEQ ID NOs:1, 8, 48-56) having 3'-deoxynucleoside substitution at various positions.

FIGS. 13A-13B shows results of proliferation assays using oligonucleotides (SEQ ID NOs: 1, 57-68) having methylphosphonate substitutions at various positions.

FIGS. 14A-14B shows results of spleen weight assays using oligonucleotides (SEQ ID NOs:1, 57-68) having methylphosphonate substitutions at various positions.

FIGS. 18A-18B shows results of spleen weight assays using oligonucleotides (SEQ ID NOs:1, 81-88) having β-L-deoxynucleotide substitutions at various positions.

FIGS. 19A-19B shows results of spleen weight assays using oligonucleotides (SEQ ID NOs:1, 89-90) having 2'-O-propargyl substitutions at various positions.

FIGS. 20A-20B shows results of spleen weight assays using oligonucleotides (SEQ ID NOs:8 91-95) having various substitution at various positions.

FIGS. 21A-21C shows results of spleen weight assays using oligonucleotides (SEQ ID NOs:1, 96-100) having 7-deazaguanine substitution within the immunostimulatory dinucleotide.

FIGS. 22A-22B shows results of proliferation assays using oligonucleotides (SEQ ID NOs:1, 101, 102) having 6-thioguanine substitution within the immunostimulatory dinucleotide.

DETAILED DESCRIPTION

Figure 1B:
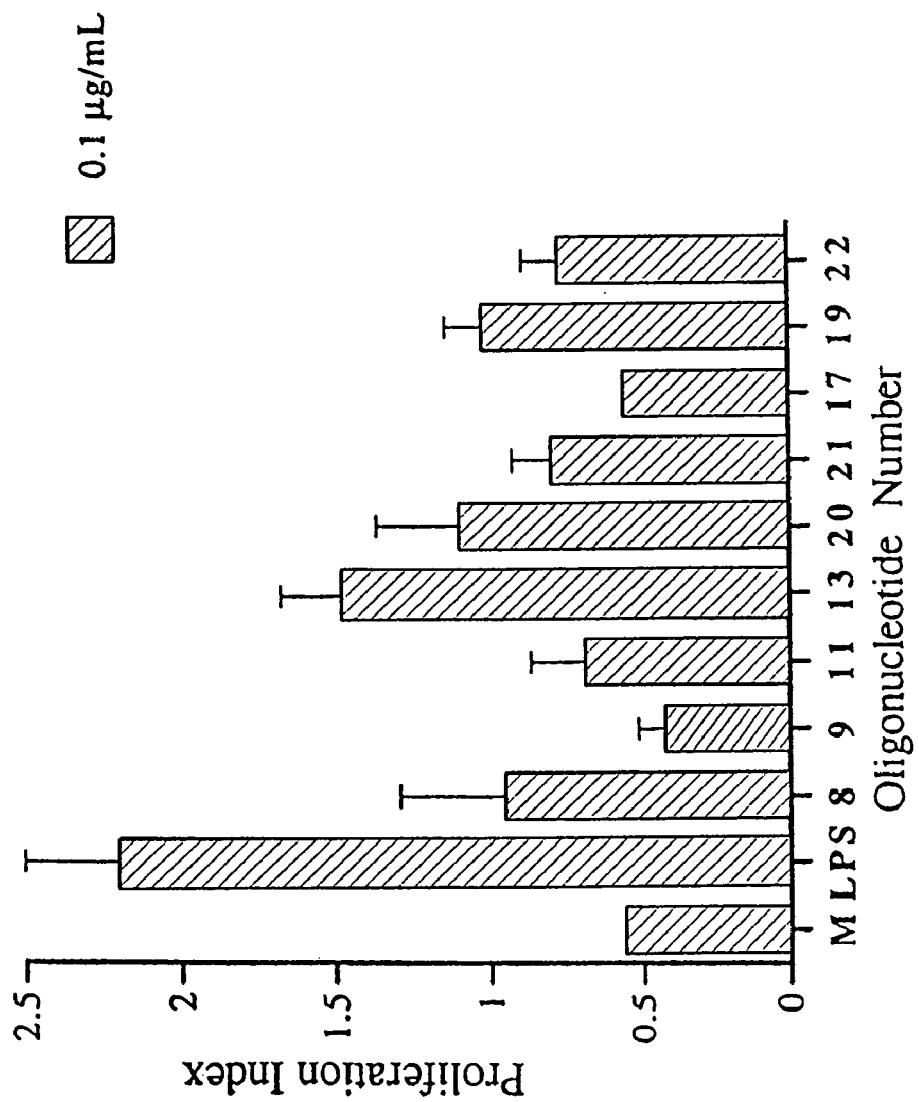
Figure 2B:
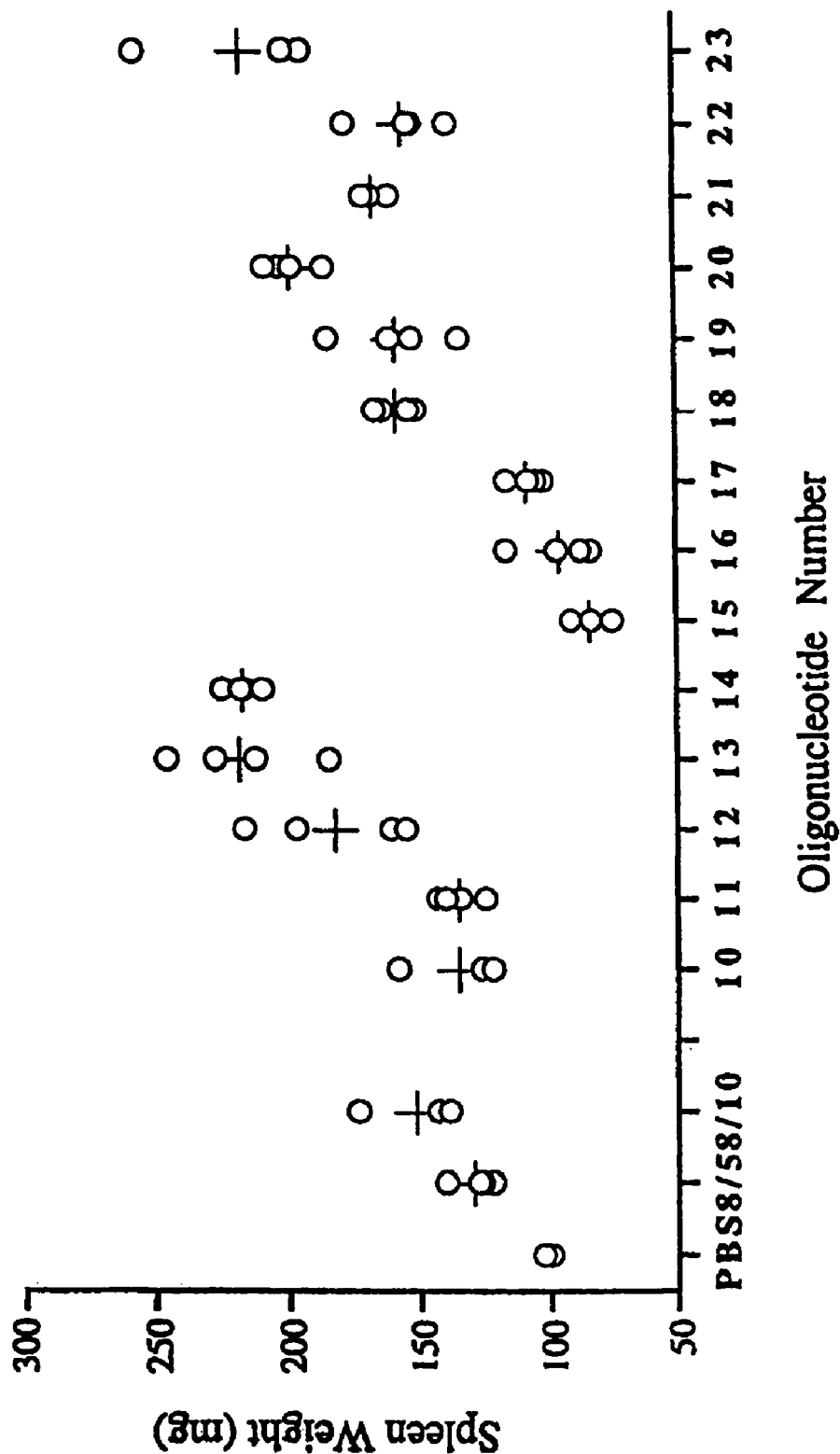
Figure 3A:
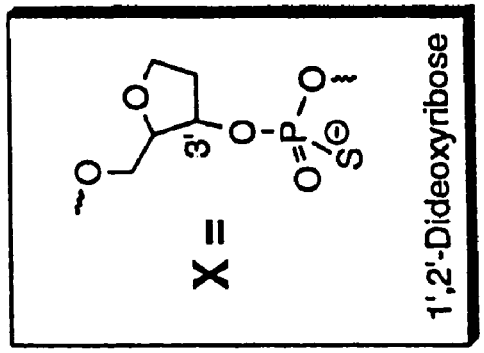
FIGS. 3A-3B shows results of proliferation assays using difference oligonucleotides (SEQ ID NOs:1, 105-110) having 1',2'-dideoxyribose substitutions at various positions.
Figure 3B:
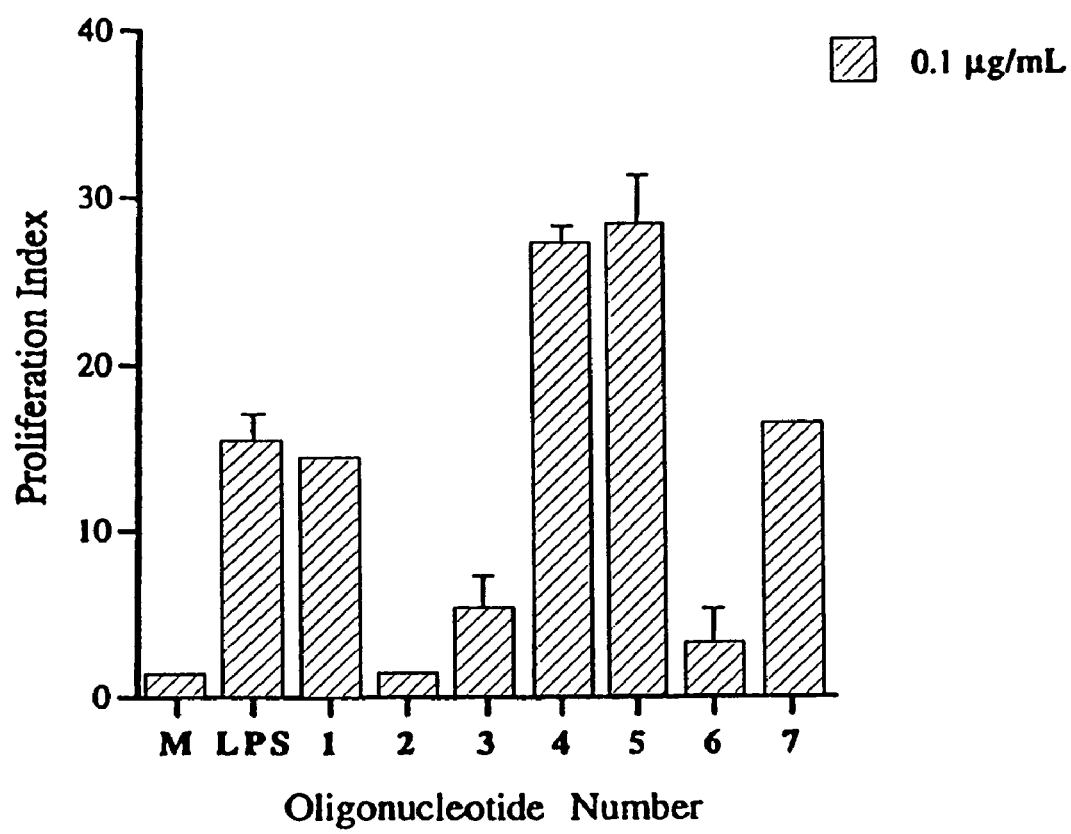
Figure 4A:
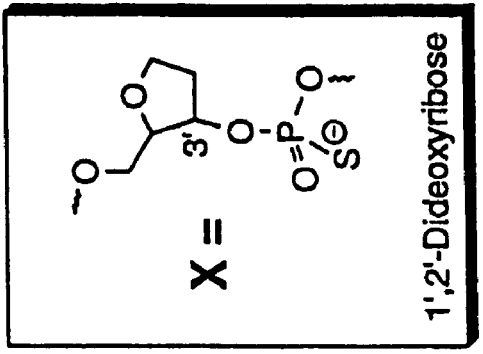
FIGS. 4A-4B shows results of spleen weight assays using different oligonucleotides (SEQ ID NOs:1, 105-110) having 1',2'-dideoxyribose substitutions at various positions.
Figure 4B:
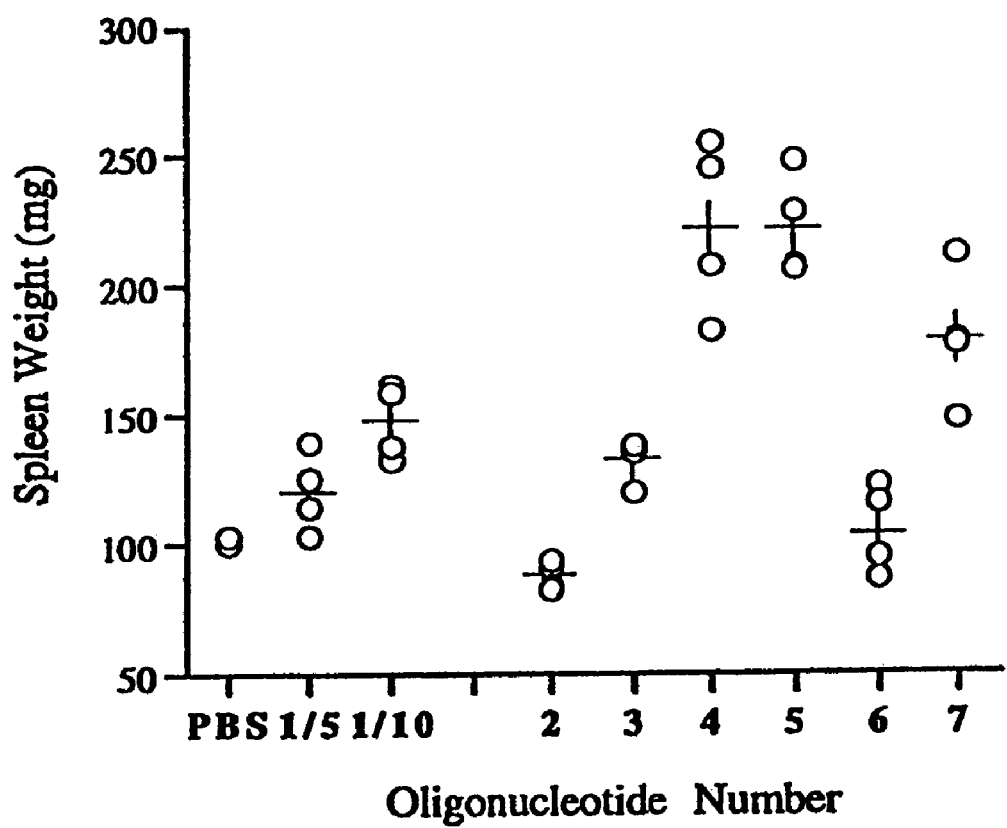
Figure 5B:
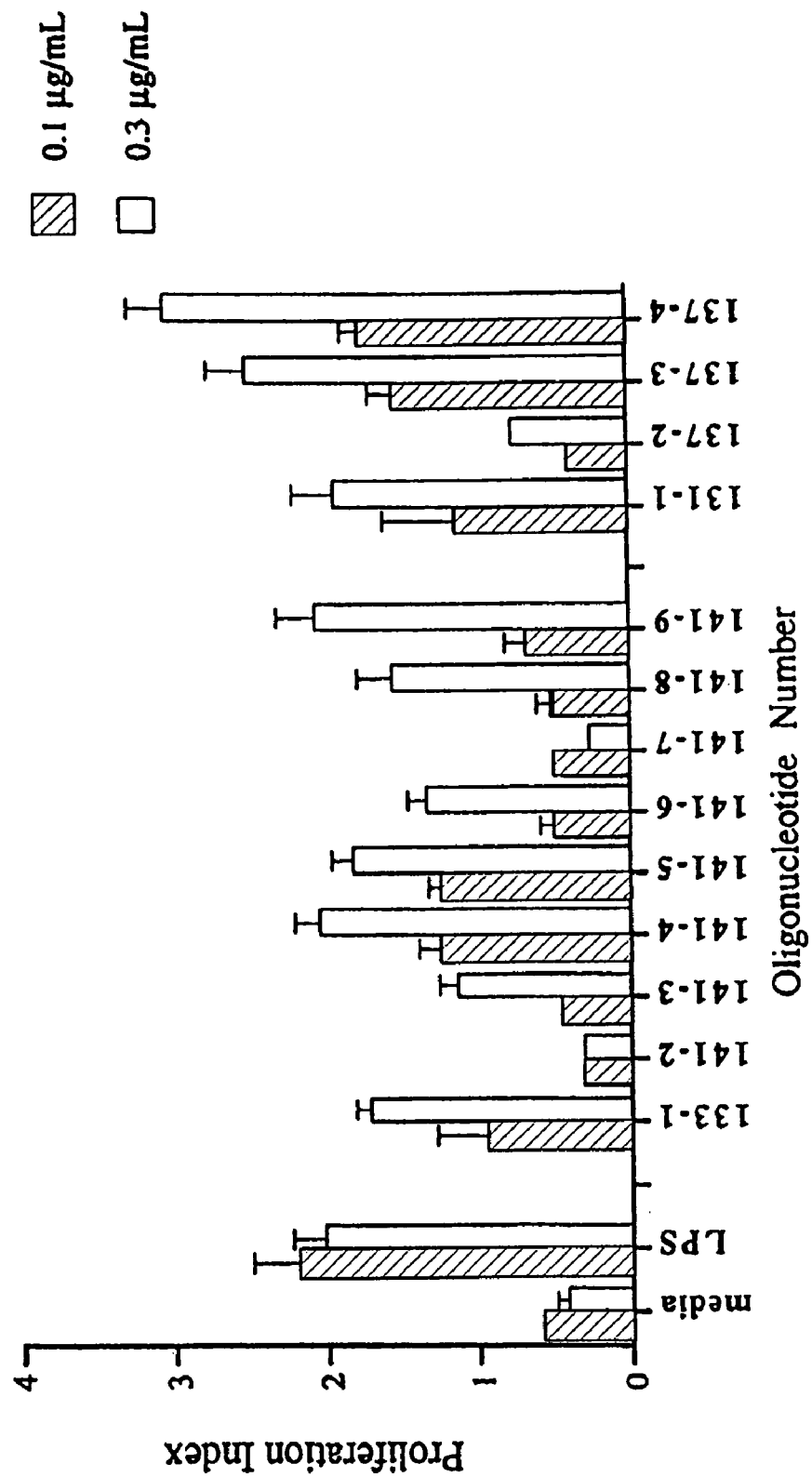
Figure 6B:
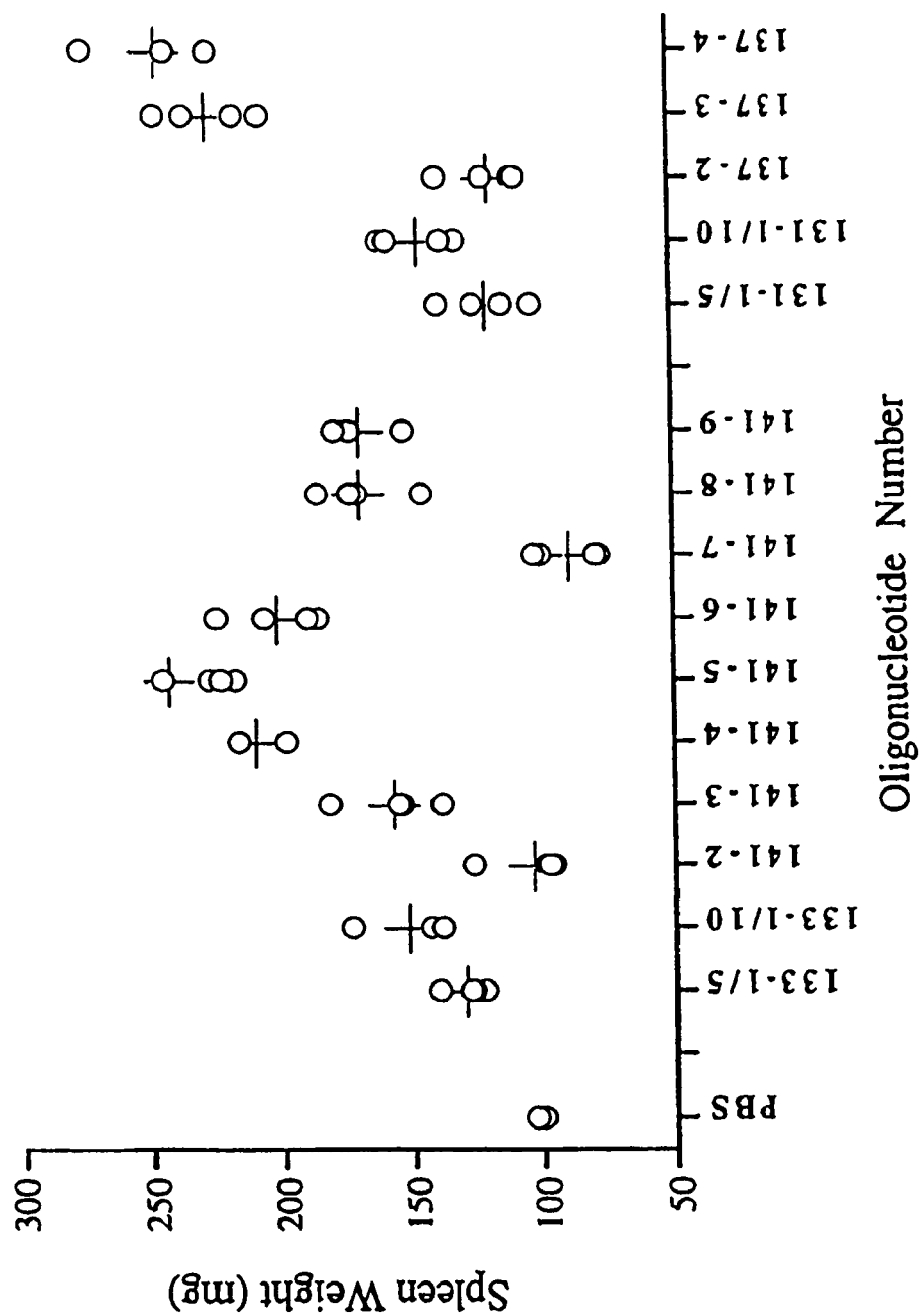

The invention relates to the therapeutic use of oligonucleotides and oligonucleotide analogs as immunostimulatory agents for immunotherapy applications. The patents and publications cited herein reflect the level of knowledge in the field and are hereby incorporated by reference in their entirety. In the event of conflict between any teaching of any reference cited herein and the present specification, the latter shall prevail, for purposes of the invention.

The invention provides methods for enhancing the immune response caused by immunostimulatory oligonucleotide compounds for immunotherapy applications. Thus, the invention further provides compounds having optimal levels of immunostimulatory effect for immunotherapy and methods for making and using such oligonucleotide compounds.

The present inventors have surprisingly discovered that positional chemical modifications introduced in immunostimulatory oligonucleotides dramatically affect their immunostimulatory capabilities. In particular, modifications in the immunostimulatory domain and/or the potentiation domain can enhance the immunostimulatory effect in a reproducible manner for desired applications.

In a first aspect, the invention provides immunostimulatory oligonucleotide compounds comprising an immunostimulatory domain and, optionally, one or more potentiation domains. In certain preferred embodiments, the immunostimulatory domain comprises a dinucleotide analog that includes a non-natural pyrimidine nucleoside.

For purposes of all aspects of the invention, the term "oligonucleotide" includes polymers of two or more deoxyribonucleosides, or any modified nucleoside, including 2'- or 3'-substituted nucleosides, 2'- or 3'-O-substituted ribonucleosides, deazanucleosides, or any combination thereof. Such monomers may be coupled to each other by any of the numerous known internucleoside linkages. In certain preferred embodiments, these internucleoside linkages may be phosphodiester, phosphotriester, phosphorothioate, phosphorodithioate, or phosphoramidate linkages, including 3'-5',2'-5', 3'-3', and 5'-5' linkages of any of the foregoing, or combinations thereof. The term oligonucleotide also encompasses such polymers having chemically modified bases or sugars and/or having additional substituents, including without limitation lipophilic groups, intercalating agents, diamines and adamantane. The term oligonucleotide also encompasses peptide nucleic acids (PNA), peptide nucleic acids with phosphate groups (PHONA), locked nucleic acids (LNA), morpholinonucleic acids, and oligonucleotides comprising non-pentose sugar (e.g. hexose) or abasic sugar backbones or backbone sections, as well as oligonucleotides that include backbone sections with non-sugar linker or spacer groups, as further described hereinbelow.

For purposes of the invention the terms "2'-substituted" and "3'-substituted" mean (respectively) substitution of the 2' (or 3') position of the pentose moiety with a halogen (preferably Cl, Br, or F), or an —O-lower alkyl group containing 1-6 saturated or unsaturated carbon atoms, or with an —O-aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxy, or amino groups; or such 2' substitution may be with a hydroxy group (to produce a ribonucleoside) or an amino group, but not with a 2' (or 3') H group.

For purposes of the invention, the term "immunostimulatory oligonucleotide compound" means a compound comprising an immunostimulatory dinucleotide, without which the compound would not have an immunostimulatory effect. An "immunostimulatory dinucleotide" is a dinucleotide having the formula 5'-pyrimidine-purine-3', wherein "pyrimidine" is a natural or non-natural pyrimidine nucleoside and "purine" is a natural or non-natural purine nucleoside. One such immunostimulatory dinucleotide is CpG. The terms "CpG" and "CpG dinucleotide" refer to the dinucleotide 5'-deoxycytidine-deoxyguanosine-3', wherein p is an internucleotide linkage, preferably selected from the group consisting of phosphodiester, phosphorothioate, and phosphorodithioate.

For purposes of the invention, a "dinucleotide analog" is an immunostimulatory dinucleotide as described above, wherein either or both of the pyrimidine and purine nucleosides is a non-natural nucleoside. A "non-natural" nucleoside is one that includes a non-naturally occurring base and/or a non-naturally occurring sugar moiety. For purposes of the invention, a base is considered to be non-natural if it is not selected from the group consisting of thymine, guanine, cytosine, adenine, and uracil. The terms "C*pG" and "CpG*" refer to immunostimulatory dinucleotide analogs comprising a cytidine analog (non-natural pyrimidine nucleoside) or a guanosine analog (non-natural purine nucleoside), respectively.

Figure 27:
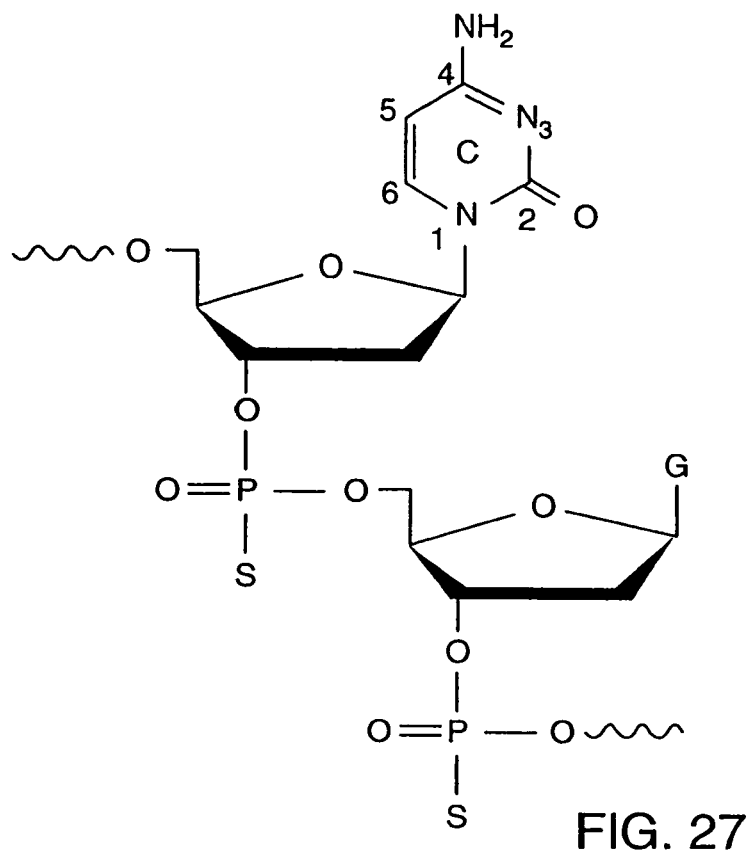
FIG. 27 shows the chemical structure of a CpG-motif, showing functional groups on cytosine that serve as hydrogen bond acceptor and hydrogen bond donor groups.
Figure 28:
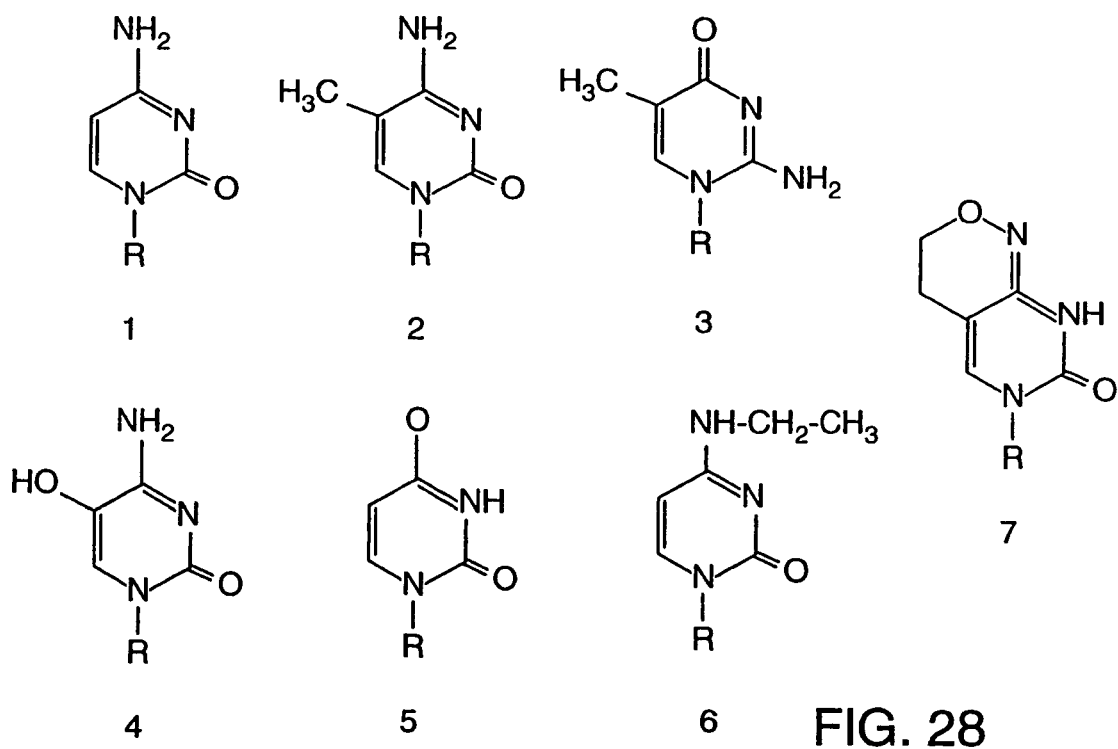
FIG. 28 shows the chemical structures of cytosine (1) and cytosine analogs (2-7). In the nucleosides cytidine, deoxycytidine, and related analogs, the substituent R is ribose or 2'-deoxyribose.

FIG. 27 shows the chemical structure of a CpG-motif, showing the functional groups on cytosine that serve as hydrogen bond acceptor and hydrogen bond donor groups. Cytosine has two hydrogen bond acceptor groups at positions 2 (keto-oxygen) and 3 (nitrogen), and a hydrogen bond donor group at the 4-position (amino group) These groups can serve as potential recognizing and interacting groups with receptors that are responsible for immune stimulation. FIG. 28 shows cytosine analogs that are isostructural with natural cytosine, including 5-methyl-deoxycytosine (2), 5-methyl-deoxyisocytosine (3), 5-hydroxy-deoxycytosine (4), deoxyuridine (5), N4-ethyl-deoxycytosine (6), and deoxy-P-base (7).

In one embodiment, therefore, the immunostimulatory dinucleotide comprises a pyrimidine nucleoside of structure (I):

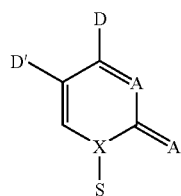

wherein D is a hydrogen bond donor, D' is selected from the group consisting of hydrogen, hydrogen bond donor, hydrogen bond acceptor, hydrophilic group, hydrophobic group, electron withdrawing group and electron donating group, A is a hydrogen bond acceptor, X is carbon or nitrogen, and S is a pentose or hexose sugar ring linked to the pyrimidine base. In some embodiments, the pyrimidine nucleoside is a non-natural pyrimidine nucleoside, i.e., the compound of structure (I) is not cytidine or deoxycytidine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. In some embodiments, the sugar moiety S in (I) is a non-naturally occurring sugar moiety. For purposes of the present invention, a "naturally occurring sugar moiety" is ribose or 2'-deoxyribose, and a "non-naturally occurring sugar moiety" is any sugar other than ribose or 2'-deoxyribose that can be used in the backbone for an oligonucleotide. Arabinose and arabinose derivatives are examples of a preferred non-naturally occurring sugar moieties.

Immunostimulatory domains according to the invention may include immunostimulatory moieties on one or both sides of the immunostimulatory natural dinucleotide or non-natural dinucleotide analog. For example, an immunostimulatory domain could be depicted as

5'-X1-X2-Y—Z—X3-X4-3' wherein Y represents cytidine or a non-natural pyrimidine nucleoside analog, Z represents guanosine or a non-natural purine nucleoside analog, and each X independently represents a nucleoside or an immunostimulatory moiety according to the invention. An "immunostimulatory moiety" is a chemical structure at a particular position within the immunostimulatory domain or the potentiation domain that causes the immunostimulatory oligonucleotide to be more immunostimulatory than it would be in the absence of the immunostimulatory moiety.

Preferred immunostimulatory moieties include modifications in the phosphate backbones including without limitation methylphosphonates, methylphosphonothioates phosphotriesters, phosphothiotriesters phosphorothioates, phosphorodithioates, triester prodrugs, sulfones, sulfonamides, sulfamates, formacetal, N-methylhydroxylamine, carbonate, carbamate, boranophosphonate, phosphoramidates, especially primary amino-phosphoramidates, N3 phosphoramidates and N5 phosphoramidates, and stereospecific linkages (e.g., (R)- or (S)-phosphorothioate, alkylphosphonate, or phosphotriester linkages). Preferred immunostimulatory moieties according to the invention further include nucleosides having sugar modifications, including without limitation 2'-substituted pentose sugars including without limitation 2'-O-methylribose, 2'-O-methoxyethylribose, 2'-O-propargylribose, and 2'-deoxy-2'-fluororibose; 3'-substituted pentose sugars, including without limitation 3'-O-methylribose; 1',2'-dideoxyribose; hexose sugars, including without limitation arabinose, 1'-methylarabinose, 3'-hydroxymethylarabinose, 4'-hydroxymethylarabinose, and 2'-substituted arabinose sugars; and alpha-anomers.

Preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholinonucleic acids, and oligonucleotides having backbone sections with alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Such alkyl linkers include polyethyleneglycol linkers [—O—CH2—CH2-]$_n$ (n=2-9). In some preferred embodiments, such alkyl linkers may include peptides or amino acids.

Preferred immunostimulatory moieties according to the invention further include DNA isoforms, including without limitation β-L-deoxynucleosides and alpha-deoxynucleosides. Preferred immunostimulatory moieties according to the invention further include nucleosides having unnatural internucleoside linkage positions, including without limitation 2'-5', 2'-2', 3'-3' and 5'-5' linkages.

Preferred immunostimulatory moieties according to the invention further include nucleosides having modified heterocyclic bases, including without limitation 5-hydroxydeoxycytidine, 5-hydroxymethyldeoxycytidine, N4-alkyldeoxycytidine, preferably N4-ethyldeoxycytidine, 4-thiouridine, 6-thiodeoxyguanosine, 7-deaza-guanosine, and deoxyribonucleosides of nitropyrrole, C5-propynylpyrimidine, and diaminopurine, including without limitation 2,6-diaminopurine.

By way of specific illustration and not by way of limitation, for example, in the immunostimulatory domain described earlier

5'-X1-X2-Y—Z—X3-X4-3' a nucleoside methylphosphonate at position X3 or X4 is an immunostimulatory moiety, a substituted or unsubstituted alkyl linker at position X1 is an immunostimulatory moiety, and a β-L-deoxynucleoside at position X1 is an immunostimulatory moiety. See Table 1 below for representative positions and structures of immunostimulatory moieties within the immunostimulatory domain.

TABLE 1

| Position | TYPICAL IMMUNOSTIMULATORY MOIETIES |
|---|---|
| X1 | C3-alkyl linker, 2-aminobutyl-1,3-propanediol linker (amino linker), β-L-deoxynucleoside |
| X2 | 2-aminobutyl-1,3-propanediol linker |
| X3 | nucleoside methylphosphonate |
| X4 | nucleoside methylphosphonate, 2'-O-methyl-ribonucleoside |

In some embodiments, the immunostimulatory oligonucleotide further comprises a potentiation domain A "potentiation domain" is a region of an immunostimulatory oligonucleotide analog, other than the immunostimulatory domain, that causes the oligonucleotide to be more immunostimulatory if it contains the potentiation domain than the oligonucleotide would be in the absence of the potentiation domain. The potentiation domain can be upstream or downstream relative to the immunostimulatory domain. The term "upstream" is used to refer to positions on the 5' side of the immunostimulatory dinucleotide or dinucleotide analog (Y-Z). The term "downstream" is used to refer to positions on the 3' side of Y-Z.

For example, an immunostimulatory oligonucleotide analog could have the structure

5'-U9-U8-U7-U6-U5-U4-U3-U2-U1-X1-X2-Y—Z—X3-X4-N—N—N-3' wherein U9-U1 represents an upstream potentiation domain, wherein each U independently represents the same or a different nucleoside immunostimulatory moiety, N represents any nucleoside and X1-X4, Y and Z are as before.

Alternatively, an immunostimulatory oligonucleotide analog could have the structure

5'-N—N—X1-X2-Y—Z—X3-X4-D1-D2-D3-D4-D5-D6-D7-D8-3' wherein D1-D8 represents a downstream potentiation domain, wherein each D independently represents the same or a different nucleoside or immunostimulatory moiety, and all other symbols are as described above.

In these configurations, an immunostimulatory moiety at U6 would be six positions upstream from the immunostimulatory dinucleotide or dinucleotide analog and an immunostimulatory moiety at D4 would be four positions downstream from the immunostimulatory dinucleotide or dinucleotide analog. The term "position" is used rather than "nucleoside", because any of the U or D positions can represent an immunostimulatory moiety which may or may not be a nucleoside or nucleoside analog. Of course, oligonucleotide analogs can be constructed having both upstream and downstream potentiation domains.

Figure 7B:
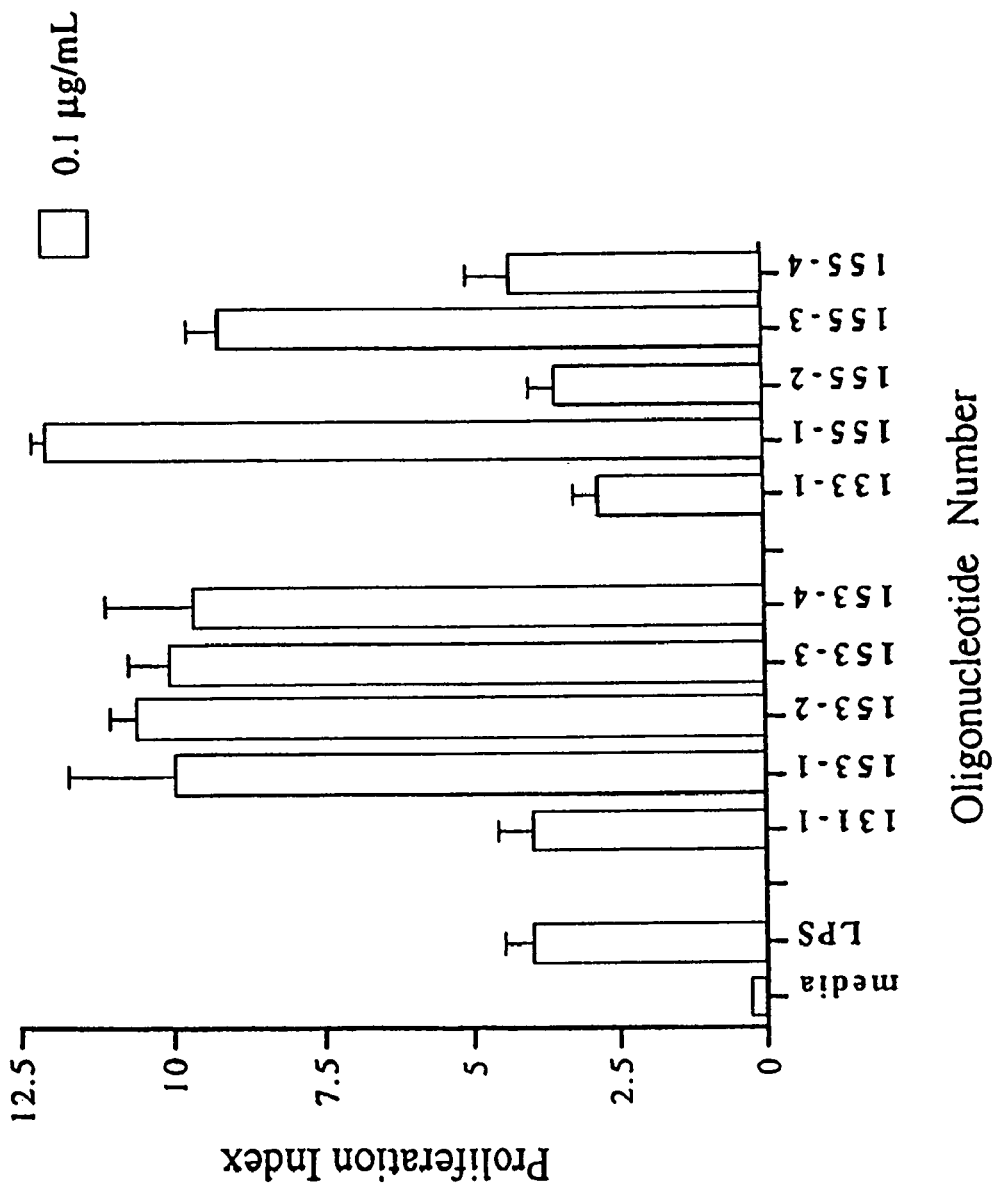
Figure 8B:
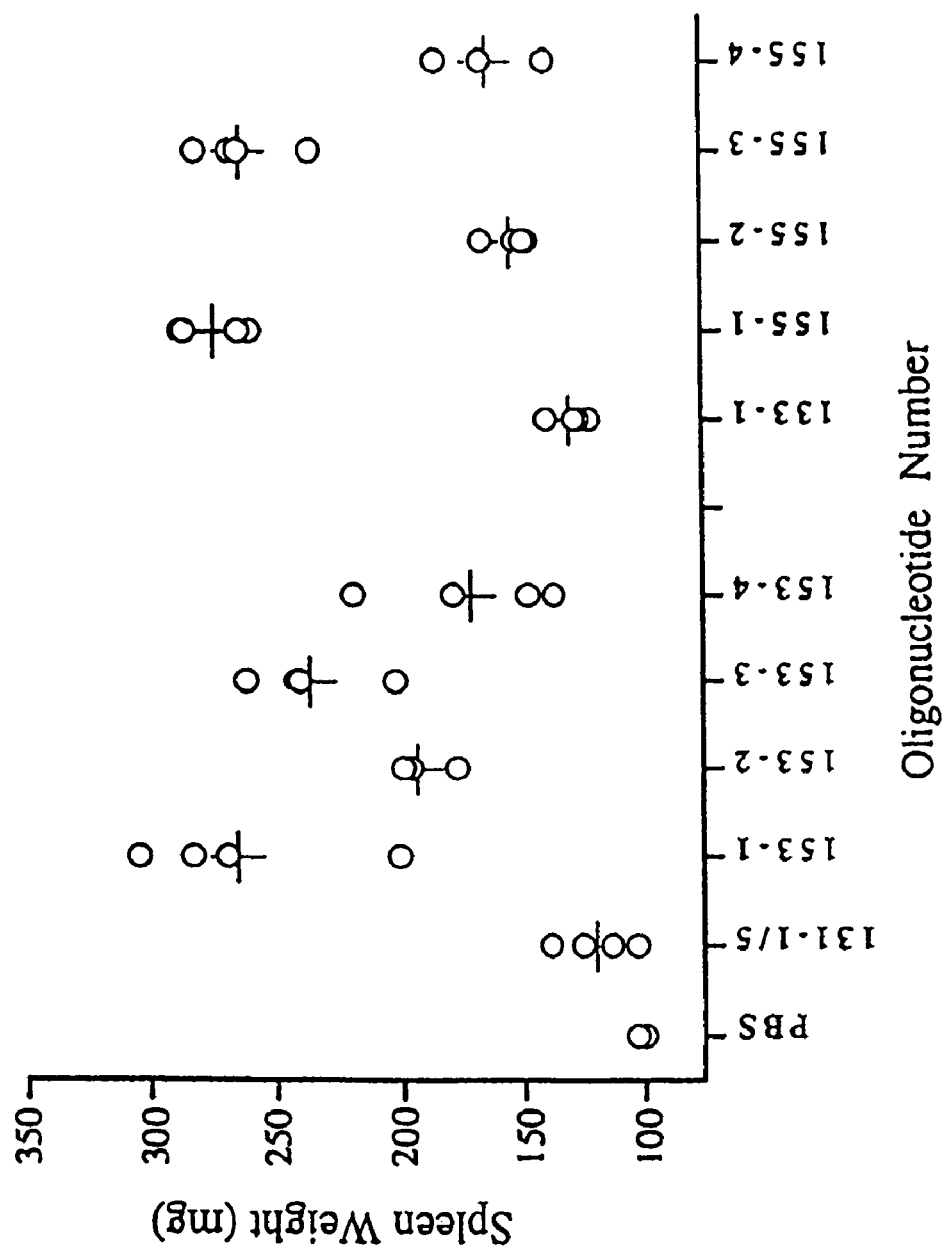
Figure 9A:
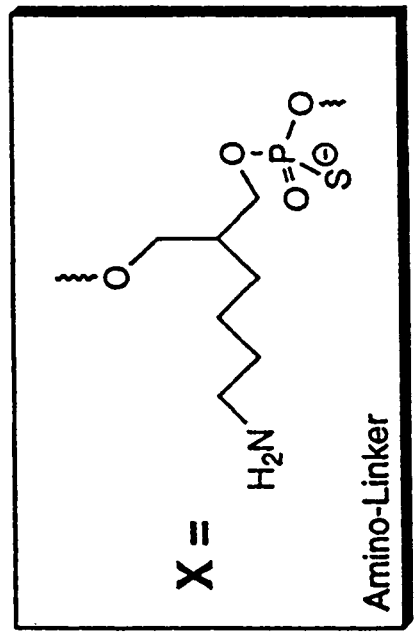
FIGS. 9A-9B shows results of proliferation assays using oligonucleotides (SEQ ID NOs:1, 43-47) having amino-linker substitutions at various positions.
Figure 9B:
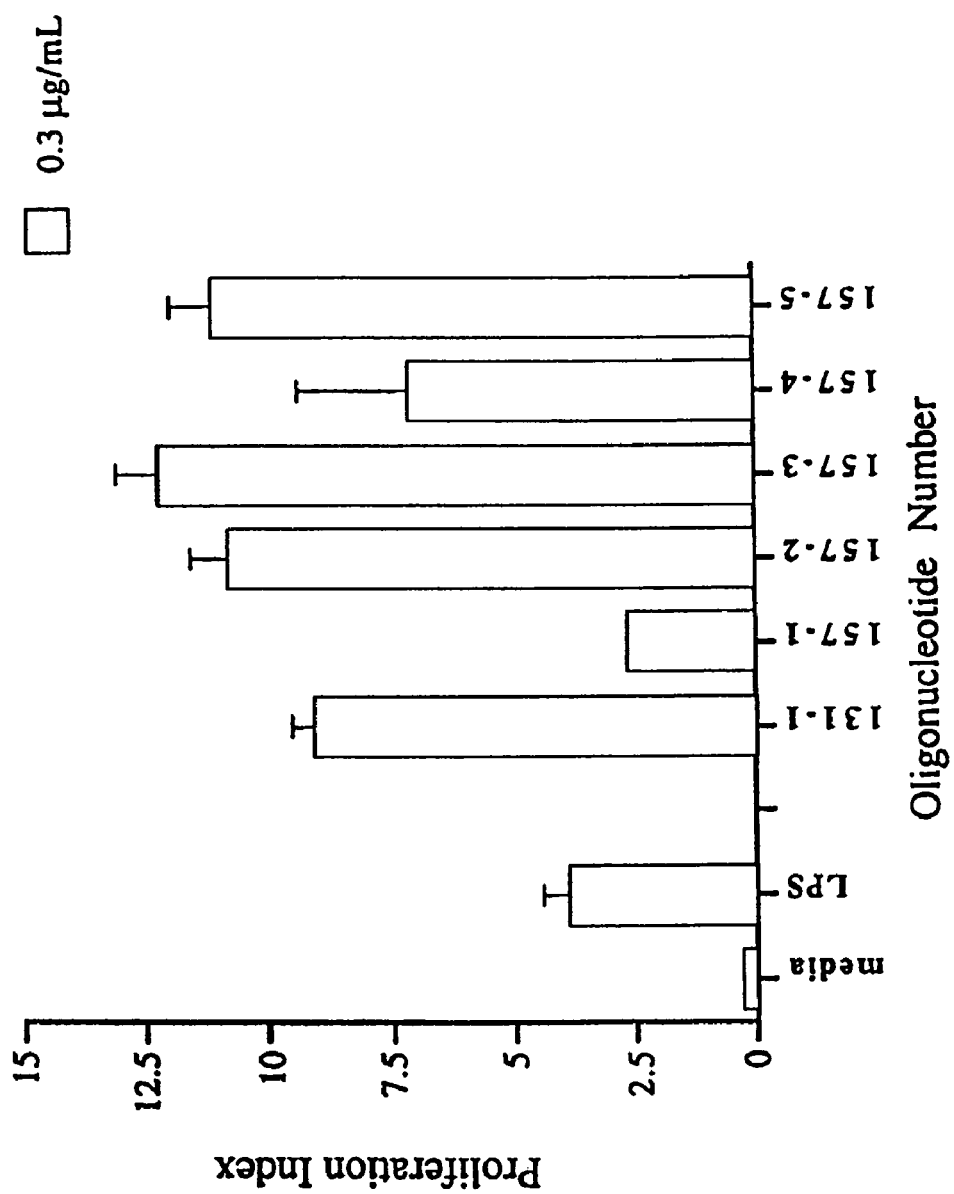
Figure 10A:
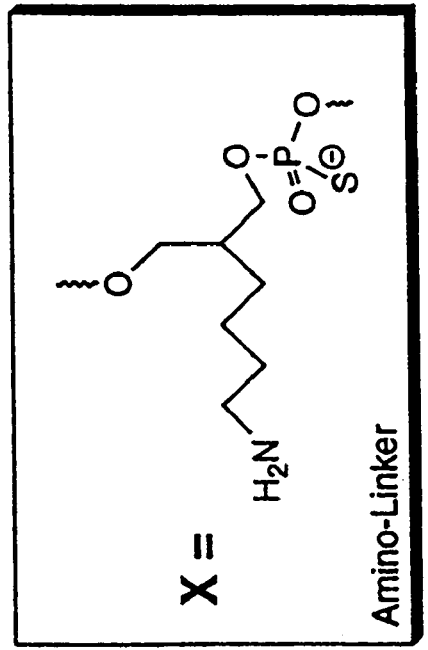
FIGS. 10A-10B shows results of spleen weight assays using oligonucleotides (SEQ ID NOs:1, 43-47) having amino-linker substitutions at various positions.
Figure 10B:
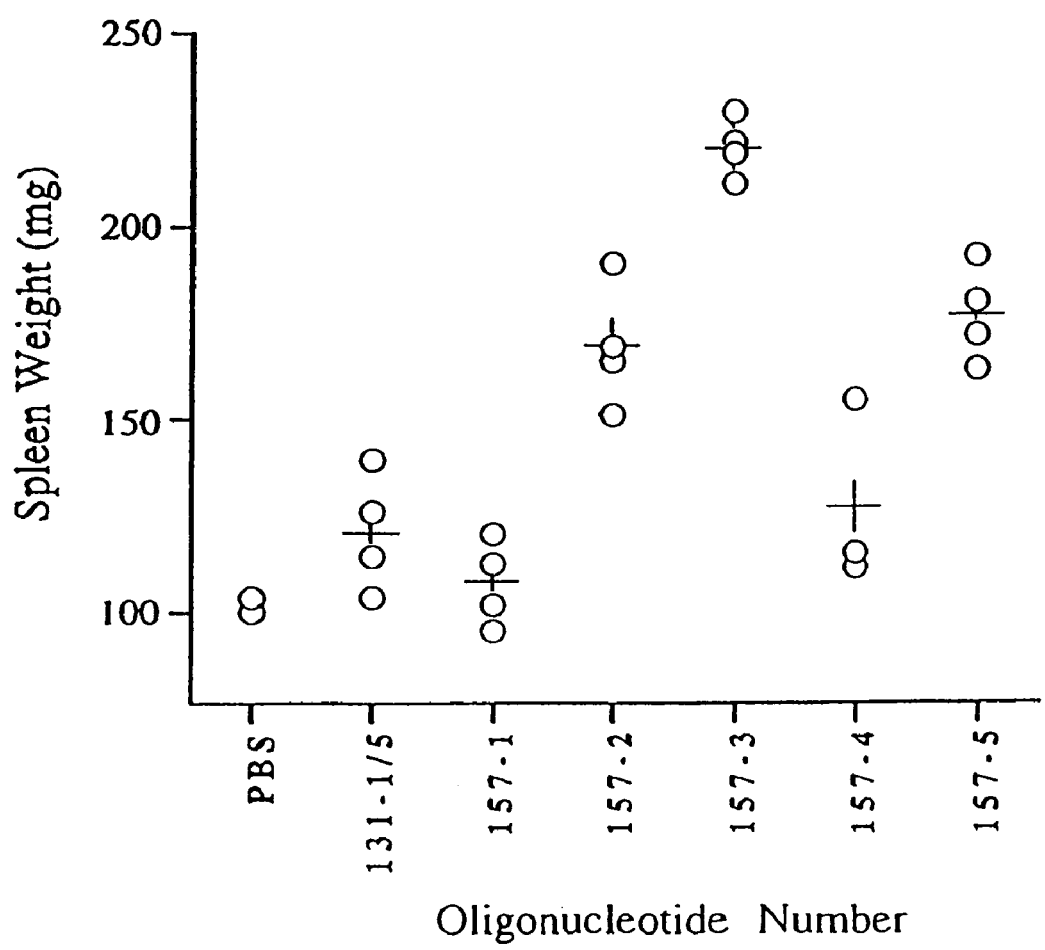
Figure 11B:
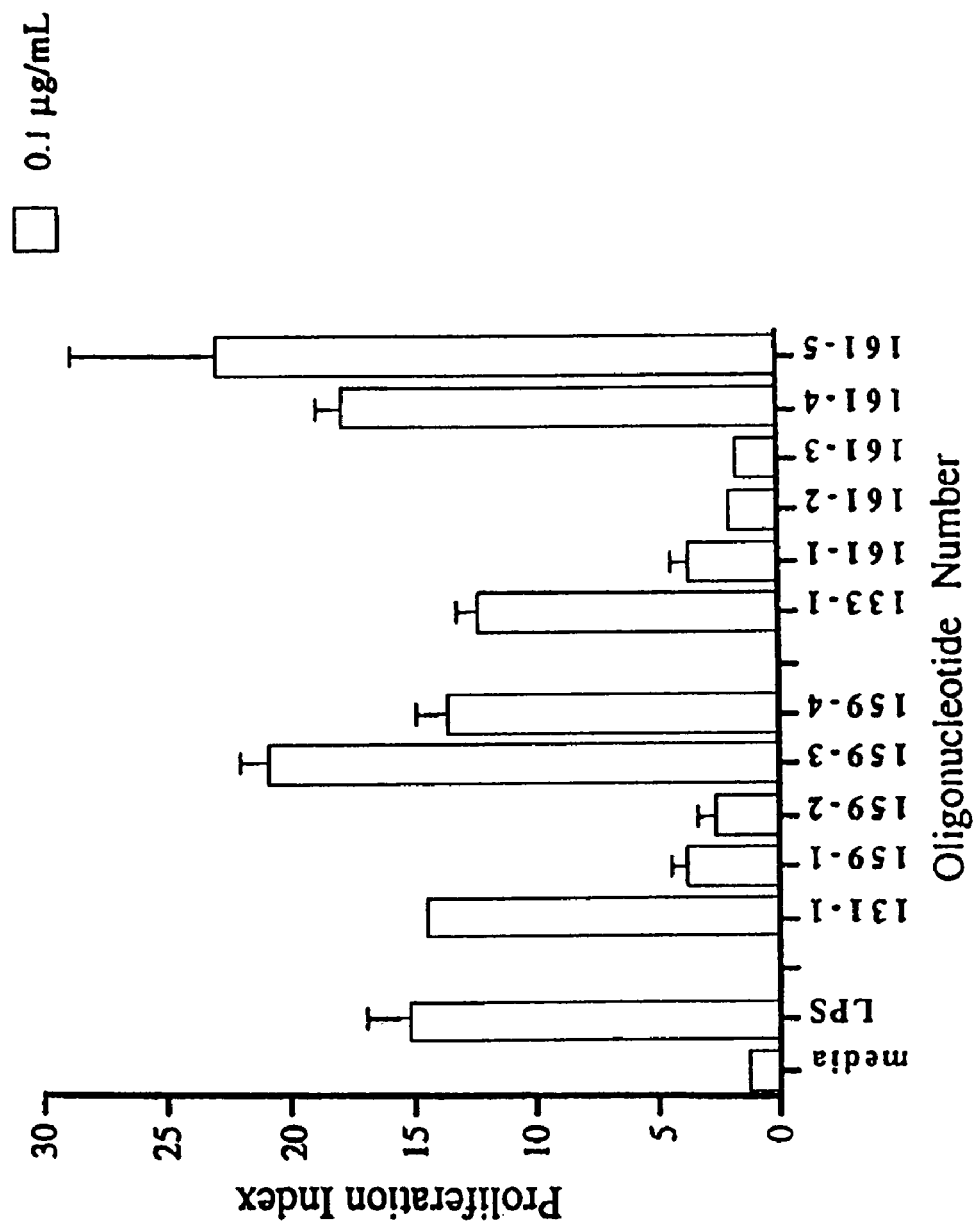
Figure 12B:
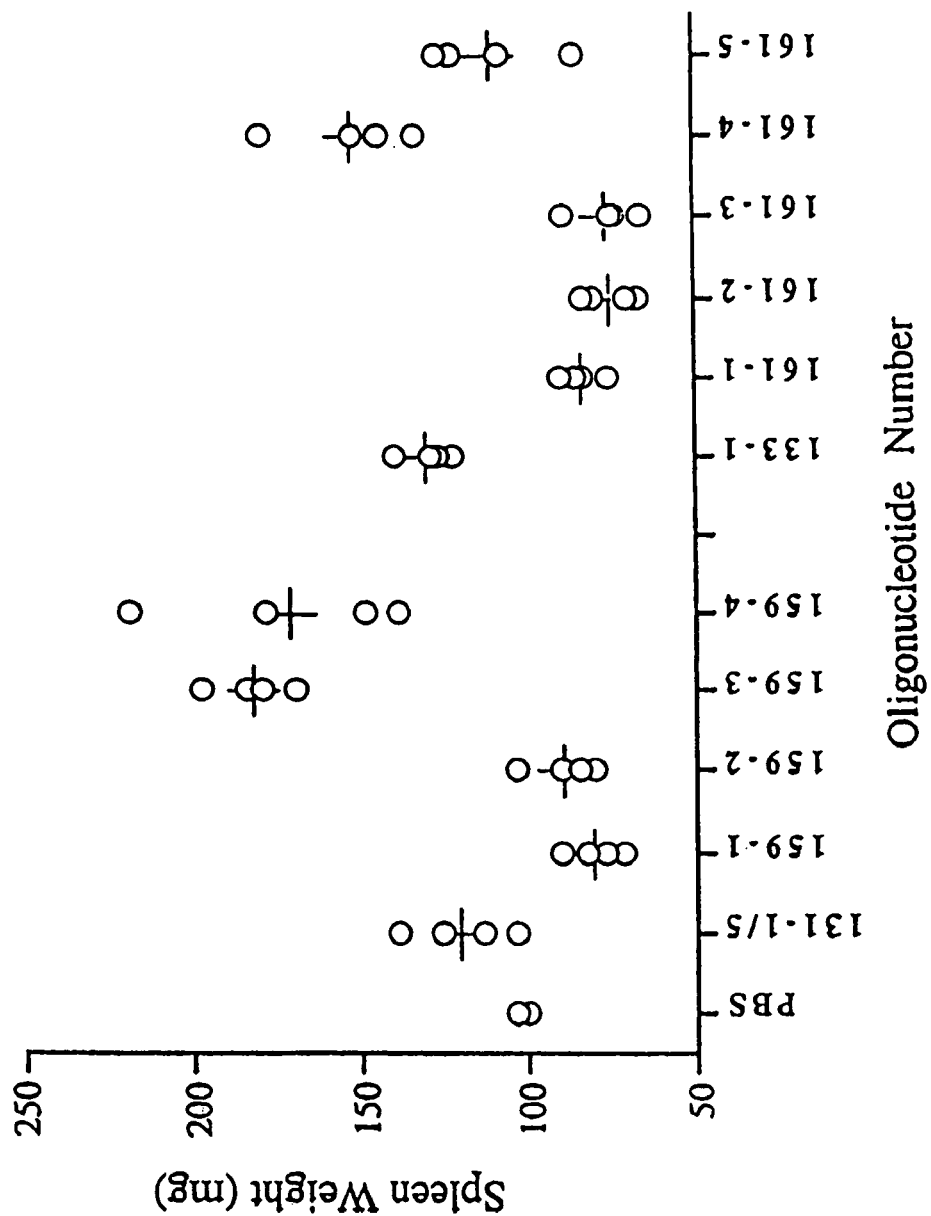
Figure 13B:
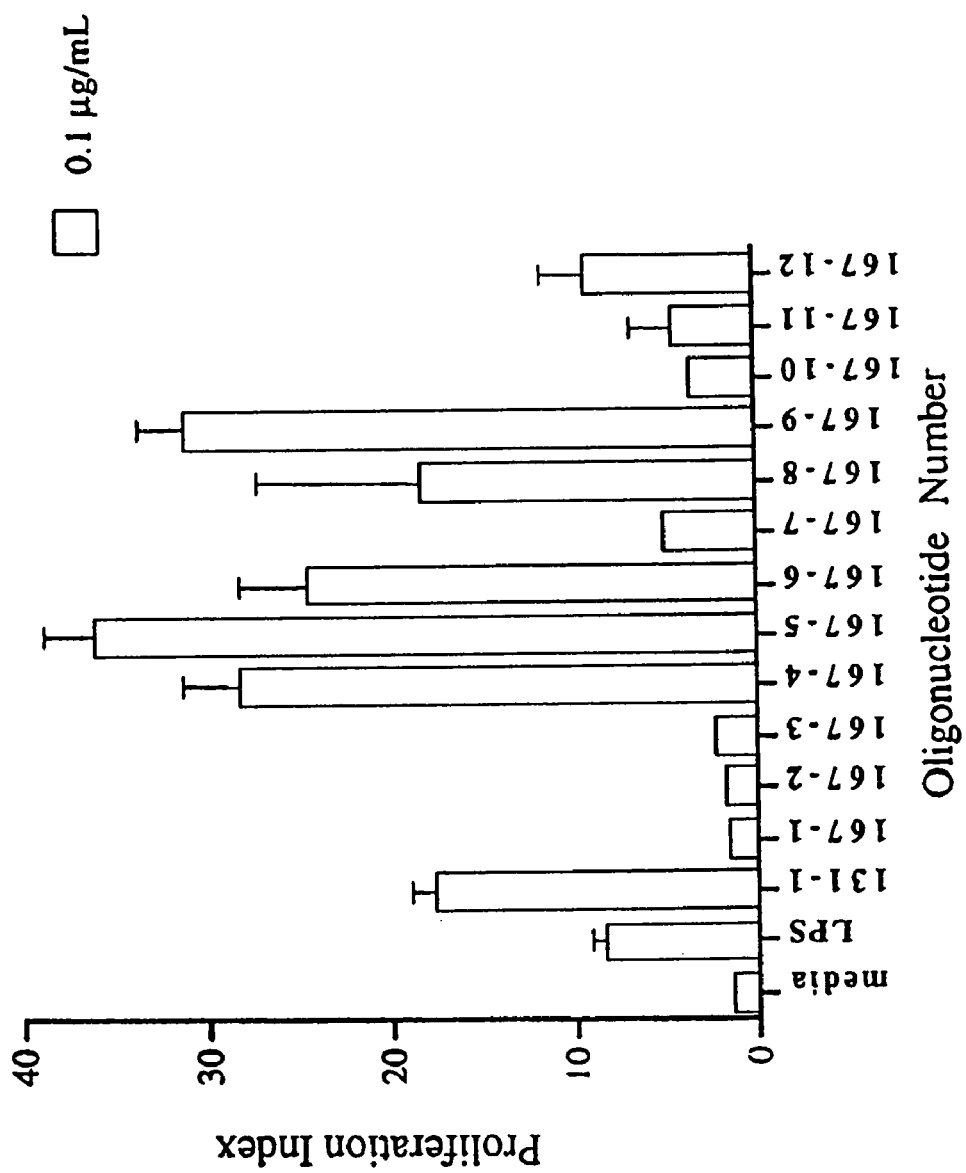
Figure 14B:
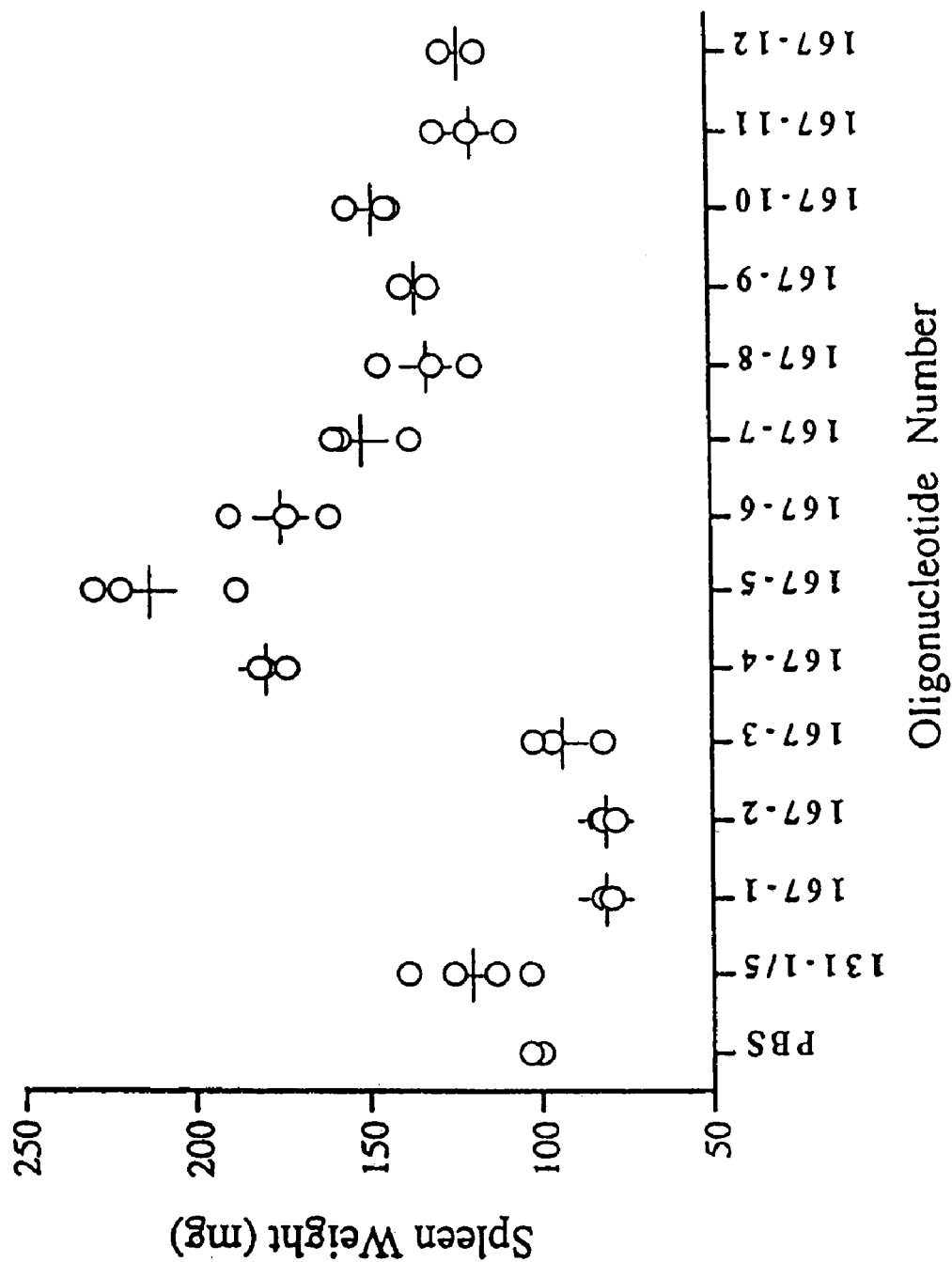
Figure 15A:
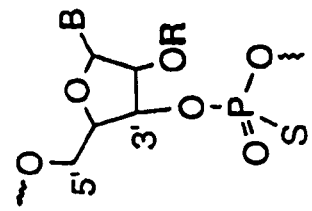
FIGS. 15A-15B shows results of proliferation assays using oligonucleotides (SEQ ID NOs:69-72) having 2'-O-methylribonucleoside or 2'-O-methoxyethyl substitutions at various positions.
Figure 15B:
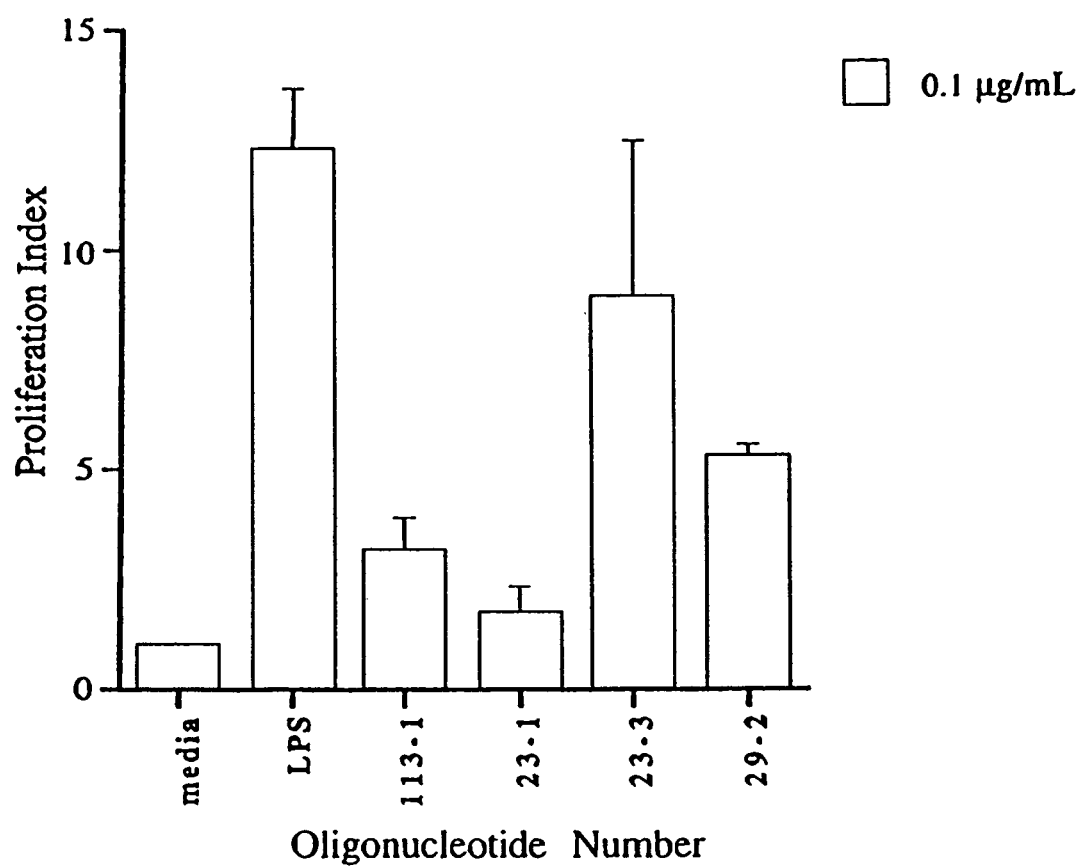
Figure 16A:
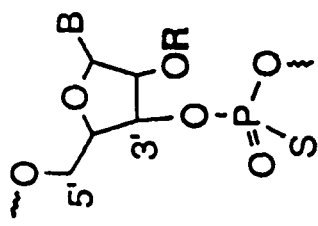
FIGS. 16A-16B shows results of spleen weight assays using oligonucleotides (SEQ ID NOs:69-72) having 2'-O-methylribonucleoside or 2'-O-methoxyethyl substitutions at various positions.
Figure 16B:
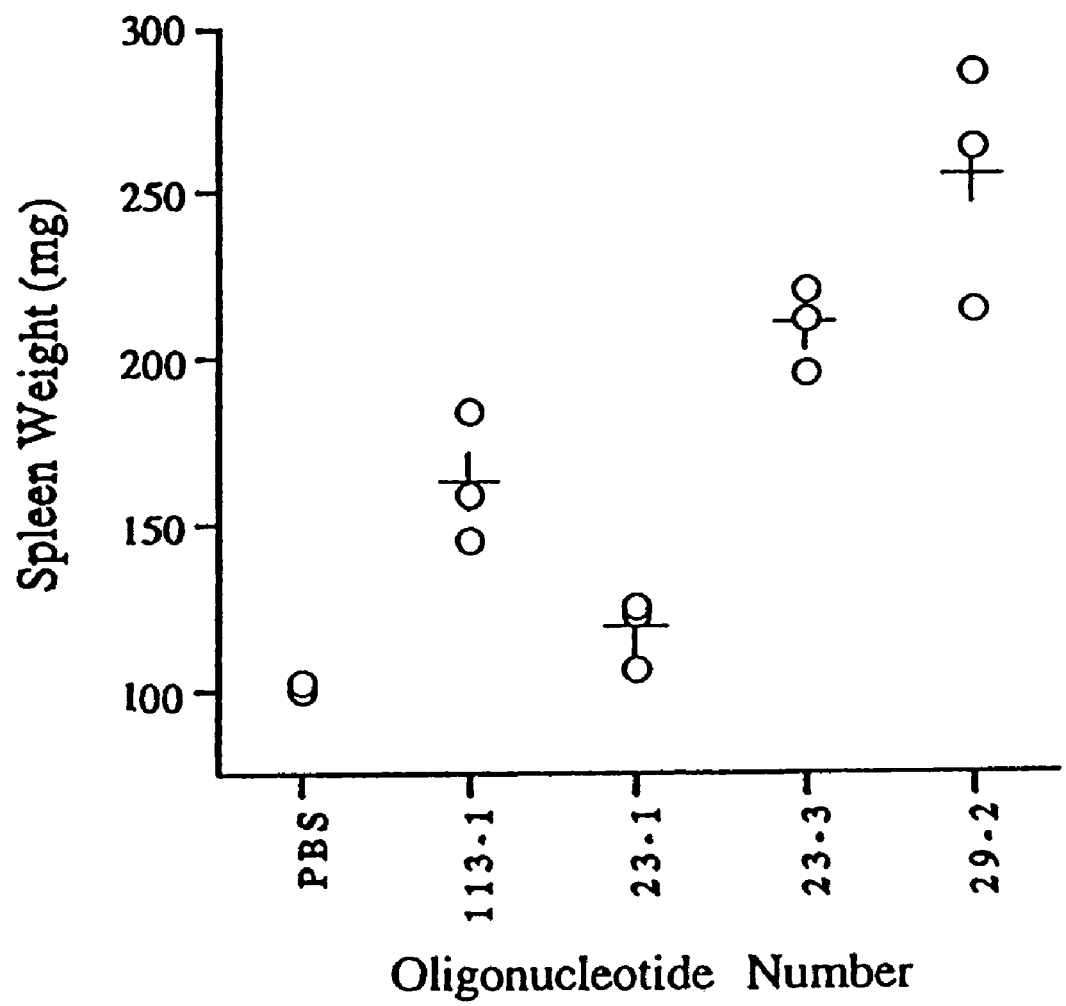

Table 2 shows representative positions and structures of immunostimulatory moieties within an immunostimulatory oligonucleotide having an upstream potentiation domain. See FIG. 7 for definitions of Spacer 9 and Spacer 18 as referred to in Tables 2 and 3.

TABLE 2

| Position | TYPICAL IMMUNOSTIMULATORY MOIETY |
|---|---|
| X2 | 2-aminobutyl-1,3-propanediol linker |
| X1 | C3-linker, 2-aminobutyl-1,3-propanediol linker, β-L-deoxynucleoside |
| U1 | 1',2'-dideoxyribose, C3-linker, 2'-O-methyl-ribonucleoside |
| U2 | 1',2'-dideoxyribose, C3-linker, Spacer 18, 3'-deoxynucleoside, nucleoside methylphosphonate, β-L-deoxynucleoside, 2'-O-propargyl-ribonucleoside |
| U3 | 1',2'-dideoxyribose, C3-linker, Spacer 9, Spacer 18, nucleoside methylphosphonate, 2'-5' linkage |
| U2 + U3 | 1',2'-dideoxyribose, C3-linker,,β-L-deoxynucleoside |
| U3 + U4 | nucleoside methylphosphonate, 2'-O-methoxyethyl-ribonucleoside |
| U5 + U6 | 1',2'-dideoxyribose, C3-linker |
| X1 + U3 | 1',2'-dideoxyribose |

Table 3-shows representative positions and structures of immunostimulatory moieties within an immunostimulatory oligonucleotide having a downstream potentiation domain.

TABLE 3

| Position | TYPICAL IMMUNOSTIMULATORY MOIETY |
|---|---|
| X3 | nucleoside methylphosphonate |
| X4 | nucleoside methylphosphonate, 2'-O-methyl-ribonucleoside |
| D1 | 1',2'-dideoxyribose, nucleoside methylphosphonate |
| D2 | 1',2'-dideoxyribose, C3-linker, Spacer 9, Spacer 18, 2-aminobutyl-1,3-propanediol -linker, nucleoside methylphosphonate, β-L-deoxynucleoside |
| D3 | 3'-deoxynucleoside, 2'-O-propargyl-ribonucleoside, 2'-5'-linkage |
| D2 + D3 | 1',2'-dideoxyribose, β-L-deoxynucleoside |

In another embodiment of the invention, the oligonucleotide according to the invention has one or two accessible 5' ends. The present inventors have discovered that immunostimulatory moieties in the region 5' to the immunostimulatory dinucleotide have a greater impact on immunostimulatory activity than do similar substitutions in the region 3' to the immunostimulatory dinucleotide. This observation suggests that the 5'-flanking region of CpG-PS-oligos plays an important role in immunostimulatory activity. Moreover, the inventors have discovered that compounds having two oligonucleotide units attached by way of a 3'-5' or 3'-3' linkage have greater immunostimulatory activity than do compounds in which the two oligonucleotide units are attached by way of a 5'-5' linkage. In some preferred embodiments, therefore, the immunostimulatory oligonucleotide according to the invention comprises a 3'-3' linkage. In some such embodiments, the oligonucleotides have one or two accessible 5' ends.

In a second aspect, the invention provides methods for modulating the immunostimulatory effect of an immunostimulatory oligonucleotide. In some embodiments, the method comprises introducing into the immunostimulatory domain a dinucleotide analog that includes a non-naturally occurring pyrimidine base, as described above for the first aspect of the invention. In some embodiments, the method comprises introducing into the immunostimulatory domain and/or potentiation domain an immunostimulatory moiety at a specified position, as described above. In some embodiments, the method comprises introducing into the oligonucleotide a 3'-3' linkage.

For purposes of the invention, "introducing an immunostimulatory moiety" at a specified position simply means synthesizing an oligonucleotide that has an immunostimulatory moiety at the specified position. For example, "introducing an immunostimulatory moiety into position U6" simply means synthesizing an oligonucleotide that has an immunostimulatory moiety at such a position, with reference to, e.g., the following structure:

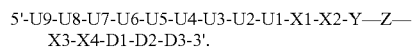

Preferably, the methods according to this aspect of the invention include introducing an immunostimulatory moiety at a position in the immunostimulatory domain or in an upstream or downstream potentiation domain according to the preferred substitution patterns described in Tables 1-3.

The methods according to this aspect of the invention can be conveniently carried out using any of the well-known synthesis techniques by simply using an appropriate immunomodulatory moiety monomer synthon in the synthesis process in an appropriate cycle to obtain the desired position. Preferred monomers include phosphoramidites, phosphotriesters and H-phosphonates. PS-oligos are readily synthesized, e.g., using β-cyanoethylphosphoramidite chemistry on CPG solid support using appropriate phosphoramidites, deprotected as required, purified by $C_{18}$ reverse phase HPLC, dialyzed against distilled water and lyophilized. The purity of each PS oligo is readily determined by CGE and the molecular weight can be confirmed by MALDI-TOF mass spectral analysis.

In a third aspect, the invention provides methods for generating an immune response in a patient, such methods comprising administering to the patient an oligonucleotide analog immunostimulatory compound according to the invention.

In the methods according to this aspect of the invention, preferably, administration of compounds is parenteral, oral, sublingual, transdermal, topical, intranasal, intratracheal, intravaginal, or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.001 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 40 mg oligonucleotide per kg body weight per day. It may be desirable to administer simultaneously, or sequentially a therapeutically effective amount of one or more of the therapeutic compositions of the invention to an individual as a single treatment episode. In some instances, dosages below the above-defined ranges may still provide efficacy. In a preferred embodiment, after the composition of matter is administered, one or more measurement is taken of biological effects selected from the group consisting of complement activation, mitogenesis and inhibition of thrombin clot formation.

In certain preferred embodiments, compounds according to the invention are administered in combination with antibiotics, antigens, allergens, vaccines, antibodies, cytotoxic agents, antisense oligonucleotides, gene therapy vectors, DNA vaccines and/or adjuvants to enhance the specificity or magnitude of the immune response. Either the compound or the vaccine, or both may optionally be linked to an immunogenic protein, such as keyhole limpet hemocyanin, cholera toxin B subunit, or any other immunogenic carrier protein. Any of a plethora of adjuvants may be used, including, without limitation, Freund's complete adjuvant, monophosphoryl lipid A (MPL), saponins, including QS-21, alum, and combinations thereof. Certain preferred embodiments of the methods according to the invention induce cytokines by administration of immunostimulatory oligonucleotide compounds. In certain embodiments the immunostimulatory oligonucleotide compounds are conjugated to an antigen, hapten, or vaccine. As discussed above, the present inventors have discovered that an accessible 5' end is important to the activity of certain immunostimulatory oligonucleotide compounds. Accordingly, for optimum immunostimulatory activity, the oligonucleotide preferably is conjugated to an antigen or vaccine by means of the 3'-end of oligonucleotide compound.

For purposes of this aspect "in combination with" means in the course of treating the same disease in the same patient, and includes administering the oligonucleotide and/or the vaccine and/or the adjuvant in any order, including simultaneous administration, as well as temporally spaced order of up to several days apart. Such combination treatment may also include more than a single administration of the oligonucleotide, and/or independently the vaccine, and/or independently the adjuvant. The administration of the oligonucleotide and/or vaccine and/or adjuvant may be by the same or different routes.

The method according to this aspect of the invention is useful for model studies of the immune system, and is further useful for the therapeutic treatment of human or animal disease.

In a fourth aspect, the invention provides methods for therapeutically treating a patient having disease caused by a pathogen, such methods comprising administering to the patient an oligonucleotide analog immunostimulatory compound according to the invention. Administration is carried out as described for the third aspect of the invention.

In a fifth aspect, the invention provides methods for treating a cancer patient, such methods comprising administering to the patient an oligonucleotide analog immunostimulatory compound according to the invention. Administration is carried out as described for the third aspect of the invention.

In a sixth aspect, the invention provides methods for treating autoimmune disorders, such as autoimmune asthma, such methods comprising administering to the patient an oligonucleotide analog immunostimulatory compound according to the invention. Administration is carried out as described for the third aspect of the invention.

In a seventh aspect, the invention provides methods for treating airway inflammation or allergies, such methods comprising administering to the patient an oligonucleotide analog immunostimulatory compound according to the invention. Administration is carried out as described for the third aspect of the invention.

The following examples are intended to further illustrate certain preferred embodiments of the invention, and are not intended to limit the scope of the invention.

EXAMPLES

Example 1

Synthesis of Oligonucleotides Containing Immunomodulatory Moieties

Oligonucleotides were synthesized on a 1 micromolar scale using an automated DNA synthesizer (Expedite 8909, PerSeptive Biosystems, Foster City, Calif.). Standard deoxynucleoside phosphoramidites are obtained from PerSeptive Biosystems. 1',2'dideoxyribose phosphoramidite, propyl-1-phosphoramidite, 2'-deoxy-5-nitroindole-ribofuranosyl phosphoramidite, 2'-deoxy-uridine phosphoramidite, 2'-deoxy-P phosphoramidite, 2'-deoxy-2-aminopurine phosphoramidite, 2'-deoxy-nebularine phosphoramidite, 2'-deoxy-7-deazaguanosine phosphoramidite, 2'-deoxy-4-thiouridine phosphoramidite, 2'-deoxy-isoguanosine phosphoramidite, 2'-deoxy-5-methylisocytosine phosphoramidite, 2'-deoxy-4-thiothymidine phosphoramidite, 2'-deoxy-K-phosphoramidite, 2'-deoxy-2-aminoadenosine phosphoramidite, 2'-deoxy-N-4-ethyl-cytosine phosphoramidite, 2'-deoxy-6-thioguanosine phosphoramidite, 2'-deoxy-7-deaza-xanthosine phosphoramidite, 2'-deoxy-8-bromoguanosine phosphoramidite, 2'-deoxy-8-oxoguanosine phosphoramidite, 2'-deoxy-5-hydroxycytosine phosphoramidite, arabino-cytosine phosphoramidite and 2'-deoxy-5-propynecytosine phosphoramidite were obtained from Glen Research (Sterling, Va.). 2'-Deoxy-inosine phosphoramidite were obtained from ChemGenes (Ashland, Mass.).

Normal coupling cycles or a coupling cycle recommended by the phosphoramidite manufacturer were used for all phosphoramidites. Beaucage reagent was used as an oxidant to obtain phosphorothioate modification. After synthesis, oligonucleotides were deprotected by incubating CPG-bound oligonucleotide with concentrated ammonium hydroxide solution for 1.5-2 hours at room temperature and then incubating the ammonium hydroxide supernatant for 12 hours at 55 degrees C. or as recommended by phosphoramidite manufacturer. The ammonium hydroxide solution was evaporated to dryness in a speed-vac and 5'-DMTr-oligonucleotides were purified by HPLC on a C18 reverse-phase matrix using a solvent system of 0.1 M ammonium acetate and 1:5 ratio 0.1 M ammonium acetate in acetonitrile. Then the oligonucleotides were treated with 80% acetic acid to remove the DMTr group, converted to sodium form and desalted by dialysis against double distilled water. Oligonucleotides were filtered through 0.4μ filters, lyophilized and redissolved in double distilled water. Characterization was achieved by denaturing PAGE and MALDI-TOF mass spectrometry.

Example 2

Synthesis of CpG-PS-Oligos Containing Cytosine Analogs

Following the procedures outlined in Example 1, the following oligonucleotides were synthesized:

| Oligo # (SEQ ID NO): | Sequence (5'->3') and Modification[a] |
|---|---|
| 1 | d(CTATCTGACGTTCTCTGT) |
| 2 | d(CTATCTGAC*GTTCTCTGT) |
| 3 | d(CTATCTGACC*TTCTCTGT) |
| 4 | d(CTATCTGAC*GTTCTCTGT) |
| 5 | d(CTATCTGACC*TTCTCTGT) |

[a]CpG-motif is shown in bold. C* represents 5-hydroxycytosine (oligos 2 and 3) or N4-ethylcytosine (oligos 4 and 5).

The oligonucleotides were characterized by CGE and MALDI-TOF mass spectrometry (Brucker Proflex III MALDI-TOF mass spectrometer with 337 nm N2 laser). Molecular weights observed and calculated (shown in parentheses) for each oligonucleotide are as follows: Oligo 1, 5704 (5704.8); Oligo 2, 5720 (5720.8); Oligo 3, 5681 (5680.7); Oligo 4, 5733 (5733); Oligo 5, 5694 (5693).

Example 3

Analysis of Spleen Weights in Treated Mice

Female BALB/c mice (4-5 weeks, 19-21 g, Charles River, Wilmington, Mass.) were used in the study. The animals were fed with commercial diet and water ad lib. The animals were injected intraperitoneally with 5 or 10 mg/kg dose of immunostimulatory oligonucleotide compound dissolved in sterile PBS. One group of mice received PBS alone to serve as a control (PBS). Four animals were used for each immunostimulatory oligonucleotide compound. Mice were sacrificed 72 h later, spleens were harvested and weighed.

Example 4

Analysis of Immunostimulatory Oligonucleotide Compounds in Mouse Lymphocyte Proliferation Assay Spleens from CD-1, BALB/c, C57BL/6 mouse (4-8 weeks) were used as source of lymphocytes. Single cell suspensions were prepared by gently mincing with the frosted ends of glass slides. Cells were then cultured in RPMI complete medium [RPMI medium supplemented with 10% fetal bovine serum (FBS) (heat-inactivated at 56° C. for 30 min), 50 μM 2-mercaptoethanol, 100 U/mL penicillin, 100 μg/mL streptomycin, 2 mM L-glutamine]. The cells were then plated in 96-well dishes at a density of $10^6$ cells/mL in a final volume of 100 μL. Immunostimulatory oligonucleotide compounds or LPS (lipopolysaccharide) were added to the cell culture in 10 μL of TE buffer (10 mM Tris-HCl, pH 7.5, 1 mM EDTA). The cells were then set to culture at 37° C. After 44 h, 1 μCi $^3$H-uridine (Amersham, Arlington Heights, Ill.) was added to the culture in 20 μL of RPMI medium, and the cells were pulse-labeled for another 4 h. The cells were harvested by automatic cell harvester (Skatron, Sterling, Va.), and the filters were counted by a scintillation counter. The experiments were performed in triplicate.

Example 5

Lymphocyte Proliferatory Activity of CpG-PS-Oligos Containing Cytosine Analogs

The immunostimulatory activity of CpG-PS-oligos 1-5 (Example 4) was studied using a BALB/c mouse lymphocyte proliferation assay. In brief, mouse spleen cells were cultured and incubated with CpG-PS-oligos at 0.1, 0.3, 1.0 and 3.0 μg/mL concentration for 48 hr and cell proliferation was measured by $^3$H-uridine incorporation.

Figure 23A:
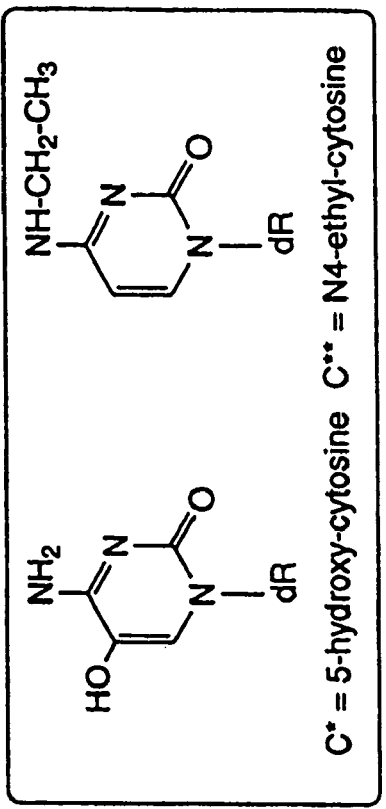
FIGS. 23A-23B shows results of spleen weight assays using oligonucleotides (SEQ ID NOs:1-5) having 5-hydroxycytosine or N4-ethylcytosine substitution within the immunostimulatory dinucleotide.
Figure 23B:
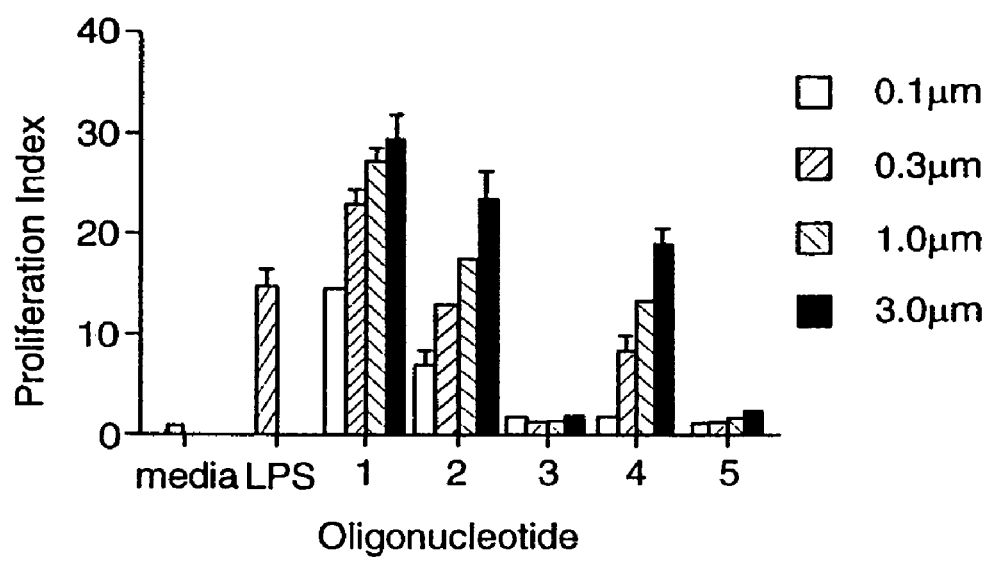

FIG. 23 shows the dose-dependent cell proliferatory activity of oligos 1-5 in mouse lymphocyte cultures. At a dose of 3.0 μg/mL, oligo 1, with natural cytidine, showed a proliferation index of 29.5±2.1. Oligo 2, in which the cytosine base of the deoxycytidine of the CpG-motif is replaced with a 5-hydroxycytosine, also showed dose-dependent lymphocyte proliferation. A proliferation index of 23.7±2.9 at 3.0 μg/mL dose was observed for oligo 2. PS-Oligo 4, which contained N4-ethyl-cytosine in place of the cytosine base in the CpG-motif, also showed dose-dependent cell-proliferation activity. The proliferation index of 18.7±1.6 observed for oligo 4 at a dose of 3 μg/mL suggests that the presence of a bulky hydrophobic substitution on the 4-amino group of cytosine in a CpG-motif slightly impedes immunostimulatory activity.

Oligo 3, in which 5-hydroxy-deoxycytidine was placed in the deoxyguanosine position instead of the deoxycytidine position of the CpG-motif, showed a proliferation index that was similar to that observed for media control (FIG. 23). Similarly, the control Oligo 5 in which deoxyguanosine in the CpG-motif was substituted with N4-ethyldeoxycytidine, showed cell proliferation similar to that of media control.

Other oligos, in which cytosine base in the CpG-motif was replaced with 5-methyl-deoxycytosine (2; see FIG. 28), 5-methyl-deoxyisocytosine (3), deoxyuridine (5), or deoxy-P-base (7) showed no or insignificant cell proliferatory activity in the same assay system. These results suggest that (i) cell proliferatory activity is maintained when the cytosine base of the CpG motif is replaced with 5-hydroxycytosine or N4-ethylcytosine (Oligos 2 and 4, respectively), but (ii) substitution of the guanine base with these cytosine analogs results in a loss of cell proliferatory activity.

Example 6

Splenomegaly in Mice Induced by CpG-PS-Oligos Containing Cytosine Analogs

Figure 24A:
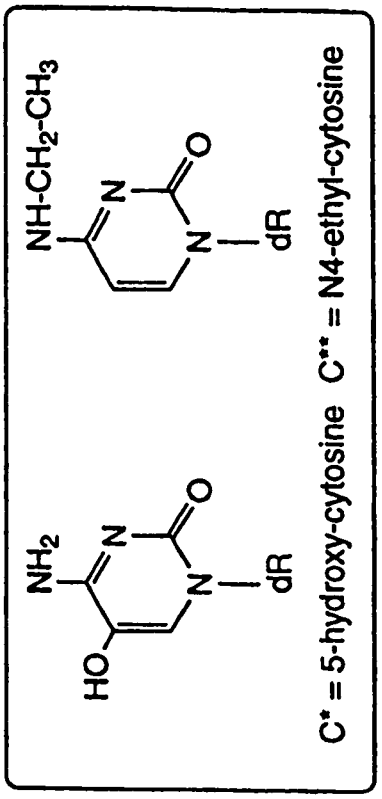
FIGS. 24A-24B shows results of spleen weight assays using oligonucleotides (SEQ ID NOs:1-5) having 5-hydroxycytosine or N4-ethylcytosine substitution within the immunostimulatory dinucleotide.
Figure 24B:
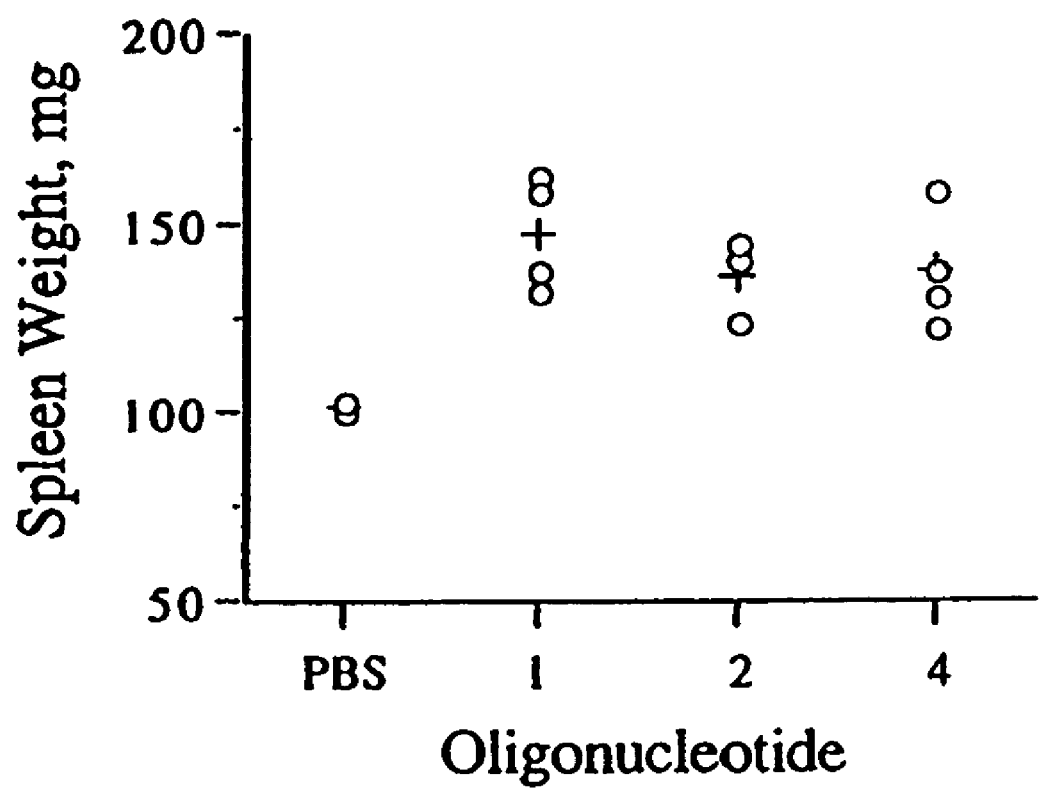
Figure 25A:
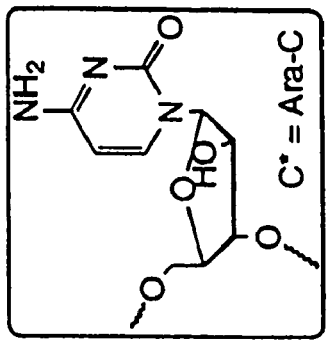
FIGS. 25A-25B shows results of proliferation assays using oligonucleotides (SEQ ID NOs:1, 111-112) having arabinofuranosylcytosine (aracytidine: Ara-C) substitution within the immunostimulatory dinucleotide.
Figure 25B:
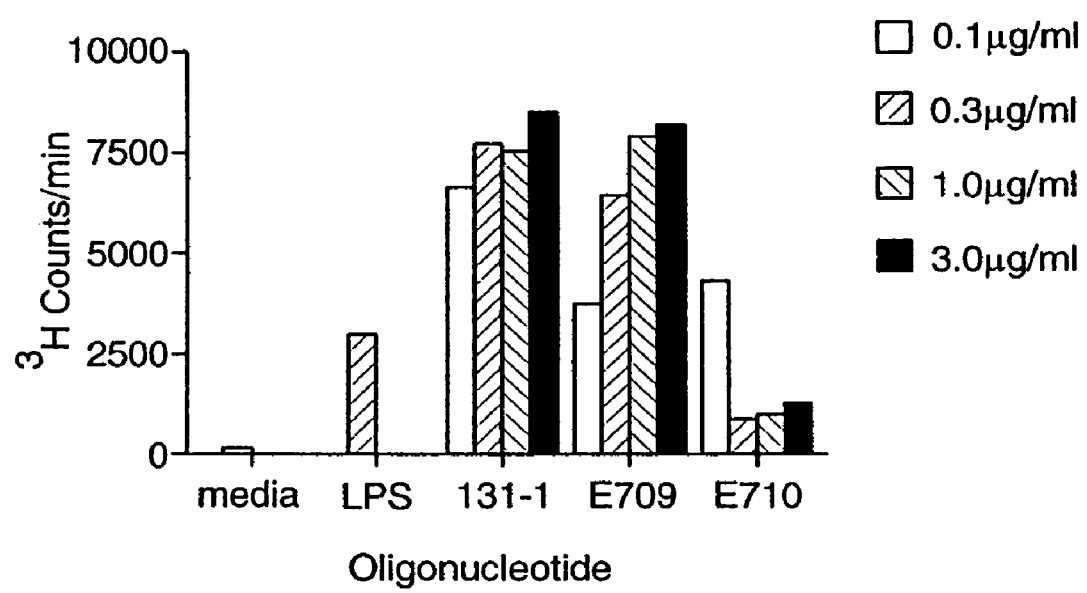
Figure 26A:
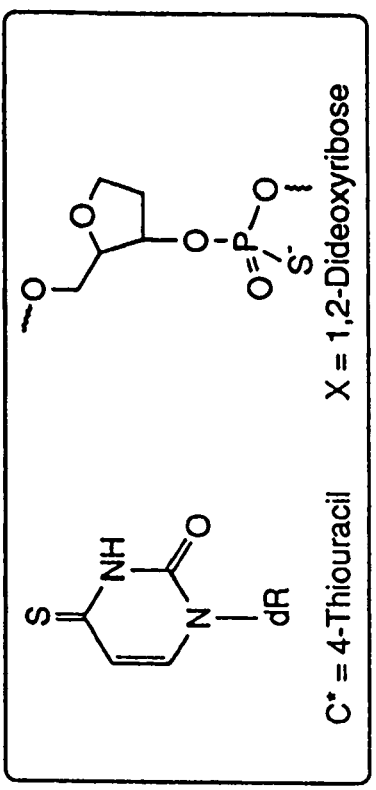
FIGS. 26A-26B shows results of spleen weight assays using oligonucleotides (SEQ ID NOs:1, 103-104) having 4-thiouracil substitution within the immunostimulatory dinucleotide.
Figure 26B:
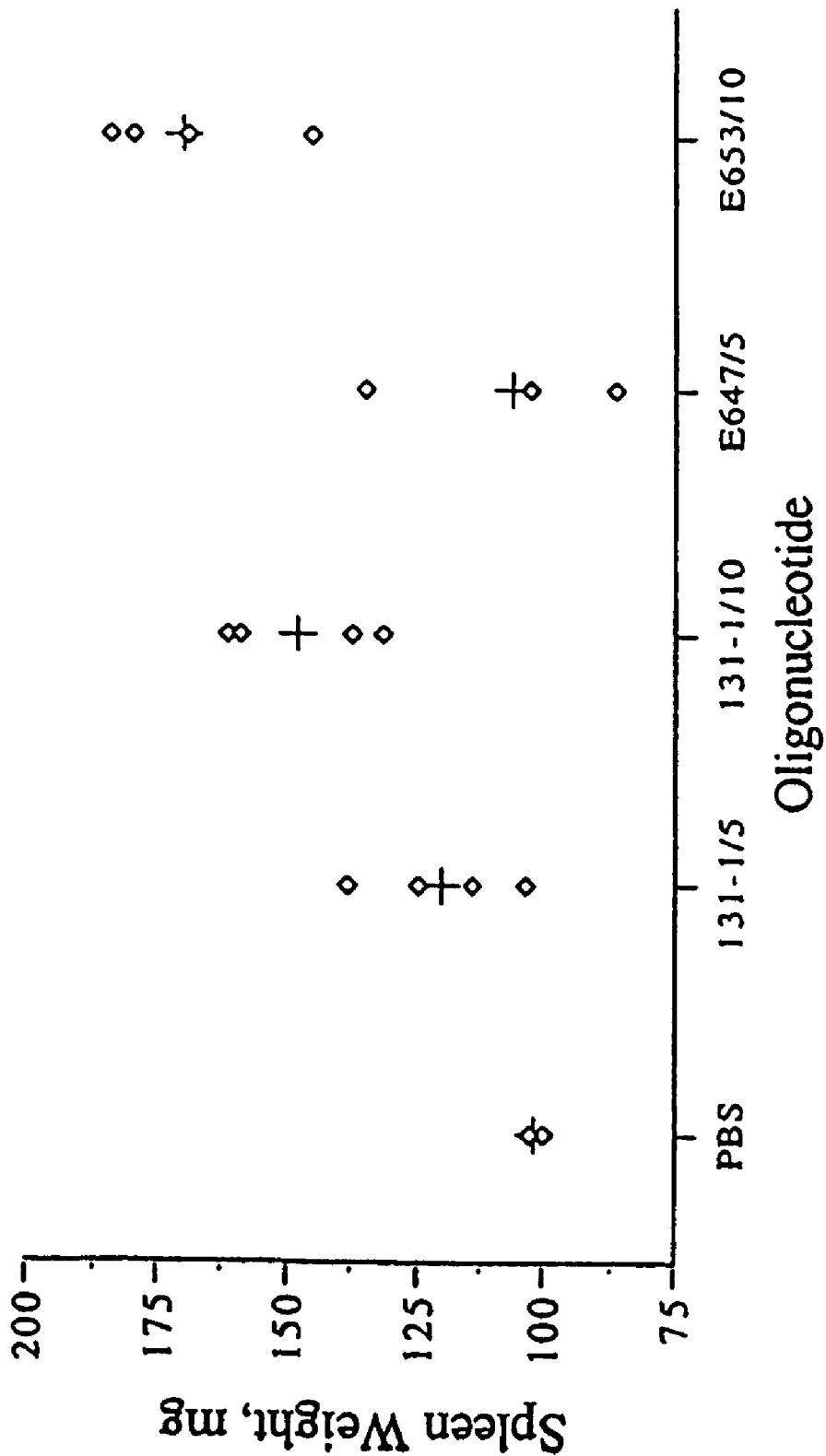

To confirm the in vitro effects of CpG-PS-oligos, Oligos 1, 2, and 4 (from Example 4) were injected intraperitoneally (ip) to BALB/c mice at a dose of 10 mg/kg and the change in spleen weight was measured as an indicator of the level of immunostimulatory activity of each PS-oligo. The change in spleen weight as a result of treatment with CpG-PS-oligos is presented in FIG. 24. Female BALB/c mice (4-6 weeks, 19-21 gm) were divided in to different groups with four mice in each group. Oligonucleotides were dissolved in sterile PBS and administered intraperitoneally to mice at a dose of 10 mg/kg. After 72 hr, mice were sacrificed and spleens were harvested and weighed. Each circle represents the spleen weight of an individual mouse and the + represents the mean spleen weight for each group.

Oligo 1, which has natural deoxycytidine in the CpG-motif, showed about 45% increase in spleen weight at a dose of 10 mg/kg, compared with the control group of mice that received PBS. Oligo 2, which has a 5-hydroxycytosine in place of the cytosine base in the CpG-motif, showed about 35% increase in spleen weight at the same dose. Oligo 4, which has N4-ethylcytosine in place of the cytosine base in the CpG-motif, showed about 34% increase in spleen weight at the same dose compared to the control group. These data confirm the results observed in lymphocyte proliferation assays for these oligos containing modified cytidine analogs in place of deoxycytidine in the CpG-motif.

Example 7

Structure-Activity Relationships of C*pG-PS-Oligos

The presence of a methyl group at the 5-position of cytosine (5-methyl-deoxycytosine, 2 (FIG. 28)) in a CpG-motif completely abolishes CpG related immunostimulatory effects of CpG-PS-oligos. Based on the results observed in in vitro and in vivo experiments we have constructed structure-activity relationships for the PS-oligos containing cytosine analogs.

The replacement of the cytosine base (1) in the CpG-motif with 5-methyl-isocytosine (3) resulted in complete loss of immunostimulatory activity, as is the case with 5-methylcytosine (2), which could be as a result of switching the keto and amino groups at the 2 and 4-positions, respectively, and/or placing a hydrophobic methyl group at the 5-position of cytosine.

Oligo 2, containing a hydrophilic hydroxy substitution at the 5-position of the cytosine in the CpG-motif, showed immunostimulatory activity similar to that of oligo 1, which contains the natural cytosine base. This observation suggests that bulky hydrophilic groups are better tolerated than are hydrophobic groups at the 5-position of cytosine for immunostimulatory activity of CpG-PS-oligos. Perhaps the binding pocket for the CpG-oligos on receptor is hydrophilic in nature and can not accommodate a hydrophobic group at the 5-position of cytosine.

When the cytosine base in the CpG-motif is replaced with uracil (5 (see FIG. 28)), in which keto groups are present at both the 2 and 4-positions, no immunostimulatory activity was observed, suggesting that a hydrogen bond donor amino group at the 4-position of cytosine is critical for immunostimulatory activity. When a large hydrophobic ethyl group is placed on 4-amino group of cytosine in a CpG-motif, reduced lymphocyte proliferation and a slightly reduced increase in spleen weight in mice were observed, suggesting that a bulky ethyl group at this position does not interfere with binding of the CpG-PS-oligo to the receptor factors responsible for immunostimulatory activity. In spite of the ethyl substitution, the 4-amino group of N4-ethylcytosine (6) can participate in hydrogen bond formation with an acceptor. The modified pyrimidine base dP, in which the nitrogen group located at the 4-position involved in ring structure formation with the 5-position, and which does not have a hydrogen bond donor amino group at the 4-position, had no mouse lymphocyte proliferation activity in cultures, suggesting that the 4-amino group of cytosine in a CpG-motif is critical for immunostimulatory activity.

In conclusion, the results presented here show that the functional groups at 2, 3, and 4 positions of the cytosine are important for CpG-related immunostimulatory activity. A hydrophobic substitution at the 5-position of cytosine completely suppresses immunostimulatory activity of a CpG-oligo, while a hydrophilic group at this position is tolerated well. In addition, the immunostimulatory activity of CpG-PS-oligos containing 5-hydroxycytosine or N4-ethylcytosine in place of cytosine in the CpG-motif can be modulated significantly by incorporating appropriate chemical modifications in the 5'-flanking sequence, suggesting that these cytosine analogs in a CpG-motif are recognized as part of an immunostimulatory motif.

Example 8

Synthesis of End-Blocked CpG-PS Oligonucleotides

Figure 17C:
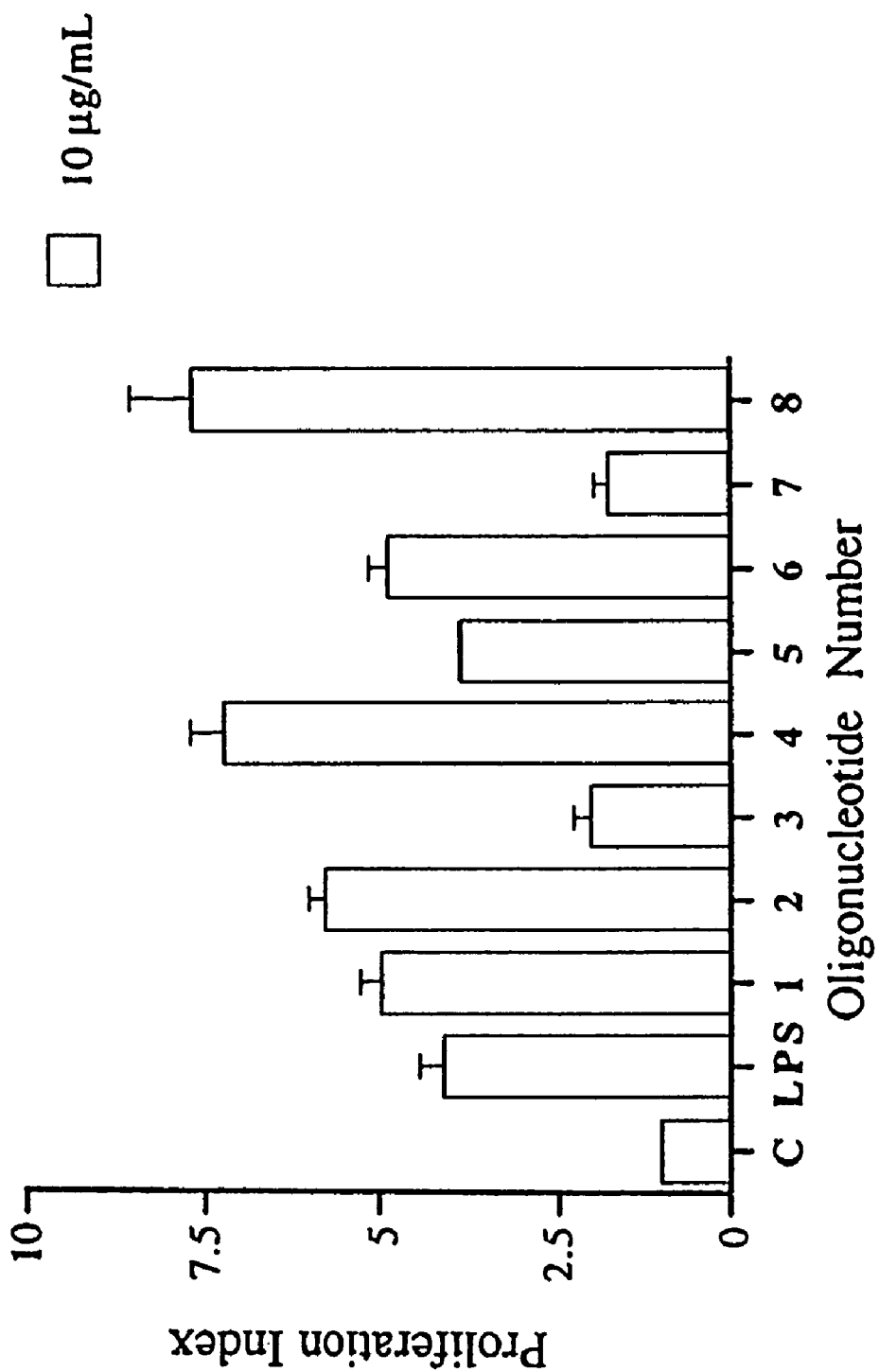
FIGS. 17A-17B shows results of proliferation assays using oligonucleotides (SEQ ID NOs:73-80) having 5'-3', 5'-5', or 3'-3' linkage substitutions at various positions.
Figure 18B:
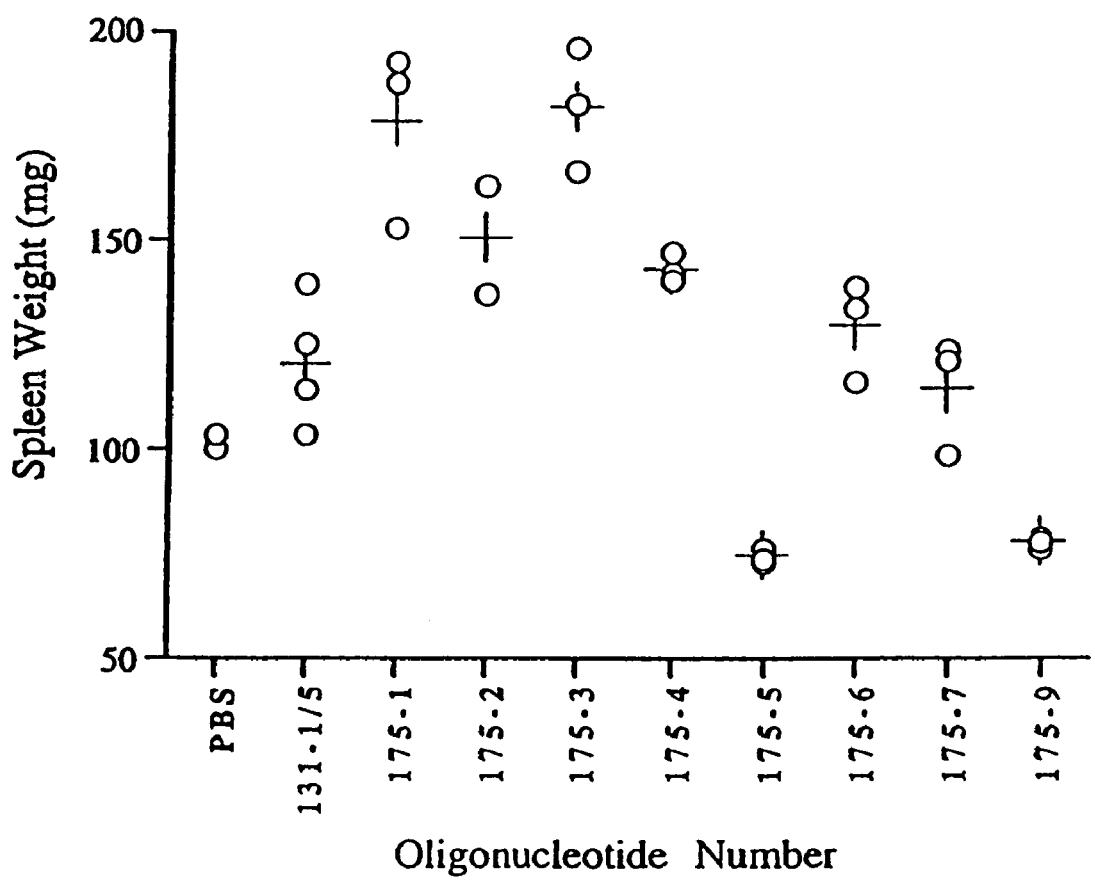
Figure 19B:
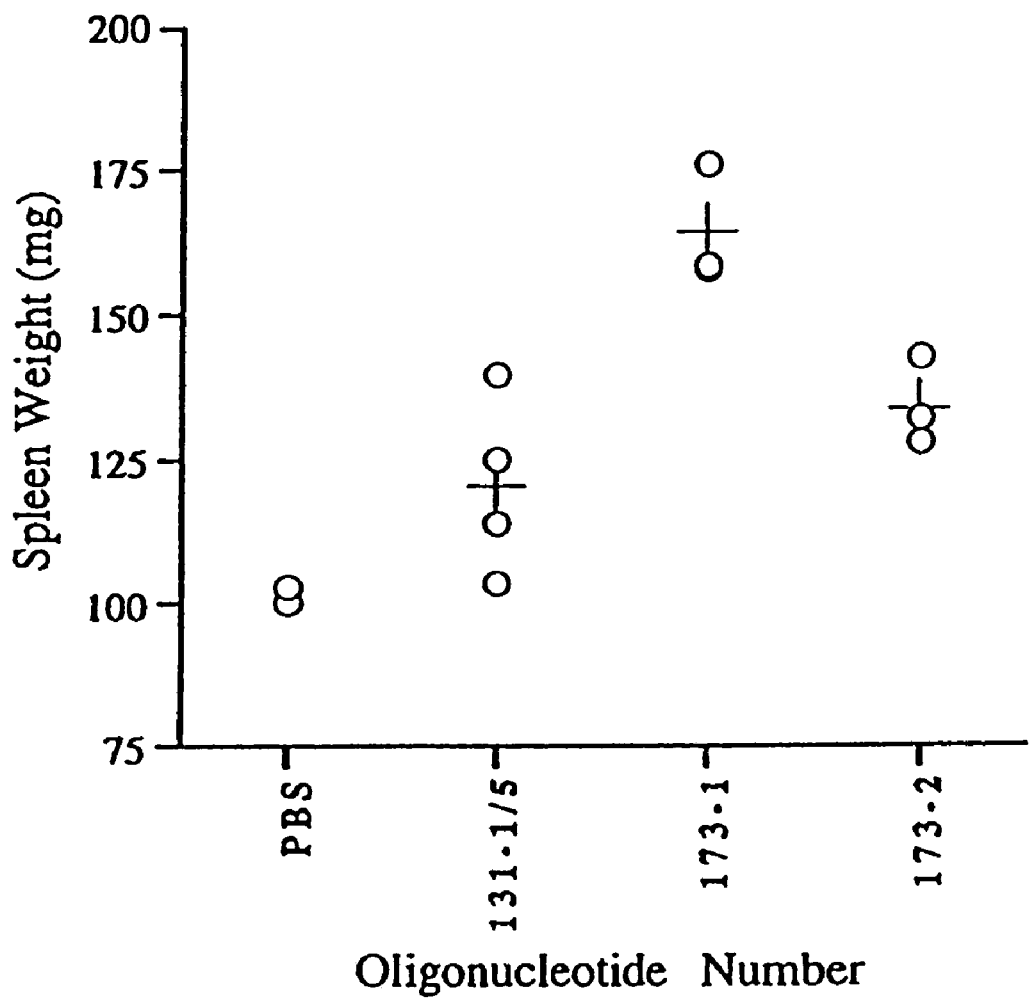
Figure 20B:
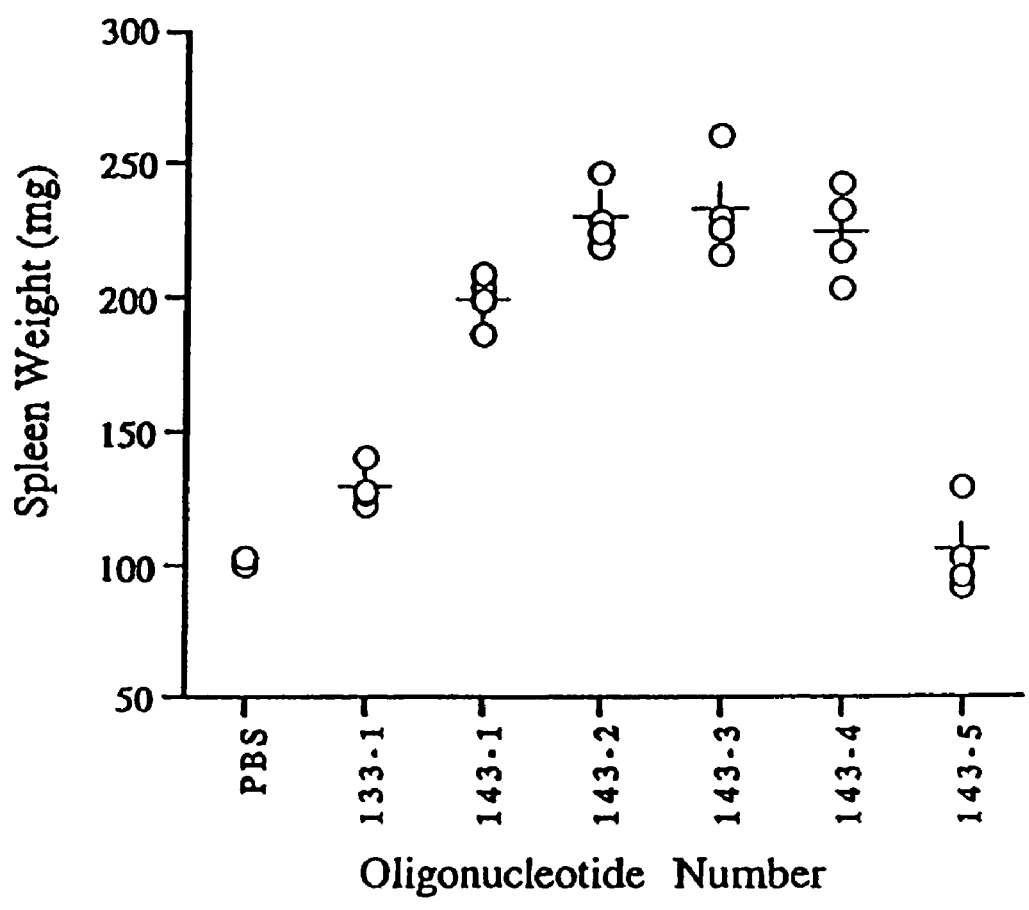
Figure 22B:
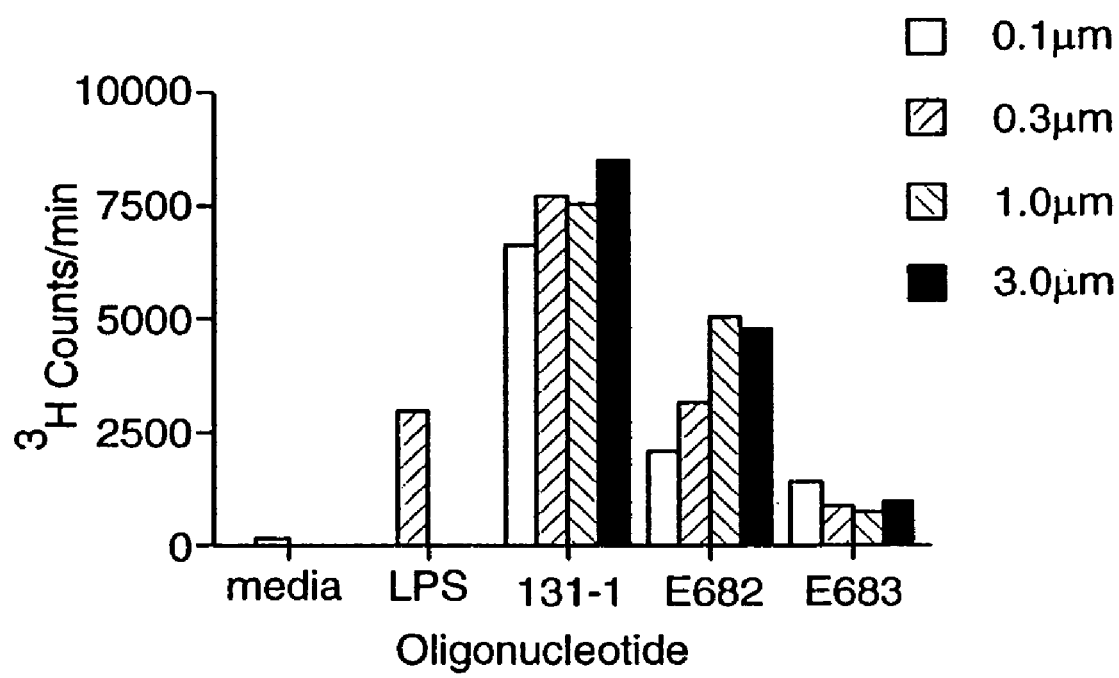

The CpG-PS-oligos shown in FIG. 17 were synthesized using an automated synthesizer and phosphoramidite approach. Oligo 1 (16-mer) was synthesized using nucleoside-5'-β-cyanoethylphosphoramidites. Oligo 2, a 32-mer, was synthesized using nucleoside-3'-β-cyanoethylphosphoramidites and controlled pore glass support (CPG-solid support) with a 3'-linked nucleoside in which 16-mer sequence of Oligo 1 was repeated twice; therefore, Oligo 2 had two 16-mers (Oligo 1) linked by a normal 3'-5'-linkage. Oligo 3, a 32-mer, was synthesized with two 16-mers (Oligo 1) linked by a 5'-5'-linkage, so Oligo 3 had two 3'-ends and no 5'-end. Synthesis of Oligo 3 was carried out in two steps: the first 16-mer was synthesized using nucleoside-3'-β-cyanoethylphosphoramidites and solid support with a 3'-linked nucleoside, and then synthesis of the second 16-mer segment was continued using nucleoside-5'-β-cyanoethylphosphoramidites. Oligo 4, a 32-mer, comprised two 16-mers (Oligo 1) linked by a 3'-3'-linkage, so Oligo 4 had two 5'-ends and no 3'-end. Synthesis of Oligo 4 was carried out in two steps: the first 16-mer was synthesized using nucleoside-5'-β-cyanoethylphosphoramidites and solid support with a 5'-linked nucleoside, and the synthesis of the second 16-mer segment was continued using nucleoside-3'-β-cyanoethyl-phosphoramidites. Synthesis of Oligos 5-8 was carried out by using the same nucleoside-β-cyanoethyiphosphoramidites as for Oligos 1-4, respectively. At the end of the synthesis, Oligos 1-8 were deprotected with concentrated ammonia solution, purified by reversed phase HPLC, detritylated, desalted and dialyzed. The purity of each PS-oligo was checked by CGE and the molecular weight was confirmed by MALDI-TOF mass spectral analysis (Table 1). The sequence integrity and directionality of 5'-CpG motif in Oligos 1-8 were confirmed by recording melting temperatures ($T_m$S) of the duplexes with their respective DNA complementary strands (5'-AAGGTC-GAGCGTTCTC-3' (SEQ ID NO: 6) for Oligos 1-4, and 5'-ATGGCGCACGCTGGGAGA-3' (SEQ ID NO: 7) for Oligos 5-8). The $T_m$s of these duplexes were 53.9±0.9° C. (Oligos 1-4), 61.8° C. (Oligo 5), and 58.8±0.6° C. (Oligos 6-8) (note that Oligo 5 was a 18-mer and Oligos 6-8 were 32-mers but not 36-mers).

Example 9

Mouse Spleen Lymphocyte Proliferatory Activity of End-Blocked CpG-PS Oligonucleotides Immunostimulatory activity of the end-blocked CpG-PS-oligos of Example 8 was studied initially in a lymphocyte proliferation assay. Typically, mouse (Balb-C) spleen lymphocytes were cultured with CpG-PS-oligos at concentrations of 0.1, 1.0, and 10.0 µg/ml for 48 h and cell proliferation was determined by $^3$H-uridine incorporation, as described in Example 3. Results are shown in FIG. 17

Oligo 1 induced a dose-dependent effect on cell proliferation; at a concentration of 10 µg/ml (~2.0 µM), the proliferation index was 5.0±0.32. Oligo 2, which consisted of two units of Oligo 1 linked by a 3'-5'-linkage, had a proliferation index of 5.8±0.28 at the same dose (~1.0 µM). Oligo 3, which consisted of two units of Oligo 1 linked by a 5'-5'-linkage, had a proliferation index of 2.0±0.26, reflecting a significantly lower immunostimulatory activity than observed with Oligos 1 and 2. Oligo 4, which consisted of two units of Oligo 1 linked by a 3'-3'-linkage, had a proliferation index of 7.2±0.5, reflecting a greater immunostimulatory activity than observed with Oligos 1 and 2.

Similar results were obtained with Oligos 5-8. Oligo 5 had a proliferation index of 3.9±0.12. Oligos 6-8, in which two units of Oligo 5 are linked by a 3'-5'-linkage (Oligo 6), 5'-5'-linkage (Oligo 7), and 3'-3'-linkage (Oligo 8) had proliferation indices of 4.9±0.2, 1.74±0.21, and 7.7±0.82, respectively. Comparison of the results obtained with Oligos 6-8 show that Oligos 6 and 8, in which two Oligo 5 sequences were linked by a 3'-5'-linkage or a 3'-3'-linkage had greater immunostimulatory activity, while Oligo 7, in which two Oligo 5 were linked by a 5'-5'-linkage had significant less immunostimulatory activity, than did Oligo 5.

Based on lymphocyte proliferation results of Oligos 1-8, it is clear that when oligos are linked through their 5'-ends, there is a significant loss of immunostimulatory activity, while if they are linked through their 3'-ends, there is an increase in immunostimulatory activity. It is important to note that 3'-3'-linked oligos have shown substantially greater stability towards degradation by exonucleases than the oligos that contained a free 3'-end, which could also result in increased immunostimulatory activity. The lower immunostimulatory activity of Oligos 3 and 7, in which the 5'-end of oligos is blocked, suggests that accessibility to 5'-end of oligo is essential for immunostimulatory activity of CpG-PS-oligos.

Example 10

Splenomegaly in Mice Induced by End-Blocked CpG-PS Oligonucleotides

To confirm the immunostimulatory activity of Oligos 1-8 (Example 8) in vivo, a dose of 5 mg/kg of oligonucleotides was injected intraperitoneally to Balb-C mice. The mice were sacrificed 72 hours post-administration, spleens were removed, blotted to dryness, and weighed. Change in spleen weight in treated and untreated mice was used as a parameter for immunostimulatory activity.

Administration 5 mg/kg dose of Oligo 1 caused about 40% increase in spleen weight compared with the control mice that received PBS. Administration of Oligos 2 and 4 also caused about 50% increase in spleen weight. Administration of Oligo 3 caused no difference in spleen weight compared with control mice. These results further support the observation that Oligo 3, in which 5'-end was blocked, had significantly less immunostimulatory activity compared to oligos that had accessible 5'-end. These results were also confirmed with the administration of Oligos 5-8. Administration of Oligos 5, 6, and 8 caused about 40-50% increase in spleen weight, whereas no change in spleen weight was observed following the administration of Oligo 7.

The above results suggest that the immunostimulatory activity of PS-oligos containing a CpG motif is significantly minimized if the 5'-end of the oligo is not accessible. This loss in immunostimulatory activity of Oligos 3 and 7 cannot be explained based on nuclease stability, as both oligos have two 3'-ends and are not more susceptible to 3'-exonuclease degradation than are Oligos 1, 2, 5, and 6, which have one 3'-end. PS-Oligos 4 and 8, which have their 3'-ends blocked and are very stable to degradation by exonucleases, showed similar immunostimulatory activity. Oligos 4 and 8 may show sustained immunostimulatory activity due to their increased in vivo stability, which is not evident in the present study as mice were sacrificed at only 72 hours after administration. Studies are in progress in which mice will be sacrificed at times later than 72 hours after administration.

The results described here are intriguing and suggest that the 5'-end of CpG-PS-oligos is critical for immunostimulatory activity. As discussed here, we have shown that substitution of deoxynucleosides in 5'-flanking regions by modified 2'- or 3'substituted ribonucleosides resulted in increased immunostimulatory activity. In addition, substitution of deoxynucleosides immediately upstream (5'-end) to the CpG motif caused a significant suppression and substitution of deoxynucleosides immediately downstream (3'-end) to the CpG motif had no effect on immunostimulatory activity. Taken together, these results suggest that the enzyme/receptor responsible for the immunestimulation recognizes the CpG motif in oligos from the 5'-end and requires accessibility to the 5'-end.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for generating an immune response in a patient, such method comprising administering to the patient an immunostimulatory oligonucleotide compound, comprising an immunostimulatory dinucleotide of formula C*pG, wherein the immunostimulatory oligonucleotide compound is at least 6 nucleotides in length, wherein C* is a non-natural pyrimidine nucleoside selected from the group consisting of 5-hydroxycytosine, 5-hydroxymethylcytosine, N4-alkylcytosine-and 4-thiouracil, and G is guanosine and p is an internucleotide linkage selected from the group consisting of phosphorothiate and phosphorodithioate.

2. The method according to claim 1, wherein the immunostimulatory oligonucleotide compound is conjugated to an antigen.

3. The method according to claim 2, wherein such conjugation is to the 3'-end of the oligonucleotide compound.

4. A method for treating a cancer patient, such method comprising administering to the patient an immunostimulatory oligonucleotide compound, comprising an immunostimulatory dinucleotide of formula C*pG, wherein the immunostimulatorv oligonucleotide compound is at least 6 nucleotides in length, wherein C* is a non-natural pyrimidine nucleoside selected from the group consisting of 5-hydroxycytosine, 5-hydroxymethylcytosine, N4-alkylcytosine and 4-thiouracil,and G is guanosine and p is an internucleotide linkage selected from the group consisting of phosphorothiate and phosphorodithioate.

5. The method according to claim 4, wherein the immunostimulatory oligonucleotide compound is administered in combination with a chemotherapeutic compound.

6. The method according to claim 1, wherein the immunostimulatorv oligonucleotide compound is administered in combination with an antibiotic, antigen, allergen, antibody, cytotoxic agent, antisense oligonucleotide, adjuvant, or combination thereof.

7. The method according to claim 1, wherein the immunostimulatorv oligonucleotide compound is administered in combination with an antibiotic, antigen, allergen, antibody, cytotoxic agent, antisense oligonucleotide, adjuvant, or combination thereof.

* * * * *

SEQUENCE LISTING

<160> NUMBER OF SEQ ID NOS: 112

<210> SEQ ID NO 1
<211> LENGTH: 18
<212> TYPE: DNA
<213> ORGANISM: Artificial Sequence
<220> FEATURE:
<223> OTHER INFORMATION: synthesis of CpG-PS-oligos containing cytosine analogs

<400> SEQUENCE: 1
ctatctgacg ttctctgt                                                        18

<210> SEQ ID NO 2
<211> LENGTH: 18
<212> TYPE: DNA
<213> ORGANISM: Artificial Sequence
<220> FEATURE:
<223> OTHER INFORMATION: synthesis of CpG-PS-oligos containing cytosine analogs
<220> FEATURE:
<221> NAME/KEY: modified_base
<222> LOCATION: 9
<223> OTHER INFORMATION: c = 5-hydroxydeoxycytidine

<400> SEQUENCE: 2
ctatctgacg ttctctgt                                                        18

<210> SEQ ID NO 3
<211> LENGTH: 18
<212> TYPE: DNA
<213> ORGANISM: Artificial Sequence
<220> FEATURE:
<223> OTHER INFORMATION: synthesis of CpG-PS-oligos containing cytosine analogs
<220> FEATURE:
<221> NAME/KEY: modified_base
<222> LOCATION: 10
<223> OTHER INFORMATION: c = 5-hydroxydeoxycytidine

<400> SEQUENCE: 3
ctatctgacc ttctctgt                                                        18

<210> SEQ ID NO 4
<211> LENGTH: 18
<212> TYPE: DNA
<213> ORGANISM: Artificial Sequence
<220> FEATURE:
<223> OTHER INFORMATION: synthesis of CpG-PS-oligos containing cytosine analogs
<220> FEATURE:
<221> NAME/KEY: modified_base
<222> LOCATION: 9
<223> OTHER INFORMATION: c = N4-ethyldeoxycytidine

<400> SEQUENCE: 4
ctatctgacg ttctctgt                                                        18

<210> SEQ ID NO 5
<211> LENGTH: 18
<212> TYPE: DNA
<213> ORGANISM: Artificial Sequence
<220> FEATURE:
<223> OTHER INFORMATION: synthesis of CpG-PS-oligos containing cytosine analogs
<220> FEATURE:
<221> NAME/KEY: modified_base
<222> LOCATION: 10

```
<223> OTHER INFORMATION: c = N4-ethyldeoxycytidine

<400> SEQUENCE: 5
ctatctgacc ttctctgt                                                  18

<210> SEQ ID NO 6
<211> LENGTH: 16
<212> TYPE: DNA
<213> ORGANISM: Artificial Sequence
<220> FEATURE:
<223> OTHER INFORMATION: synthesis of end-blocked CpG-PS modified
      oligodeoxynucleotide phosphorothioate

<400> SEQUENCE: 6
aaggtcgagc gttctc                                                    16

<210> SEQ ID NO 7
<211> LENGTH: 18
<212> TYPE: DNA
<213> ORGANISM: Artificial Sequence
<220> FEATURE:
<223> OTHER INFORMATION: synthesis of end-blocked CpG-PS modified
      oligodeoxynucleotide
      phosphorothioate

<400> SEQUENCE: 7
atggcgcacg ctgggaga                                                  18

<210> SEQ ID NO 8
<211> LENGTH: 18
<212> TYPE: DNA
<213> ORGANISM: Artificial Sequence
<220> FEATURE:
<223> OTHER INFORMATION: oligodeoxynucleotide phosphorothioate

<400> SEQUENCE: 8
cctactagcg ttctcatc                                                  18

<210> SEQ ID NO 9
<211> LENGTH: 18
<212> TYPE: DNA
<213> ORGANISM: Artificial Sequence
<220> FEATURE:
<223> OTHER INFORMATION: oligodeoxynucleotide phosphorothioate
<220> FEATURE:
<221> NAME/KEY: modified_base
<222> LOCATION: 10
<223> OTHER INFORMATION: g = 1',2'-Dideoxyribose

<400> SEQUENCE: 9
cctactagcg ttctcatc                                                  18

<210> SEQ ID NO 10
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 8
<223> OTHER INFORMATION: g = 1',2'-Dideoxyribose

<400> SEQUENCE: 10
cctactagcg ttctcatc                                                  18

<210> SEQ ID NO 11
```

```
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 7
<223> OTHER INFORMATION: a = 1',2'-Dideoxyribose

<400> SEQUENCE: 11
cctactagcg ttctcatc                                                 18

<210> SEQ ID NO 12
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 6
<223> OTHER INFORMATION: t = 1',2'-Dideoxyribose

<400> SEQUENCE: 12
cctactagcg ttctcatc                                                 18

<210> SEQ ID NO 13
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 5
<223> OTHER INFORMATION: c = 1',2'-Dideoxyribose

<400> SEQUENCE: 13
cctactagcg ttctcatc                                                 18

<210> SEQ ID NO 14
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: a = 1',2'-Dideoxyribose

<400> SEQUENCE: 14
cctactagcg ttctcatc                                                 18

<210> SEQ ID NO 15
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: a = 1',2'-Dideoxyribose

<400> SEQUENCE: 15
cctactagcc ttctcatc                                                 18
```

```
<210> SEQ ID NO 16
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 11
<223> OTHER INFORMATION: t = 1',2'-Dideoxyribose

<400> SEQUENCE: 16
cctactagcg ttctcatc                                                 18

<210> SEQ ID NO 17
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 12
<223> OTHER INFORMATION: t = 1',2'-Dideoxyribose

<400> SEQUENCE: 17
cctactagcg ttctcatc                                                 18

<210> SEQ ID NO 18
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 13
<223> OTHER INFORMATION: c = 1',2'-Dideoxyribose

<400> SEQUENCE: 18
cctactagcg ttctcatc                                                 18

<210> SEQ ID NO 19
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = 1',2'-Dideoxyribose

<400> SEQUENCE: 19
cctactagcg ttctcatc                                                 18

<210> SEQ ID NO 20
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4, 5
<223> OTHER INFORMATION: ac = 1',2'-Dideoxyribose

<400> SEQUENCE: 20
cctactagcg ttctcatc                                                 18
```

<210> SEQ ID NO 21
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 1, 2
<223> OTHER INFORMATION: cc = 1',2'-Dideoxyribose

<400> SEQUENCE: 21
cctactagcg ttctcatc                                                 18

<210> SEQ ID NO 22
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14, 15
<223> OTHER INFORMATION: tc = 1',2'-Dideoxyribose

<400> SEQUENCE: 22
cctactagcg ttctcatc                                                 18

<210> SEQ ID NO 23
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4, 7
<223> OTHER INFORMATION: a at position 4 = 1',2'-Dideoxyribose
      a at position 7 = 1',2'-Dideoxyribose

<400> SEQUENCE: 23
cctactagcg ttctcatc                                                 18

<210> SEQ ID NO 24
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 10
<223> OTHER INFORMATION: g = C3-Linker

<400> SEQUENCE: 24
cctactagcg ttctcatc                                                 18

<210> SEQ ID NO 25
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 7
<223> OTHER INFORMATION: a = C3-Linker

```
<400> SEQUENCE: 25
cctactagcg ttctcatc                                                    18

<210> SEQ ID NO 26
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = C3-Linker

<400> SEQUENCE: 26
cctactagcg ttctcatc                                                    18

<210> SEQ ID NO 27
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5
<223> OTHER INFORMATION: a at position 4 = C3-Linker
      c at position 5 = C3-Linker

<400> SEQUENCE: 27
cctactagcg ttctcatc                                                    18

<210> SEQ ID NO 28
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 1, 2
<223> OTHER INFORMATION: cc at positions 1 & 2 = C3-Linker

<400> SEQUENCE: 28
cctactagcg ttctcatc                                                    18

<210> SEQ ID NO 29
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 12
<223> OTHER INFORMATION: t = C3-Linker

<400> SEQUENCE: 29
cctactagcg ttctcatc                                                    18

<210> SEQ ID NO 30
<211> LENGTH: 18
<212> TYPE: DNA
<213> ORGANISM: Artificial Sequence
<220> FEATURE:
```

<223> OTHER INFORMATION: modified linkage of oligodeoxynucleotide
      phosphorothioate
<220> FEATURE:
<221> NAME/KEY: modified_base
<222> LOCATION: 14
<223> OTHER INFORMATION: t = C3-Linker

<400> SEQUENCE: 30
cctactagcg ttctcatc                                            18

<210> SEQ ID NO 31
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 14, 15
<223> OTHER INFORMATION: t at position 14 = C3-Linker
      c at position 15 = C3-Linker

<400> SEQUENCE: 31
cctactagcg ttctcatc                                            18

<210> SEQ ID NO 32
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 8
<223> OTHER INFORMATION: a = C3-Linker

<400> SEQUENCE: 32
ctatctgacg ttctctgt                                            18

<210> SEQ ID NO 33
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 6
<223> OTHER INFORMATION: t = C3-Linker

<400> SEQUENCE: 33
ctatctgacg ttctctgt                                            18

<210> SEQ ID NO 34
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4
<223> OTHER INFORMATION: t = C3-Linker

<400> SEQUENCE: 34
ctatctgacg ttctctgt                                            18

```
<210> SEQ ID NO 35
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: t = Spacer9

<400> SEQUENCE: 35
ctatctgacg ttctctgt                                                 18

<210> SEQ ID NO 36
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = Spacer9

<400> SEQUENCE: 36
ctatctgacg ttctctgt                                                 18

<210> SEQ ID NO 37
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: t = Spacer18

<400> SEQUENCE: 37
ctatctgacg ttctctgt                                                 18

<210> SEQ ID NO 38
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = Spacer18

<400> SEQUENCE: 38
ctatctgacg ttctctgt                                                 18

<210> SEQ ID NO 39
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: a = Spacer9

<400> SEQUENCE: 39
```
cctactagcg ttctcatc                                                        18

<210> SEQ ID NO 40
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = Spacer9

<400> SEQUENCE: 40
cctactagcg ttctcatc                                                        18

<210> SEQ ID NO 41
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: a = Spacer18

<400> SEQUENCE: 41
cctactagcg ttctcatc                                                        18

<210> SEQ ID NO 42
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = Spacer18

<400> SEQUENCE: 42
cctactagcg ttctcatc                                                        18

<210> SEQ ID NO 43
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 8
<223> OTHER INFORMATION: a = Amino-Linker

<400> SEQUENCE: 43
ctatctgacg ttctctgt                                                        18

<210> SEQ ID NO 44
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 7
<223> OTHER INFORMATION: g = Amino-Linker

<400> SEQUENCE: 44
ctatctgacg ttctctgt                                                 18

<210> SEQ ID NO 45
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: t = Amino-Linker

<400> SEQUENCE: 45
ctatctgacg ttctctgt                                                 18

<210> SEQ ID NO 46
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 12
<223> OTHER INFORMATION: t = Amino-Linker

<400> SEQUENCE: 46
ctatctgacg ttctctgt                                                 18

<210> SEQ ID NO 47
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 14
<223> OTHER INFORMATION: t = Amino-Linker

<400> SEQUENCE: 47
ctatctgacg ttctctgt                                                 18

<210> SEQ ID NO 48
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 10
<223> OTHER INFORMATION: g = 3'-Deoxynucleoside

<400> SEQUENCE: 48
ctatctgacg ttctctgt                                                 18

<210> SEQ ID NO 49
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 9

<223> OTHER INFORMATION: c = 3'-Deoxynucleoside

<400> SEQUENCE: 49
ctatctgacg ttctctgt                                                          18

<210> SEQ ID NO 50
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = 3'-Deoxynucleoside

<400> SEQUENCE: 50
ctatctgacg ttctctgt                                                          18

<210> SEQ ID NO 51
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 15
<223> OTHER INFORMATION: c = 3'-Deoxynucleoside

<400> SEQUENCE: 51
ctatctgacg ttctctgt                                                          18

<210> SEQ ID NO 52
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 10
<223> OTHER INFORMATION: g = 3'-Deoxynucleoside

<400> SEQUENCE: 52
cctactagcg ttctcatc                                                          18

<210> SEQ ID NO 53
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 9
<223> OTHER INFORMATION: c = 3'-Deoxynucleoside

<400> SEQUENCE: 53
cctactagcg ttctcatc                                                          18

<210> SEQ ID NO 54
<211> LENGTH: 18
<212> TYPE: DNA
<213> ORGANISM: Artificial Sequence

```
<220> FEATURE:
<223> OTHER INFORMATION: modified linkage of oligodeoxynucleotide
      phosphorothioate
<220> FEATURE:
<221> NAME/KEY: modified_base
<222> LOCATION: 8
<223> OTHER INFORMATION: g = 3'-Deoxynucleoside

<400> SEQUENCE: 54
cctactagcg ttctcatc                                                      18

<210> SEQ ID NO 55
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = 3'-Deoxynucleoside

<400> SEQUENCE: 55
cctactagcg ttctcatc                                                      18

<210> SEQ ID NO 56
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 15
<223> OTHER INFORMATION: c = 3'-Deoxynucleoside

<400> SEQUENCE: 56
cctactagcg ttctcatc                                                      18

<210> SEQ ID NO 57
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 8
<223> OTHER INFORMATION: a = Methyl-phosphonate

<400> SEQUENCE: 57
ctatctgacg ttctctgt                                                      18

<210> SEQ ID NO 58
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 7
<223> OTHER INFORMATION: g = Methyl-phosphonate

<400> SEQUENCE: 58
ctatctgacg ttctctgt                                                      18
```

<210> SEQ ID NO 59
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 6
<223> OTHER INFORMATION: t = Methyl-phosphonate

<400> SEQUENCE: 59
ctatctgacg ttctctgt                                                 18

<210> SEQ ID NO 60
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = Methyl-phosphonate

<400> SEQUENCE: 60
ctatctgacg ttctctgt                                                 18

<210> SEQ ID NO 61
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4
<223> OTHER INFORMATION: t = Methyl-phosphonate

<400> SEQUENCE: 61
ctatctgacg ttctctgt                                                 18

<210> SEQ ID NO 62
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 3, 4
<223> OTHER INFORMATION: a at position 3 = Methyl-phosphonate
      t at position 4 = Methyl-phosphonate

<400> SEQUENCE: 62
ctatctgacg ttctctgt                                                 18

<210> SEQ ID NO 63
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:

```
<221> NAME/KEY: modified_base
<222> LOCATION: 11
<223> OTHER INFORMATION: t = Methyl-phosphonate

<400> SEQUENCE: 63
ctatctgacg ttctctgt                                                        18

<210> SEQ ID NO 64
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 12
<223> OTHER INFORMATION: t = Methyl-phosphonate

<400> SEQUENCE: 64
ctatctgacg ttctctgt                                                        18

<210> SEQ ID NO 65
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 13
<223> OTHER INFORMATION: c = Methyl-phosphonate

<400> SEQUENCE: 65
ctatctgacg ttctctgt                                                        18

<210> SEQ ID NO 66
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 14
<223> OTHER INFORMATION: t = Methyl-phosphonate

<400> SEQUENCE: 66
ctatctgacg ttctctgt                                                        18

<210> SEQ ID NO 67
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 15
<223> OTHER INFORMATION: c = Methyl-phosphonate

<400> SEQUENCE: 67
ctatctgacg ttctctgt                                                        18

<210> SEQ ID NO 68
<211> LENGTH: 18
```

```
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 15, 16
<223> OTHER INFORMATION: c at position 15 = Methyl-phosphonate
      t at position 16 = Methyl-phosphonate

<400> SEQUENCE: 68
ctatctgacg ttctctgt                                                 18

<210> SEQ ID NO 69
<211> LENGTH: 19
<212> TYPE: DNA
<213> ORGANISM: Artificial Sequence
<220> FEATURE:
<223> OTHER INFORMATION: modified linkage of oligodeoxynucleotide
      phosphorothioate

<400> SEQUENCE: 69
tccatgacgt tcctgatgc                                                19

<210> SEQ ID NO 70
<211> LENGTH: 19
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 7
<223> OTHER INFORMATION: a = 2'-O-Methylribonucleoside

<400> SEQUENCE: 70
tccatgacgt tcctgatgc                                                19

<210> SEQ ID NO 71
<211> LENGTH: 19
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: t = 2'-O-Methylribonucleoside

<400> SEQUENCE: 71
tccatgacgt tcctgatgc                                                19

<210> SEQ ID NO 72
<211> LENGTH: 19
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 2, 3
<223> OTHER INFORMATION: c at positions 2 & 3 =
      2'-O-Methoxyethylribonucleoside

<400> SEQUENCE: 72
tccatgacgg tcctgatgc                                                19
```

<210> SEQ ID NO 73
<211> LENGTH: 16
<212> TYPE: DNA
<213> ORGANISM: Artificial Sequence
<220> FEATURE:
<223> OTHER INFORMATION: modified linkage of oligodeoxynucleotide phosphorothioate

<400> SEQUENCE: 73
gagaacgctc gacctt                                                         16

<210> SEQ ID NO 74
<211> LENGTH: 32
<212> TYPE: DNA
<213> ORGANISM: Artificial Sequence
<220> FEATURE:
<223> OTHER INFORMATION: modified linkage of oligodeoxynucleotide phosphorothioate
<220> FEATURE:
<221> NAME/KEY: modified_base
<222> LOCATION: 16
<223> OTHER INFORMATION: 3'-5' linkage

<400> SEQUENCE: 74
gagaacgctc gaccttgaga acgctcgacc tt                                       32

<210> SEQ ID NO 75
<211> LENGTH: 32
<212> TYPE: DNA
<213> ORGANISM: Artificial Sequence
<220> FEATURE:
<223> OTHER INFORMATION: modified linkage of oligodeoxynucleotide phosphorothioate
<220> FEATURE:
<221> NAME/KEY: modified_base
<222> LOCATION: 16
<223> OTHER INFORMATION: 5'-5' linkage

<400> SEQUENCE: 75
ttccagctcg caagaggaga acgctcgacc tt                                       32

<210> SEQ ID NO 76
<211> LENGTH: 32
<212> TYPE: DNA
<213> ORGANISM: Artificial Sequence
<220> FEATURE:
<223> OTHER INFORMATION: modified linkage of oligodeoxynucleotide phosphorothioate
<220> FEATURE:
<221> NAME/KEY: modified_base
<222> LOCATION: 16
<223> OTHER INFORMATION: 3'-3' linkage

<400> SEQUENCE: 76
gagaacgctc gacctttcc agctcgcaag ag                                        32

<210> SEQ ID NO 77
<211> LENGTH: 18
<212> TYPE: DNA
<213> ORGANISM: Artificial Sequence
<220> FEATURE:
<223> OTHER INFORMATION: modified linkage of oligodeoxynucleotide phosphorothioate

<400> SEQUENCE: 77
tctcccagcg tgcgccat                                                       18

```
<210> SEQ ID NO 78
<211> LENGTH: 32
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 16
<223> OTHER INFORMATION: 3'-5' linkage

<400> SEQUENCE: 78
tcccagcgtg cgccattccc agcgtgcgcc at                                      32

<210> SEQ ID NO 79
<211> LENGTH: 32
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 16
<223> OTHER INFORMATION: 5'-5' linkage

<400> SEQUENCE: 79
taccgcgtgc gacccttccc agcgtgcgcc at                                      32

<210> SEQ ID NO 80
<211> LENGTH: 32
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 16
<223> OTHER INFORMATION: 3'-3' linkage

<400> SEQUENCE: 80
tcccagcgtg cgccattacc gcgtgcgacc ct                                      32

<210> SEQ ID NO 81
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = beta-L-Deoxynucleoside

<400> SEQUENCE: 81
ctatctgacg ttctctgt                                                      18

<210> SEQ ID NO 82
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 14
<223> OTHER INFORMATION: t = beta-L-Deoxynucleoside
```

```
<400> SEQUENCE: 82
ctatctgacg ttctctgt                                                    18

<210> SEQ ID NO 83
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5
<223> OTHER INFORMATION: t at position 4 = beta-L-Deoxynucleoside
      c at position 5 = beta-L-Deoxynucleoside

<400> SEQUENCE: 83
ctatctgacg ttctctgt                                                    18

<210> SEQ ID NO 84
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 14, 15
<223> OTHER INFORMATION: t at position 14 = beta-L-Deoxynucleoside
      c at position 15 = beta-L-Deoxynucleoside

<400> SEQUENCE: 84
ctatctgacg ttctctgt                                                    18

<210> SEQ ID NO 85
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 9, 10
<223> OTHER INFORMATION: c at position 9 = beta-L-Deoxynucleoside
      g at position 10 = beta-L-Deoxynucleoside

<400> SEQUENCE: 85
ctatctgacg ttctctgt                                                    18

<210> SEQ ID NO 86
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 7
<223> OTHER INFORMATION: g = beta-L-Deoxynucleoside

<400> SEQUENCE: 86
ctatctgacg ttctctgt                                                    18

<210> SEQ ID NO 87
<211> LENGTH: 18
```

```
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 12
<223> OTHER INFORMATION: t = beta-L-Deoxynucleoside

<400> SEQUENCE: 87
ctatctgacg ttctctgt                                                  18

<210> SEQ ID NO 88
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: (1)...(18)
<223> OTHER INFORMATION: all nucleotides = beta-L-deoxynucleoside

<400> SEQUENCE: 88
ctatctgacg ttctctgt                                                  18

<210> SEQ ID NO 89
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 5
<223> OTHER INFORMATION: c = 2'-O-Propargyl-ribonucleoside

<400> SEQUENCE: 89
ctatctgacg ttctctgt                                                  18

<210> SEQ ID NO 90
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 15
<223> OTHER INFORMATION: c = 2'-O'Propargyl-ribonucleoside

<400> SEQUENCE: 90
ctatctgacg ttctctgt                                                  18

<210> SEQ ID NO 91
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5
<223> OTHER INFORMATION: a at position 4 = 1',2'-Dideoxyribose
      c at position 5 = 1',2'-Dideoxyribose
```

```
<400> SEQUENCE: 91
cctactagcg ttctcatc                                              18

<210> SEQ ID NO 92
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5
<223> OTHER INFORMATION: a at position 4 = C3-Linker
      c at position 5 = C3-Linker

<400> SEQUENCE: 92
cctactagcg ttctcatc                                              18

<210> SEQ ID NO 93
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5
<223> OTHER INFORMATION: a at position 4 = 3'-methoxyribonucleoside
      c at position 5 = 3'-methyoxyribonucleoside

<400> SEQUENCE: 93
cctactagcg ttctcatc                                              18

<210> SEQ ID NO 94
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate
<220> FEATURE:
<221> NAME/KEY: modified_base
<222> LOCATION: 4, 5, 12
<223> OTHER INFORMATION: a at position 4 = 1',2'-Dideoxyribose
      c at position 5 = 1',2'-Dideoxyribose
      t at position 12 = 2'-methoxyribonucleoside

<400> SEQUENCE: 94
cctactagcg ttctcatc                                              18

<210> SEQ ID NO 95
<211> LENGTH: 18
<212> TYPE: DNA
<213> ORGANISM: Artificial Sequence
<220> FEATURE:
<223> OTHER INFORMATION: modified linkage of oligodeoxynucleotide
      phosphorothioate

<400> SEQUENCE: 95
cctactaggc ttctcatc                                              18

<210> SEQ ID NO 96
<211> LENGTH: 18
<212> TYPE: DNA
<213> ORGANISM: Artificial Sequence
<220> FEATURE:
<223> OTHER INFORMATION: modified oligodeoxynucleotide phosphorothioate
```

```
<220> FEATURE:
<221> NAME/KEY: modified_base
<222> LOCATION: 10
<223> OTHER INFORMATION: g = 7-deazaguanine

<400> SEQUENCE: 96
ctatctgacg ttctctgt                                                 18

<210> SEQ ID NO 97
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 9
<223> OTHER INFORMATION: g = 7-deazaguanine

<400> SEQUENCE: 97
ctatctgagc ttctctgt                                                 18

<210> SEQ ID NO 98
<211> LENGTH: 18
<212> TYPE: DNA
<213> ORGANISM: Artificial Sequence
<220> FEATURE:
<223> OTHER INFORMATION: modified oligodeoxynucleotide phosphorothioate

<400> SEQUENCE: 98
tctcccagcg tgcgccat                                                 18

<210> SEQ ID NO 99
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 10,14
<223> OTHER INFORMATION: g at positions 10 and 14 = 7-deazaguanine

<400> SEQUENCE: 99
tctcccagcg tgcgccat                                                 18

<210> SEQ ID NO 100
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 5
<223> OTHER INFORMATION: c = C3-Linker
<220> FEATURE:
<221> NAME/KEY: modified_base
<222> LOCATION: 10
<223> OTHER INFORMATION: g = 7-deazaguanine

<400> SEQUENCE: 100
ctatctgacg ttctctgt                                                 18

<210> SEQ ID NO 101
<211> LENGTH: 18
<212> TYPE: DNA
<213> ORGANISM: Artificial Sequence
<220> FEATURE:
```

```
<223> OTHER INFORMATION: modified oligodeoxynucleotide phosphorothioate
<220> FEATURE:
<221> NAME/KEY: modified_base
<222> LOCATION: 10
<223> OTHER INFORMATION: g = 6-thioguanine

<400> SEQUENCE: 101
ctatctgacg ttctctgt                                                    18

<210> SEQ ID NO 102
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 9
<223> OTHER INFORMATION: g = 6-thioguanine

<400> SEQUENCE: 102
ctatctgagc ttctctgt                                                    18

<210> SEQ ID NO 103
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 9
<223> OTHER INFORMATION: c = 4-thiouridine

<400> SEQUENCE: 103
ctatctgacg ttctctgt                                                    18

<210> SEQ ID NO 104
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 5
<223> OTHER INFORMATION: c = 1,2-Dideoxyribose
<220> FEATURE:
<221> NAME/KEY: modified_base
<222> LOCATION: 9
<223> OTHER INFORMATION: c = 4-thiouridine

<400> SEQUENCE: 104
ctatctgacg ttctctgt                                                    18

<210> SEQ ID NO 105
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 9
<223> OTHER INFORMATION: c = Ara-C

<400> SEQUENCE: 105
ctatctgacg ttctctgt                                                    18
```

```
<210> SEQ ID NO 106
<211> LENGTH: 19
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 10
<223> OTHER INFORMATION: c = Ara-C

<400> SEQUENCE: 106
ctactctgac cttctctgt                                                19

<210> SEQ ID NO 107
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 9
<223> OTHER INFORMATION: c = 1',2'-Dideoxyribose

<400> SEQUENCE: 107
ctatctgacg ttctctgt                                                 18

<210> SEQ ID NO 108
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 8
<223> OTHER INFORMATION: a = 1',2'-Dideoxyribose

<400> SEQUENCE: 108
ctatctgacg ttctctgt                                                 18

<210> SEQ ID NO 109
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 6
<223> OTHER INFORMATION: t = 1',2'-Dideoxyribose

<400> SEQUENCE: 109
ctatctgacg ttctctgt                                                 18

<210> SEQ ID NO 110
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 4
<223> OTHER INFORMATION: t = 1',2'-Dideoxyribose

<400> SEQUENCE: 110
ctatctgacg ttctctgt                                                 18
```

```
<210> SEQ ID NO 111
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 11
<223> OTHER INFORMATION: t = 1',2'-Dideoxyribose

<400> SEQUENCE: 111
ctatctgacg ttctctgt                                                 18

<210> SEQ ID NO 112
<211> LENGTH: 18
<212> TYPE: DNA
<213> ORGANISM: Artificial Sequence
<220> FEATURE:
<223> OTHER INFORMATION: modified oligodeoxynucleotide phosphorothioate
<220> FEATURE:
<221> NAME/KEY: modified_base
<222> LOCATION: 13
<223> OTHER INFORMATION: c = 1',2'-Dideoxyribose

<400> SEQUENCE: 112
ctatctgacg ttctctgt                                                 18
```